United States Patent
Bebbington et al.

(10) Patent No.: US 11,773,162 B2
(45) Date of Patent: Oct. 3, 2023

(54) ANTI-SIGLEC-7 ANTIBODIES FOR THE TREATMENT OF CANCER

(71) Applicant: Allakos, Inc., San Carlos, CA (US)

(72) Inventors: Christopher Bebbington, San Carlos, CA (US); Wouter Korver, San Carlos, CA (US); Nenad Tomasevic, San Carlos, CA (US); Suzy El Bader, San Carlos, CA (US); Kenneth Luehrsen, San Carlos, CA (US)

(73) Assignee: Allakos, Inc., San Carlos, CA (US)

( * ) Notice: Subject to any disclaimer, the term of this patent is extended or adjusted under 35 U.S.C. 154(b) by 1073 days.

(21) Appl. No.: 16/323,442

(22) PCT Filed: Aug. 4, 2017

(86) PCT No.: PCT/US2017/045641
§ 371 (c)(1),
(2) Date: Feb. 5, 2019

(87) PCT Pub. No.: WO2018/027203
PCT Pub. Date: Feb. 8, 2018

(65) Prior Publication Data
US 2019/0194323 A1 Jun. 27, 2019

Related U.S. Application Data

(60) Provisional application No. 62/371,680, filed on Aug. 5, 2016.

(51) Int. Cl.
*C07K 16/28* (2006.01)
*A61P 35/00* (2006.01)
*A61K 38/00* (2006.01)

(52) U.S. Cl.
CPC .......... *C07K 16/2803* (2013.01); *A61P 35/00* (2018.01); *A61K 38/00* (2013.01);
(Continued)

(58) Field of Classification Search
CPC ............ C07K 16/2803; C07K 2317/24; C07K 2317/92; C07K 2317/77; A61P 35/00; A61K 38/00
See application file for complete search history.

(56) References Cited

U.S. PATENT DOCUMENTS

2007/0244038 A1 10/2007 Varki et al.
2010/0240872 A1 9/2010 Nakano
(Continued)

FOREIGN PATENT DOCUMENTS

WO 2016/038064 A1 3/2016
WO 2017040301 A1 3/2017
(Continued)

OTHER PUBLICATIONS

Herold, E.M., John, C., Weber, B. et al. Determinants of the assembly and function of antibody variable domains. Sci Rep 7, 12276 (2017). https://doi.org/10.1038/s41598-017-12519-9 (Year: 2017).*

(Continued)

*Primary Examiner* — Scarlett Y Goon
*Assistant Examiner* — Jessica Soto-Rodriguez
(74) *Attorney, Agent, or Firm* — Kilpatrick Townsend & Stockton LLP

(57) ABSTRACT

The invention provides methods and compositions for the treatment of cancer using anti-Siglec7 antibodies.

14 Claims, 11 Drawing Sheets

Specification includes a Sequence Listing.

| mAb | KD (pM)* |
|---|---|
| 5215-9 | 1 |
| 8A2 | 1 |
| 5D1 | 1 |
| 5215-21 | 1 |
| 5G10 | 1 |
| 5215-28 | 1 |
| 16H11/21B2 | 35 |
| 3F1 | 41 |
| | 86 |
| 5215-2 | 149 |
| 5215-11 | 159 |
| 2G12 | 205 |
| 4B12 | 260 |
| 5215-7 | 273 |
| | 422 |
| 10E11 | 522 |
| 13D2 | 536 |
| | 706 |
| 9D4hu | 760 |
| 9D4 | 760 |
| 5215-13 | 990 |
| 5215-18 | 3500 |

3F1 $K_D$=41pM

QA79 $K_D$=706pM

(52) U.S. Cl.
CPC ...... *C07K 2317/24* (2013.01); *C07K 2317/77* (2013.01); *C07K 2317/92* (2013.01)

(56) References Cited

U.S. PATENT DOCUMENTS

| | | | |
|---|---|---|---|
| 2014/0193427 A1* | 7/2014 | Lerner | C07K 16/22 |
| | | | 435/69.6 |
| 2014/0363826 A1 | 12/2014 | Stull et al. | |
| 2016/0115231 A1* | 4/2016 | Levi-Schaffer | A61P 35/00 |
| | | | 435/375 |
| 2017/0226203 A1 | 8/2017 | Komai et al. | |
| 2019/0194323 A1 | 6/2019 | Bebbington et al. | |

FOREIGN PATENT DOCUMENTS

| | | |
|---|---|---|
| WO | 2017123745 A1 | 7/2017 |
| WO | 2017153433 A1 | 9/2017 |

OTHER PUBLICATIONS

Chailyan A, Marcatili P, Tramontano A. The association of heavy and light chain variable domains in antibodies: implications for antigen specificity. FEBS J.Aug. 2011;278(16):2858-66. doi: 10.1111/j.1742-4658.2011.08207.x. Epub Jun. 28, 2011. PMID: 21651726; PMCID: PMC3562479. (Year: 2011).*

Tsuchiya, Y. and Mizuguchi, K. (2016), The diversity of H3 loops determines the antigen-binding tendencies of antibody CDR loops. Protein Science, 25: 815-825. (Year: 2016).*

Nicole M. Piche-Nicholas, et al. (2017) Changes in complementarity-determining regions significantly alter IgG binding to the neonatal Fc receptor (FcRn) and pharmacokinetics, mAbs, 10:1, 81-94 (Year: 2017).*

PCT/US2017/045641, International Search Report and Written Opinion, dated Jan. 4, 2018, 16 pages.

EP17837808.9 , "Extended European Search Report", dated Mar. 4, 2020, 15 pages.

Hudak et al., "Glycocalyx Engineering Reveals a Siglec-Based Mechanism for NK Cell Immunoevasion-Paper", Nature Chemical Biology, vol. 10, No. 1, Jan. 1, 2014, pp. 69-75.

Jandus et al., "Interactions Between Siglec-7/9 Receptors and Ligands Influence NK Cell-Dependent Tumor Immunosurveillance", Journal of Clinical Investigation, vol. 124, No. 4, Feb. 24, 2014, pp. 1810-1820.

Kawasaki et al., "Targeted Delivery of Mycobacterial Antigens to Human Dendritic Cells via Siglec-7 Induces Robust T Cell Activation", The Journal of Immunology, vol. 193, No. 4, Jul. 7, 2014, pp. 1560-1566.

Mitsuki et al., "Siglec-7 Mediates Nonapoptotic Cell Death Independently of its Immunoreceptor Tyrosine-Based Inhibitory Motifs in Monocytic Cell Line U937", Glycobiology, vol. 20, No. 3, 2010, pp. 395-402.

Nicoll et al., "Identification and Characterization of a Novel Siglec, Siglec-7, Expressed by Human Natural Killer Cells and Monocytes", Journal of Biological Chemistry, American Society for Biochemistry and Molecular Biology, vol. 274, No. 48, Nov. 26, 1999, pp. 34089-34095.

Varchetta et al., "Engagement of Siglec-7 Receptor Induces a Pro-Inflammatory Response Selectively in Monocytes", PLoS ONE, vol. 7, No. 9, e45821, Sep. 28, 2012, 12 pages.

Varchetta et al., "Sialic Acid-Binding Ig-Like Lectin-7 Interacts with HIV-1 Gp120 and Facilitates Infection of CD4pos T Cells and Macrophages", Retrovirology, Biomed Central Ltd., London, GB, vol. 10, No. 154, Dec. 13, 2013, pp. 1-13.

EP17837808.9, "Examination Report," dated Aug. 11, 2022, 6 pages.

Rudikoff, et al., "Single amino acid substitution altering antigen-binding specificity," Proceedings National Academy of Sciences PNAS, National Academy of Sciences, Mar. 1982, vol. 79, No. 6, pp. 1979-1983.

Orr et al., "SOCS3 Targets Siglec 7 forProteasomal Degradation and Blocks Siglec7-mediated Responses", Journal of Biological Chemistry, vol. 282, No. 6, Nov. 30, 2006, pp. 3418-3422.

PCT/US2019/013316, "International Search Report and Written Opinion", dated Jun. 21, 2019, 13 pages.

PCT/US2019/013316, "Invitation to Pay Additional Fees and, Where Applicable, Protest Fee", Apr. 15, 2019, 3 pages.

"Human Siglec-7/CD328 Antibody", Available Online at: https://resources.mdsystems.com/pdfs/datasheets/af1138.pdf, Oct. 13, 2015, pp. 1-2.

Angata et al., "Therapeutic Targeting of Siglecs Using Antibody- and Glycan-Based Approaches", Trends in Pharmacological Sciences, vol. 36, No. 10, Oct. 2015, pp. 645-660.

Application No. EP19739010.7 , Extended European Search Report, dated Mar. 21, 2022, 10 pages.

Lo, et al., "Conformational epitope matching and prediction based on protein surface spiral features," BMC Genomics 2021, 22 (Suupl 2):116, 16 pages.

Altshuler, et al., "Generation of RecombinantAntibodiesand Means for Increasing Their Affinity," Biochemistry (Moscow), vol. 75, No. 13, 2010, pp. 1584-1605.

Lippow, et al., "Computational design of antibody-affinity improvement beyond in vivo maturation," Nature Biotechnology, vol. 25, No. 10, Oct. 2007, pp. 1171-1176.

Akbar, et al., "A compact vocabulary of paratope-epitope interactions enables predictability of antibody-antigen binding," Cell Reports 34, 108856, Mar. 2021, 21 pages.

Vajda, et al., "Progress toward improved understanding of antibody maturation," Current Opinion in Structural Biology 2021, 67:226-231.

Marks, et al., "How repertoire data are changing antibody science," J. Biol. Chern. (2020) 295(29), 9823-9837.

George, et al., "Differential Effects of Anti-$\beta_2$-Glycoprotein I Antibodies on Endothelial Cells and on the Manifestations of Experimental Antiphospholipid Syndrome," Circulation 1998; 97; 900-906.

* cited by examiner

Figure 1

```
16H11    1 QVQLHQSGAELVKPGASVKISCKGSGYDFSNFWMNWVKQRPGKGLEWIGQIYPGDGEIKYNGKFKGKATLTADESSSTAYIHLSSL
2G12     1 QVQLQQPGAELVKPGASVKLSCKASGYTFTSYWMQWVKQRPGQGLEWIGEIDPSVSYTEYNQKFKGKATLTVDTSSSTAYMQLSSL
5D1      1 QVQLQQPGAELVKPGASVKMSCKASGYTFTSSWITWVKDRPGQGLEWIGDIYPGNGNTNYNEKFKSKATLTVDTSSNTVYMQLSSL
8A2      1 QVQLKESGPGLVAPSQSLSITCTVSGFSLITTYGVDWVRQFPGKGLEWLGVIWGGGNTNYNSALMSRLSISKDTSKSQVFLKMNSL
9D4      1 QVTLKESGPGILQPSQTLSLTCSFSGFSLSTFGMGVGWIRQPSGKGLEWLAHIWDDDKYYHPALKSRLTISKDTSNNQVFLKIANV
13D2     1 DVQLQESGPGMVKPSQSLSLLTCTVTGYSITSDYDWHWIRHFPGNKLEWMGYISYSGSTKYNPSLKSRISITHDTSKNHFFLKLNSV
5215-2   1 DVQLQESGPGLVKPSQSLSLLTCTVTGYSITSDYVWTWIRQFPGNKLEWMGYIITYSDSTNYNPSLKSRLSITRDTSKNQFFLQLSSV
5G10     1 EVKLEESGGGLVQPGGSMKVSCVASGFTFSNYWMNWVRQSPEKGLEWVAQIRLKSDNYATHYAESVKGRFTISRDDSKSSVYLQMNNL
9H11     1 EVQLQQSGPELVKPGDSVKISCKASGYTFTDYYINWVKQSHGKSLEWIGRIIPYNGDTFYNQKFKDKATLTVDKSSNTAHLELRSL
10E11    1 EVQLQQSGPELVKPGASVKIPCKASGYTFTDYNMDWVKQSHEKSLEWIGDIDPHNGVTLYNQKFKDKATLTIDKSSNTAYMELRSL
4B12     1 EFQLQQSGPEMVKPGASVKMSCKASGDSFTDYKINWVKQNNGKSLEWIGVINPDSGTTSYNQIFEGKATLTVDQSSSTAYMQVNRL
3F1      1 EVQLQQSGAELVKPGASVKLSCTVSGENFKDTYIHWVKQRPEQGLEWIGRIDPANGNTKYASKFQDKATITADTSSNTVYMQLSSL
5215-13  1 EVQLQQSGAELVKSGASVKLSCTASGFNIKDTYMHWVKQRPEKGLEWIGWIDPADGHTKYDPKFQGKATITADTSSNTAYLHLSSL

16H11   87 TSEDSAVYFCARDDYLRAMDYWGQGTSVTVSS  (SEQ ID NO:1)
2G12    87 TSEDSAVYFCARWSKDYYGMDYWGQGTSVTVSS (SEQ ID NO:2)
5D1     87 TSEDSAVHYCARDGRGYFDYWGPGTTLTVSS   (SEQ ID NO:3)
8A2     86 QTDDTAMYYCAKHKGTSHAMEYWGQGTSVTVSS (SEQ ID NO:4)
9D4     88 DTAETATFYCARVERGYPLDHWGQGTTLRVSS  (SEQ ID NO:5)
13D2    87 TAEDTATYYCARENDFPGFWYFDVWGTGTTVTVSS (SEQ ID NO:6)
5215-2  87 TTEDTATYFCARSLTGNYFDYWGQGTTLTVSS  (SEQ ID NO:7)
5G10    89 RAEDTGIYYCTEGDYDIFAYWGQGTTLTVSA   (SEQ ID NO:8)
9H11    87 TSEDSAVYYCARPERYWYFDAWGTGTTVTVSS  (SEQ ID NO:9)
10E11   87 TSEDSVVYYCAGPRIGGDYDGGSWLAYWGQGTLVTVSA (SEQ ID NO:10)
4B12    87 TSEDSAVYYCALTGSTYWGQGTLVTVSA      (SEQ ID NO:11)
3F1     87 TSEDSAVYYCTTWDDYSFYAMDYWGQGTSVTVSS (SEQ ID NO:12)
5215-13 87 TSEDTAVYYCTRGWDGYYFDCWGQGTTLTVSS  (SEQ ID NO:13)
5215-9  87 TSEDAAVYYCPRGGSSPYFDYWGQGTTLTVSS  (SEQ ID NO:14)
```

Figure 2

```
16H11   1 QVQLHQSGAELVKPGASVKISCKGSGYDFSNFWMNWVKQRPGKGLEWIGQIYPGDGETKYNGKFKGKATLTADESSSTAYIHLSSL
2G12    1 QVQLQQPGAELVKPGASVKLSCKASGYTFTSYWMQWVKQRPGQGLEWIGEIDPSVSYTEYNQKFKGKATLTVDTSSSTAYMQLSSL
5D1     1 QVQLQQPGAELVKPGASVKMSCKASGYTFTSSWITWVKDRPGQGLEWIGDIYPGNGNTNYNEKFKSKATLTVDTSSNTVYMQLSSL
8A2     1 QVQLKESGPGLVAPSQSLSITCTVSGFSLTTYGVDWVRQFPGKGLEWLGVIWGGGNTNYNSALMSRLSISKDTSKSQVFLKMNSL
9D4     1 QVTLKESGPGILQPSQTLSLTCSFSGFSLSTFGMGVGWIRQPSGKGLEWLAHIWWDDDKYYHPALKSRLTISKDTSNNQVFLKIANV
13D2    1 DVQLQESGPGMVKPSQSLSLLTCTVTGYSITSDYDWHWIRHFPGNKLEWMGYISYSGSTKYNPSLKSRISITHDTSKNHFFLKLNSV
5215-2  1 DVQLQESGPGLVKPSQSLSLLTCTVTGYSITSDYVWTWIRQFPGNKLEWMGYIITYSDSTNYNPSLKSRLSITRDTSKNQFFLQLSSV
5G10    1 EVKLEESGGGLVQPGGSMKVSCVASGFTFSNYWMNWVRQSPEKGLEWVAQIRLKSDNYATHYAESVKGRFTISRDDSKSSVYLQMNNL
9H11    1 EVQLQQSGPELVKPGASVKLSCKASGYTFTFDYYINWVKQSHGKSLEWIGDNNPNNGASYNQSFKGKATMTVDQSSRTAYLELRSL
10E11   1 EVQLQQSGPELVKPGDSVKISCKASGYSSTGYFMNWVMQSHGKSLEWIGRIIPYNGDTFYNQKFKDKATLTVDKSSNTAHLELRSL
4B12    1 EVQLQQSGPELVKPGASVKIPCKASGYTFTDYNMDWVKQSHEKSLEWIGDIDPHNGVTLYNQKFKDKATLTIDKSSNTAYMELRSL
3F1     1 EFQLQQSGPEMVKPGASVKMSCKASGDSFTDYKINWVKQNNGKSLEWIGVINPDSGTTSYNQIFEGKATLTVDQSSSTAYMQVNRL
5215-13 1 EVQLQQSGAELVKPGASVKLSCTVSGFNFKDTYIHWVKQRPEQGLEWIGRIDPANGNTKYASKFQDKATTADTSSNTVYMQLSSL
5215-9  1 EVQLQQSGAELVKSGASVKLSCTASGFNIKDTYMHWVKQRPEKGLEWIGWIDPADGHTKYDPKFQGKATTTADTSSNTAYLHLSSL

16H11  87 TSEDSAVYFCARDDYLRAMDYWGQTSVTVSS (SEQ ID NO:1)
2G12   87 TSEDSAVYFCARWSKDYYGMDYWGQGTSVTVSS (SEQ ID NO:2)
5D1    87 TSEDSAVHYCARDGRGYFDYWGPGTTLTVSS (SEQ ID NO:3)
8A2    86 QTDDTAMYYCAKHKGTSHAMEYWGQGTSVTVSS (SEQ ID NO:4)
9D4    88 DTAETATFYCARVERGYPLDHWGQGTTLRVSS (SEQ ID NO:5)
13D2   87 TAEDTATYYCARENDFPGFWYFDVWGTGTTVTVSS (SEQ ID NO:6)
5215-2 87 TTEDTATYFCARSLTGNYFDYWGQGTTLTVSS (SEQ ID NO:7)
5G10   89 RAEDTGIYYCTEGDYDIFAYWGQGTTLVTVSA (SEQ ID NO:8)
9H11   87 TSEDSAVYYCARPERYWYFDAWGTGTTVTVSS (SEQ ID NO:9)
10E11  87 TSEDSVVYYCAGPRIGGDYDGGSWLAYWGQGTTVTVSA (SEQ ID NO:10)
4B12   87 TSEDSAVYYCALTGSTYWGQGTTLVTVSA (SEQ ID NO:11)
3F1    87 TSEDTAVYYCTTWDDYSFYAMDYWGQGTTLTVSS (SEQ ID NO:12)
5215-13 87 TSEDTAVYYCTRGWDGYYFDCWGQGTTLTVSS (SEQ ID NO:13)
5215-9 87 TSEDAAVYYCPRGGSSPYFDYWGQGTTLTVSS (SEQ ID NO:14)
```

Figure 3

```
16H11   1  DIQMTQSPASLSASVGETVTITCRASGNIHNYLAWFQQKQGKSPHFLVYSAKALADGVPSRFSGSGSGTQYSLK
9D4     1  DIVLTQSPASLAVSLGQRATISCRASQSVSSSYSYMHWYQQKPGQPPKLLIKYASNLKSGVPARFSGSGSGTDFTLT
SL2     1  VIVLTQSPASLEVSLGQRATISCRASQSVRISSYSYMNWYQQKPGQPPKLLIKYASNLESGVPARFSGSGSGTDFTLN
SL13    1  DIVLTQSPASLVVSLGLRATISCRASQSVSTSSHSYLHWYQQKPGQPPKLLIKYASNLASGVPARFSGSGSGADFTLN
SL9     1  DIVLTQSPASLTISLGQRATISCRASQSVSTSTSYIHWYQQKPGQPPKLLIKYASNLASGVPARFSGSGSGTDFSLS
8A2     1  QIVLTQSPAIMSASPGEKVTMTCSASSRVIFMYWYQQKPGSSPRLLIYDTSNLASGVPVRFSGGGSGTSYSLT
2G12    1  DIVLTQSHKFMSTSVGDRVTITCKASQDVSTAVAWYQQKPGQSPKLLIYWTSTRHTGVPDRFTGSGSGTDHTLT
10E11   1  DIVMTQSQKFMSTTVGDRVSITCKASQNVGTAVAWYQQKPGHSPKLLIYSASNRYTGVPDRFTGSGYGTDFTLT
4B12    1  DIVMTQSQKFMSTSVGDRVSVTCKASQNVGTNVAWYQQKPGQSPKAVIYSASYRNSGVPDRFTGSGSGTDFTLT
13D2    1  DIVMSQSPSSQVVSVGEKVTVTCTSSQSLLYGTNQKNYLAWYQQKPGQSPKLLIYWASIRESGVPDRFTGSGSGTDFTLT
3F1     1  DVLMTQTPLSLPVSLGDQASISCRSSQNIVHSNGNTYLEWFLQKPGQSPKLLIYKVSNRFSGVPDRFSGSGSGADYSLT
5D1     1  DIQMTQTTSSLSASLGDRVTIICRASQDISNFLNWYQQKPDGTVKLLMYDTSILQSGVPSRFSGRGSGADYSLT
5G10    1  DIQMTQTTSSLSASLGDRVTISCSASQGITNYLNWYQQKPDGTVKLLIYYTSILHSGVPSRFSGSGSGTDYSLT
9H11    1  DIVLTQSPVTLSVTPGDSVSLSCRASQSIRNNLHWYQQKSHESPRLLINYASQSISGIPSRFSGSGSGTDFILS

16H11  75  INSLQPEDFGTYYCQHFWSSPYTFGGGTKLEIK    (SEQ ID NO:15)
9D4    79  IHPVEEEDTATYYCQHSWEIPPTFGGGTKLEIK    (SEQ ID NO:19)
SL2    79  IHPVEEEDTATYYCQHSWKIPTFGGGTKLEIK.    (SEQ ID NO:20)
SL13   79  IHPVEEEDTATYYCQHSWEIPYTFGGGTKLEIK    (SEQ ID NO:21)
SL9    79  IHPMEEEDTATYYCQHSWKIPFTFGSGTKLEIK    (SEQ ID NO:22)
8A2    74  ISRMEAEDAATYYCQQWSSYPPTFGAGTKLELK    (SEQ ID NO:18)
2G12   75  ISSVQAEDLALYYCHQQYSTPPTFGGGTKLEIK    (SEQ ID NO:16)
10E11  75  ISNMQSEDLADYFCQQYNSYPLTFGAGTKLELK    (SEQ ID NO:23)
4B12   75  ISNVQSEDLTEYFCQQYNNYPYTFGGGTKLEIK    (SEQ ID NO:25)
13D2   81  ISSVKAEDLAVYYCQQYYSYPLTFGAGTKLELK    (SEQ ID NO:28)
3F1    80  ISRVEAEDLGVYYCFQGSHIPWTFGGGTKLEIK    (SEQ ID NO:24)
5D1    75  INNLEQEDLATYFCQQGKTLPYTFGGGTKLEIK    (SEQ ID NO:17)
5G10   75  ISNLEPEDIATYYCQQYSKPPYTFGGGTKLEIK    (SEQ ID NO:26)
9H11   75  INSVETEDFGMYFCQQSNNWPRTFGGGTLLQIKR   (SEQ ID NO:27)
```

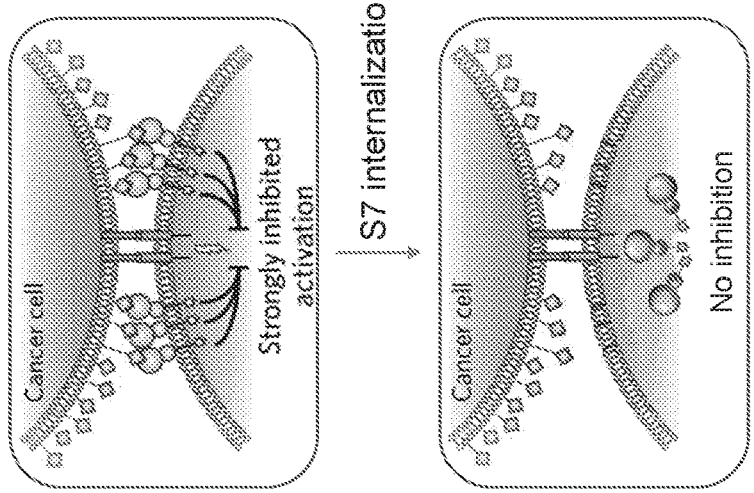
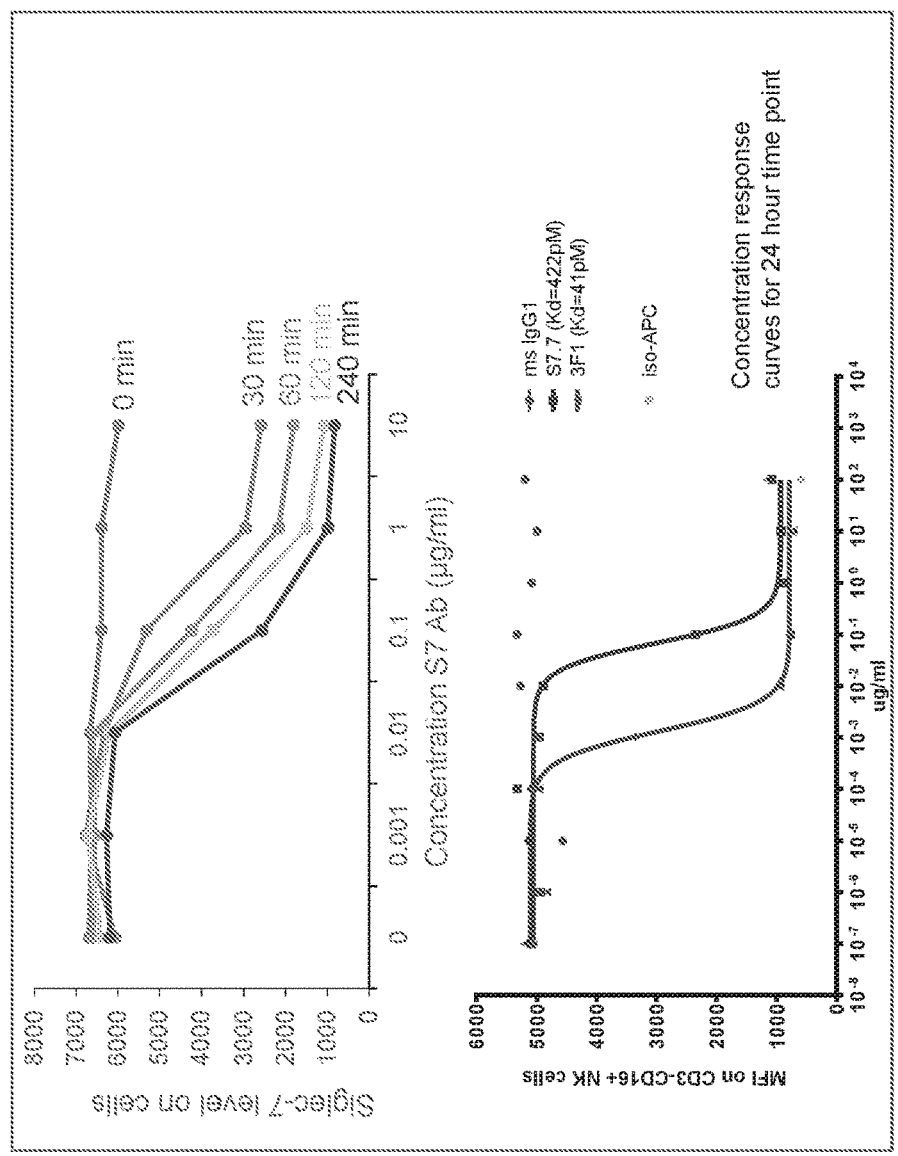
Figure 10

Figure 11
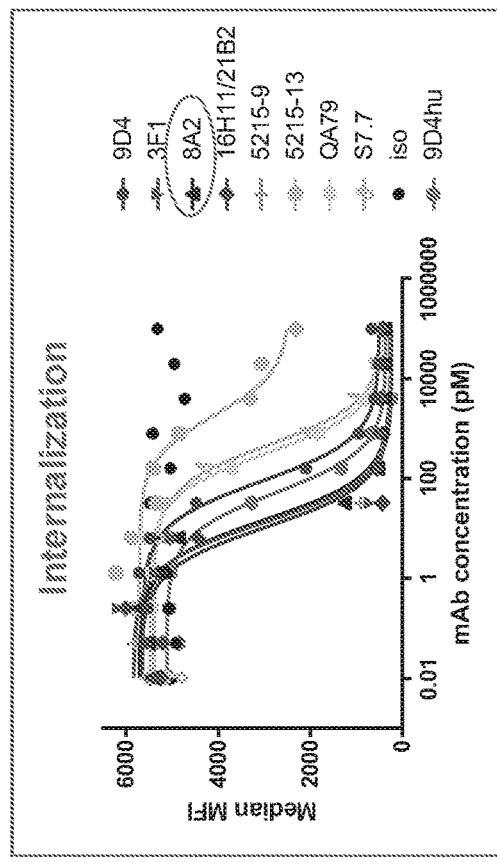
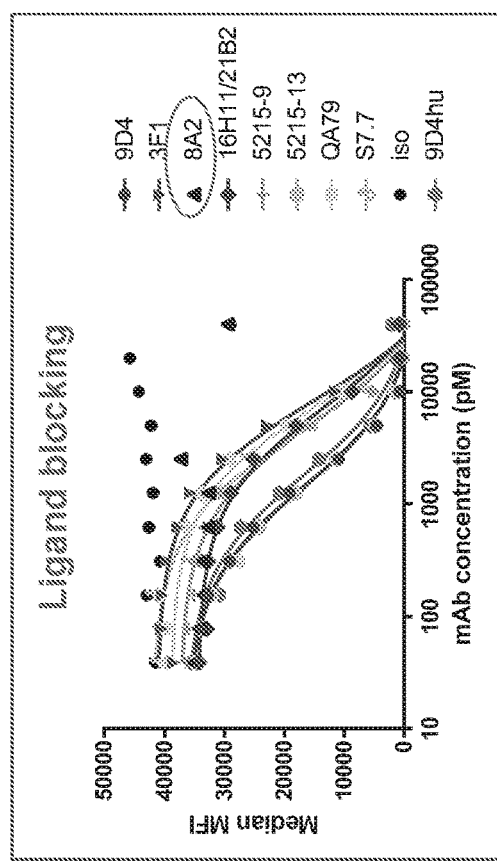

SEQUENCE LISTING

<160> NUMBER OF SEQ ID NOS: 113

<210> SEQ ID NO 1
<211> LENGTH: 118
<212> TYPE: PRT
<213> ORGANISM: Mus musculus

<400> SEQUENCE: 1

Gln Val Gln Leu His Gln Ser Gly Ala Glu Leu Val Lys Pro Gly Ala
1               5                   10                  15

Ser Val Lys Ile Ser Cys Lys Gly Ser Gly Tyr Asp Phe Ser Asn Phe
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Glu Ile Lys Tyr Asn Gly Lys Phe
    50                  55                  60

Lys Gly Lys Ala Thr Leu Thr Ala Asp Glu Ser Ser Thr Ala Tyr
65                  70                  75                  80

Ile His Leu Ser Ser Leu Thr Ser Glu Asp Ser Ala Val Tyr Phe Cys
                85                  90                  95

Ala Arg Asp Asp Tyr Leu Arg Ala Met Asp Tyr Trp Gly Gln Gly Thr
            100                 105                 110

Ser Val Thr Val Ser Ser
        115

<210> SEQ ID NO 2
<211> LENGTH: 119
<212> TYPE: PRT
<213> ORGANISM: Mus musculus

<400> SEQUENCE: 2

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asp Pro Ser Val Ser Tyr Thr Glu Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Trp Ser Lys Asp Tyr Tyr Gly Met Asp Tyr Trp Gly Gln Gly
            100                 105                 110

Thr Ser Val Thr Val Ser Ser
        115

<210> SEQ ID NO 3
<211> LENGTH: 117
<212> TYPE: PRT
<213> ORGANISM: Mus musculus

<400> SEQUENCE: 3

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Ser
            20                  25                  30

```
Trp Ile Thr Trp Val Lys Asp Arg Pro Gly Gln Gly Leu Glu Trp Ile
            35                  40                  45

Gly Asp Ile Tyr Pro Gly Asn Gly Asn Thr Asn Tyr Asn Glu Lys Phe
     50                  55                  60

Lys Ser Lys Ala Thr Leu Thr Val Asp Thr Ser Ser Asn Thr Val Tyr
 65              70                  75                      80

Met Gln Leu Ser Ser Leu Thr Ser Glu Asp Ser Ala Val His Tyr Cys
                 85                  90                  95

Ala Arg Asp Gly Arg Gly Tyr Phe Asp Tyr Trp Gly Pro Gly Thr Thr
            100                 105                 110

Leu Thr Val Ser Ser
            115

<210> SEQ ID NO 4
<211> LENGTH: 118
<212> TYPE: PRT
<213> ORGANISM: Mus musculus

<400> SEQUENCE: 4

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
             20                  25                  30

Gly Val Asp Trp Val Arg Gln Phe Pro Gly Lys Gly Leu Glu Trp Leu
            35                  40                  45

Gly Val Ile Trp Gly Gly Asn Thr Asn Tyr Asn Ser Ala Leu Met Ser
     50                  55                  60

Ser Arg Leu Ser Ile Ser Lys Asp Thr Ser Lys Ser Gln Val Phe Leu
 65              70                  75                      80

Lys Met Asn Ser Leu Gln Thr Asp Asp Thr Ala Met Tyr Tyr Cys Ala
                 85                  90                  95

Lys His Lys Gly Thr Ser His Ala Met Glu Tyr Trp Gly Gln Gly Thr
            100                 105                 110

Ser Val Thr Val Ser Ser
            115

<210> SEQ ID NO 5
<211> LENGTH: 119
<212> TYPE: PRT
<213> ORGANISM: Mus musculus

<400> SEQUENCE: 5

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
             20                  25                  30

Gly Met Gly Val Gly Trp Ile Arg Gln Pro Ser Gly Lys Gly Leu Glu
            35                  40                  45

Trp Leu Ala His Ile Trp Trp Asp Asp Lys Tyr Tyr His Pro Ala
     50                  55                  60

Leu Lys Ser Arg Leu Thr Ile Ser Lys Asp Thr Ser Asn Asn Gln Val
 65              70                  75                      80

Phe Leu Lys Ile Ala Asn Val Asp Thr Ala Glu Thr Ala Thr Phe Tyr
                 85                  90                  95

Cys Ala Arg Val Glu Arg Gly Tyr Pro Leu Asp His Trp Gly Gln Gly
            100                 105                 110
```

-continued

Thr Thr Leu Arg Val Ser Ser
        115

<210> SEQ ID NO 6
<211> LENGTH: 121
<212> TYPE: PRT
<213> ORGANISM: Mus musculus

<400> SEQUENCE: 6

Asp Val Gln Leu Gln Glu Ser Gly Pro Gly Met Val Lys Pro Ser Gln
1               5                   10                  15

Ser Leu Ser Leu Thr Cys Thr Val Thr Gly Tyr Ser Ile Thr Ser Asp
            20                  25                  30

Tyr Asp Trp His Trp Ile Arg His Phe Pro Gly Asn Lys Leu Glu Trp
        35                  40                  45

Met Gly Tyr Ile Ser Tyr Ser Gly Ser Thr Lys Tyr Asn Pro Ser Leu
    50                  55                  60

Lys Ser Arg Ile Ser Ile Thr His Asp Thr Ser Lys Asn His Phe Phe
65                  70                  75                  80

Leu Lys Leu Asn Ser Val Thr Ala Glu Asp Thr Ala Thr Tyr Tyr Cys
                85                  90                  95

Ala Arg Glu Asn Asp Phe Pro Gly Phe Trp Tyr Phe Asp Val Trp Gly
            100                 105                 110

Thr Gly Thr Thr Val Thr Val Ser Ser
        115                 120

<210> SEQ ID NO 7
<211> LENGTH: 118
<212> TYPE: PRT
<213> ORGANISM: Mus musculus

<400> SEQUENCE: 7

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Val Trp Thr Trp Ile Arg Gln Phe Pro Gly Asn Lys Leu Glu Trp
        35                  40                  45

Met Gly Tyr Ile Thr Tyr Ser Asp Ser Thr Asn Tyr Asn Pro Ser Leu
    50                  55                  60

Lys Ser Arg Leu Ser Ile Thr Arg Asp Thr Ser Lys Asn Gln Phe Phe
65                  70                  75                  80

Leu Gln Leu Ser Ser Val Thr Thr Glu Asp Thr Ala Thr Tyr Phe Cys
                85                  90                  95

Ala Arg Ser Leu Thr Gly Asn Tyr Phe Asp Tyr Trp Gly Gln Gly Thr
            100                 105                 110

Thr Leu Thr Val Ser Ser
        115

<210> SEQ ID NO 8
<211> LENGTH: 119
<212> TYPE: PRT
<213> ORGANISM: Mus musculus

<400> SEQUENCE: 8

Glu Val Lys Leu Glu Glu Ser Gly Gly Gly Leu Val Gln Pro Gly Gly
1               5                   10                  15

```
Ser Met Lys Val Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
                35                  40                  45

Ala Gln Ile Arg Leu Lys Ser Asp Asn Tyr Ala Thr His Tyr Ala Glu
 50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Glu Gly Asp Tyr Asp Ile Phe Ala Tyr Trp Gly Gln Gly
            100                 105                 110

Thr Leu Val Thr Val Ser Ala
            115
```

<210> SEQ ID NO 9
<211> LENGTH: 118
<212> TYPE: PRT
<213> ORGANISM: Mus musculus

<400> SEQUENCE: 9

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Ser His Gly Lys Ser Leu Glu Trp Ile
                35                  40                  45

Gly Asp Asn Asn Pro Asn Asn Gly Gly Ala Ser Tyr Asn Gln Ser Phe
 50                  55                  60

Lys Gly Lys Ala Thr Met Thr Val Asp Gln Ser Ser Arg Thr Ala Tyr
65                  70                  75                  80

Leu Glu Leu Arg Ser Leu Thr Ser Glu Asp Ser Ala Val Tyr Tyr Cys
                85                  90                  95

Ala Arg Pro Glu Arg Tyr Trp Tyr Phe Asp Ala Trp Gly Thr Gly Thr
            100                 105                 110

Thr Val Thr Val Ser Ser
            115
```

<210> SEQ ID NO 10
<211> LENGTH: 124
<212> TYPE: PRT
<213> ORGANISM: Mus musculus

<400> SEQUENCE: 10

```
Glu Val Gln Leu Gln Gln Ser Gly Pro Glu Leu Val Lys Pro Gly Asp
1               5                   10                  15

Ser Val Lys Ile Ser Cys Lys Ala Ser Gly Tyr Ser Ser Thr Gly Tyr
            20                  25                  30

Phe Met Asn Trp Val Met Gln Ser His Gly Lys Ser Leu Glu Trp Ile
                35                  40                  45

Gly Arg Ile Ile Pro Tyr Asn Gly Asp Thr Phe Tyr Asn Gln Lys Phe
 50                  55                  60

Lys Asp Lys Ala Thr Leu Thr Val Asp Lys Ser Ser Asn Thr Ala His
65                  70                  75                  80

Leu Glu Leu Arg Ser Leu Thr Ser Glu Asp Ser Val Val Tyr Tyr Cys
                85                  90                  95
```

Ala Gly Pro Arg Ile Gly Gly Asp Tyr Asp Gly Ser Trp Leu Ala
            100                 105                 110

Tyr Trp Gly Gln Gly Thr Leu Val Thr Val Ser Ala
        115                 120

<210> SEQ ID NO 11
<211> LENGTH: 114
<212> TYPE: PRT
<213> ORGANISM: Mus musculus

<400> SEQUENCE: 11

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Glu Lys Ser Leu Glu Trp Ile
        35                  40                  45

Gly Asp Ile Asp Pro His Asn Gly Val Thr Leu Tyr Asn Gln Lys Phe
    50                  55                  60

Lys Asp Lys Ala Thr Leu Thr Ile Asp Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Ala Leu Thr Gly Ser Thr Tyr Trp Gly Gln Gly Thr Leu Val Thr Val
            100                 105                 110

Ser Ala

<210> SEQ ID NO 12
<211> LENGTH: 120
<212> TYPE: PRT
<213> ORGANISM: Mus musculus

<400> SEQUENCE: 12

Glu Phe Gln Leu Gln Gln Ser Gly Pro Glu Met Val Lys Pro Gly Ala
1               5                   10                  15

Ser Val Lys Met Ser Cys Lys Ala Ser Gly Asp Ser Phe Thr Asp Tyr
            20                  25                  30

Lys Ile Asn Trp Val Lys Gln Asn Gly Lys Ser Leu Glu Trp Ile
        35                  40                  45

Gly Val Ile Asn Pro Asp Ser Gly Thr Thr Ser Tyr Asn Gln Ile Phe
    50                  55                  60

Glu Gly Lys Ala Thr Leu Thr Val Asp Gln Ser Ser Ser Thr Ala Tyr
65                  70                  75                  80

Met Gln Val Asn Arg Leu Thr Ser Glu Asp Ser Ala Val Tyr Tyr Cys
                85                  90                  95

Thr Thr Trp Asp Asp Tyr Ser Phe Tyr Ala Met Asp Tyr Trp Gly Gln
            100                 105                 110

Gly Thr Ser Val Thr Val Ser Ser
        115                 120

<210> SEQ ID NO 13
<211> LENGTH: 118
<212> TYPE: PRT
<213> ORGANISM: Mus musculus

<400> SEQUENCE: 13

Glu Val Gln Leu Gln Gln Ser Gly Ala Glu Leu Val Lys Pro Gly Ala
1               5                   10                  15

```
Ser Val Lys Leu Ser Cys Thr Val Ser Gly Phe Asn Phe Lys Asp Thr
            20                  25                  30

Tyr Ile His Trp Val Lys Gln Arg Pro Glu Gln Gly Leu Glu Trp Ile
            35                  40                  45

Gly Arg Ile Asp Pro Ala Asn Gly Asn Thr Lys Tyr Ala Ser Lys Phe
50                      55                  60

Gln Asp Lys Ala Thr Ile Thr Ala Asp Thr Ser Ser Asn Thr Val Tyr
65                  70                  75                  80

Met Gln Leu Ser Ser Leu Thr Ser Glu Asp Thr Ala Val Tyr Tyr Cys
                85                  90                  95

Thr Arg Gly Trp Asp Gly Tyr Tyr Phe Asp Cys Trp Gly Gln Gly Thr
                100                 105                 110

Thr Leu Thr Val Ser Ser
            115

<210> SEQ ID NO 14
<211> LENGTH: 118
<212> TYPE: PRT
<213> ORGANISM: Mus musculus

<400> SEQUENCE: 14

Glu Val Gln Leu Gln Gln Ser Gly Ala Glu Leu Val Lys Ser Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Lys Gly Leu Glu Trp Ile
            35                  40                  45

Gly Trp Ile Asp Pro Ala Asp Gly His Thr Lys Tyr Asp Pro Lys Phe
50                      55                  60

Gln Gly Lys Ala Thr Ile Thr Ala Asp Thr Ser Ser Asn Thr Ala Tyr
65                  70                  75                  80

Leu His Leu Ser Ser Leu Thr Ser Glu Asp Ala Ala Val Tyr Tyr Cys
                85                  90                  95

Pro Arg Gly Gly Ser Ser Pro Tyr Phe Asp Tyr Trp Gly Gln Gly Thr
                100                 105                 110

Thr Leu Thr Val Ser Ser
            115

<210> SEQ ID NO 15
<211> LENGTH: 107
<212> TYPE: PRT
<213> ORGANISM: Mus musculus

<400> SEQUENCE: 15

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Phe Gln Gln Lys Gln Gly Lys Ser Pro His Phe Leu Val
            35                  40                  45

Tyr Ser Ala Lys Ala Leu Ala Asp Gly Val Pro Ser Arg Phe Ser Gly
50                      55                  60

Ser Gly Ser Gly Thr Gln Tyr Ser Leu Lys Ile Asn Ser Leu Gln Pro
65                  70                  75                  80

Glu Asp Phe Gly Thr Tyr Tyr Cys Gln His Phe Trp Ser Ser Pro Tyr
                85                  90                  95
```

Thr Phe Gly Gly Gly Thr Lys Leu Glu Ile Lys
            100                 105

<210> SEQ ID NO 16
<211> LENGTH: 107
<212> TYPE: PRT
<213> ORGANISM: Mus musculus

<400> SEQUENCE: 16

Asp Ile Val Leu Thr Gln Ser His Lys Phe Met Ser Thr Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp His Thr Leu Thr Ile Ser Ser Val Gln Ala
65                  70                  75                  80

Glu Asp Leu Ala Leu Tyr Tyr Cys His Gln Gln Tyr Ser Thr Pro Pro
                85                  90                  95

Thr Phe Gly Gly Gly Thr Lys Leu Glu Ile Lys
            100                 105

<210> SEQ ID NO 17
<211> LENGTH: 107
<212> TYPE: PRT
<213> ORGANISM: Mus musculus

<400> SEQUENCE: 17

Asp Ile Gln Met Thr Gln Thr Thr Ser Ser Leu Ser Ala Ser Leu Gly
1               5                   10                  15

Asp Arg Val Thr Ile Ile Cys Arg Ala Ser Gln Asp Ile Ser Asn Phe
            20                  25                  30

Leu Asn Trp Tyr Gln Gln Lys Pro Asp Gly Thr Val Lys Leu Leu Met
        35                  40                  45

Tyr Asp Thr Ser Ile Leu Gln Ser Gly Val Pro Ser Arg Phe Ser Gly
    50                  55                  60

Arg Gly Ser Gly Ala Asp Tyr Ser Leu Thr Ile Asn Asn Leu Glu Gln
65                  70                  75                  80

Glu Asp Leu Ala Thr Tyr Phe Cys Gln Gln Gly Lys Thr Leu Pro Tyr
                85                  90                  95

Thr Phe Gly Gly Gly Thr Lys Leu Glu Ile Lys
            100                 105

<210> SEQ ID NO 18
<211> LENGTH: 106
<212> TYPE: PRT
<213> ORGANISM: Mus musculus

<400> SEQUENCE: 18

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Arg Val Ile Phe Met
            20                  25                  30

Tyr Trp Tyr Gln Gln Lys Pro Gly Ser Ser Pro Arg Leu Leu Ile Tyr
        35                  40                  45

```
Asp Thr Ser Asn Leu Ala Ser Gly Val Pro Val Arg Phe Ser Gly Gly
        50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Trp Ser Ser Tyr Pro Pro Thr
                 85                  90                  95

Phe Gly Ala Gly Thr Lys Leu Glu Leu Lys
            100                 105

<210> SEQ ID NO 19
<211> LENGTH: 111
<212> TYPE: PRT
<213> ORGANISM: Mus musculus

<400> SEQUENCE: 19

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Gln Ser Val Ser Ser Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Lys Ser Gly Val Pro Ala
 50                  55                  60

Arg Phe Ser Gly Ser Gly Ser Gly Thr Asp Phe Thr Leu Thr Ile His
 65                  70                  75                  80

Pro Val Glu Glu Glu Asp Thr Ala Thr Tyr Tyr Cys Gln His Ser Trp
                 85                  90                  95

Glu Ile Pro Pro Thr Phe Gly Gly Gly Thr Lys Leu Glu Ile Lys
            100                 105                 110

<210> SEQ ID NO 20
<211> LENGTH: 110
<212> TYPE: PRT
<213> ORGANISM: Mus musculus

<400> SEQUENCE: 20

Val Ile Val Leu Thr Gln Ser Pro Ala Ser Leu Glu Val Ser Leu Gly
 1               5                  10                  15

Gln Arg Ala Thr Ile Ser Cys Arg Ala Ser Gln Thr Val Arg Ile Ser
            20                  25                  30

Ser Tyr Ser Tyr Met Asn Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Thr Ala Thr Tyr Tyr Cys Gln His Ser Trp
                 85                  90                  95

Lys Ile Pro Thr Phe Gly Gly Gly Thr Lys Leu Glu Ile Lys
            100                 105                 110

<210> SEQ ID NO 21
<211> LENGTH: 111
<212> TYPE: PRT
<213> ORGANISM: Mus musculus

<400> SEQUENCE: 21

Asp Ile Val Leu Thr Gln Ser Pro Ala Ser Leu Val Val Ser Leu Gly
```

```
                1               5                   10                  15
Leu Arg Ala Thr Ile Ser Cys Arg Ala Ser Gln Ser Val Ser Thr Ser
                20                  25                  30

Ser His Ser Tyr Leu His Trp Tyr Gln Gln Lys Pro Gly Gln Pro Pro
            35                  40                  45

Lys Leu Leu Ile Lys Tyr Ala Ser Asn Leu Ala Ser Gly Val Pro Ala
        50                  55                  60

Arg Phe Ser Gly Ser Gly Ser Gly Ala Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
                100                 105                 110

<210> SEQ ID NO 22
<211> LENGTH: 111
<212> TYPE: PRT
<213> ORGANISM: Mus musculus

<400> SEQUENCE: 22

Asp Ile Val Leu Thr Gln Ser Pro Ala Ser Leu Thr Ile Ser Leu Gly
1               5                   10                  15

Gln Arg Ala Thr Ile Ser Cys Arg Ala Ser Gln Ser Val Ser Thr Ser
                20                  25                  30

Thr Tyr Ser Tyr Ile His Trp Tyr Gln Gln Lys Pro Gly Gln Pro Pro
            35                  40                  45

Lys Leu Leu Ile Lys Tyr Ala Ser Asn Leu Ala Ser Gly Val Pro Ala
        50                  55                  60

Arg Phe Ser Gly Ser Gly Ser Gly Thr Asp Phe Ser Leu Ser Ile His
65                  70                  75                  80

Pro Met Glu Glu Glu Asp Thr Ala Thr Tyr Tyr Cys Gln His Ser Trp
                85                  90                  95

Lys Ile Pro Phe Thr Phe Gly Ser Gly Thr Lys Leu Glu Ile Lys
                100                 105                 110

<210> SEQ ID NO 23
<211> LENGTH: 107
<212> TYPE: PRT
<213> ORGANISM: Mus musculus

<400> SEQUENCE: 23

Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Val Gly Thr Ala
                20                  25                  30

Val Ala Trp Tyr Gln Gln Lys Pro Gly His Ser Pro Lys Leu Leu Ile
            35                  40                  45

Tyr Ser Ala Ser Asn Arg Tyr Thr Gly Val Pro Asp Arg Phe Thr Gly
        50                  55                  60

Ser Gly Tyr Gly Thr Asp Phe Thr Leu Thr Ile Ser Asn Met Gln Ser
65                  70                  75                  80

Glu Asp Leu Ala Asp Tyr Phe Cys Gln Gln Tyr Asn Ser Tyr Pro Leu
                85                  90                  95

Thr Phe Gly Ala Gly Thr Lys Leu Glu Leu Lys
                100                 105
```

<210> SEQ ID NO 24
<211> LENGTH: 112
<212> TYPE: PRT
<213> ORGANISM: Mus musculus

<400> SEQUENCE: 24

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ile Pro Trp Thr Phe Gly Gly Gly Thr Lys Leu Glu Ile Lys
            100                 105                 110

<210> SEQ ID NO 25
<211> LENGTH: 107
<212> TYPE: PRT
<213> ORGANISM: Mus musculus

<400> SEQUENCE: 25

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Val Ile
        35                  40                  45

Tyr Ser Ala Ser Tyr Arg Asn Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Thr Glu Tyr Phe Cys Gln Gln Tyr Asn Asn Tyr Pro Tyr
                85                  90                  95

Thr Phe Gly Gly Gly Thr Lys Leu Glu Ile Lys
            100                 105

<210> SEQ ID NO 26
<211> LENGTH: 107
<212> TYPE: PRT
<213> ORGANISM: Mus musculus

<400> SEQUENCE: 26

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Thr Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

-continued

```
Glu Asp Ile Ala Thr Tyr Tyr Cys Gln Gln Tyr Ser Lys Pro Pro Tyr
                85                  90                  95

Thr Phe Gly Gly Gly Thr Lys Leu Glu Ile Lys
            100                 105

<210> SEQ ID NO 27
<211> LENGTH: 108
<212> TYPE: PRT
<213> ORGANISM: Mus musculus

<400> SEQUENCE: 27

Asp Ile Val Leu Thr Gln Ser Pro Val Thr Leu Ser Val Thr Pro Gly
1               5                   10                  15

Asp Ser Val Ser Leu Ser Cys Arg Ala Ser Gln Ser Ile Arg Asn Asn
            20                  25                  30

Leu His Trp Tyr Gln Gln Lys Ser His Glu Ser Pro Arg Leu Leu Ile
        35                  40                  45

Asn Tyr Ala Ser Gln Ser Ile Ser Gly Ile Pro Ser Arg Phe Ser Gly
    50                  55                  60

Ser Gly Ser Gly Thr Asp Phe Ile Leu Ser Ile Asn Ser Val Glu Thr
65                  70                  75                  80

Glu Asp Phe Gly Met Tyr Phe Cys Gln Gln Ser Asn Asn Trp Pro Arg
                85                  90                  95

Thr Phe Gly Gly Gly Thr Leu Leu Gln Ile Lys Arg
            100                 105

<210> SEQ ID NO 28
<211> LENGTH: 113
<212> TYPE: PRT
<213> ORGANISM: Mus musculus

<400> SEQUENCE: 28

Asp Ile Val Met Ser Gln Ser Pro Ser Ser Gln Val Val Ser Val Gly
1               5                   10                  15

Glu Lys Val Thr Val Thr Cys Thr Ser Ser Gln Ser Leu Leu Tyr Gly
            20                  25                  30

Thr Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ile Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 29
<211> LENGTH: 118
<212> TYPE: PRT
<213> ORGANISM: Artificial Sequence
<220> FEATURE:
<223> OTHER INFORMATION: Synthetic construct

<400> SEQUENCE: 29

Gln Val Gln Leu Val Gln Ser Gly Ala Glu Val Lys Lys Pro Gly Ser
1               5                   10                  15
```

Ser Val Lys Val Ser Cys Lys Ala Ser Gly Tyr Asp Phe Ser Asn Phe
            20                  25                  30

Trp Ile Ser Trp Val Arg Gln Ala Pro Gly Gln Gly Leu Glu Trp Met
        35                  40                  45

Gly Gly Ile Tyr Pro Gly Asp Gly Glu Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Tyr Trp Gly Gln Gly Thr
            100                 105                 110

Leu Val Thr Val Ser Ser
            115

<210> SEQ ID NO 30
<211> LENGTH: 118
<212> TYPE: PRT
<213> ORGANISM: Artificial Sequence
<220> FEATURE:
<223> OTHER INFORMATION: Synthetic construct

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asn Phe
            20                  25                  30

Trp Ile Ser Trp Val Arg Gln Ala Pro Gly Gln Gly Leu Glu Trp Met
        35                  40                  45

Gly Gly Ile Tyr Pro Gly Asp Gly Glu Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Tyr Trp Gly Gln Gly Thr
            100                 105                 110

Leu Val Thr Val Ser Ser
            115

<210> SEQ ID NO 31
<211> LENGTH: 118
<212> TYPE: PRT
<213> ORGANISM: Artificial Sequence
<220> FEATURE:
<223> OTHER INFORMATION: Synthetic construct

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Asp Phe Ser Asn Phe
            20                  25                  30

Trp Ile Ser Trp Val Arg Gln Ala Pro Gly Gln Gly Leu Glu Trp Met
        35                  40                  45

Gly Gly Ile Tyr Pro Gly Asp Gly Glu Ile Asn Tyr Ala Gln Lys Phe
    50                  55                  60

Gln Gly Arg Val Thr Ile Thr Ala Asp Glu Ser Thr Ser Thr Ala Tyr

```
                65                  70                  75                  80
Met Glu Leu Ser Ser Leu Arg Ser Glu Asp Thr Ala Val Tyr Tyr Cys
                    85                  90                  95

Ala Arg Asp Asp Tyr Leu Arg Ala Met Asp Tyr Trp Gly Gln Gly Thr
                100                 105                 110

Leu Val Thr Val Ser Ser
            115

<210> SEQ ID NO 32
<211> LENGTH: 118
<212> TYPE: PRT
<213> ORGANISM: Artificial Sequence
<220> FEATURE:
<223> OTHER INFORMATION: Synthetic construct

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
                20                  25                  30

Trp Ile Ser Trp Val Arg Gln Ala Pro Gly Gln Gly Leu Glu Trp Met
            35                  40                  45

Gly Gly Ile Ile Pro Gly Asp Gly Glu Ile Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Asp Asp Tyr Leu Arg Ala Met Asp Tyr Trp Gly Gln Gly Thr
                100                 105                 110

Leu Val Thr Val Ser Ser
            115

<210> SEQ ID NO 33
<211> LENGTH: 118
<212> TYPE: PRT
<213> ORGANISM: Artificial Sequence
<220> FEATURE:
<223> OTHER INFORMATION: Synthetic construct

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
                20                  25                  30

Trp Ile Ser Trp Val Arg Gln Ala Pro Gly Gln Gly Leu Glu Trp Met
            35                  40                  45

Gly Gly Ile Tyr Pro Ile Asp Gly Glu Ile Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Asp Asp Tyr Leu Arg Ala Met Asp Tyr Trp Gly Gln Gly Thr
                100                 105                 110

Leu Val Thr Val Ser Ser
            115
```

```
<210> SEQ ID NO 34
<211> LENGTH: 118
<212> TYPE: PRT
<213> ORGANISM: Artificial Sequence
<220> FEATURE:
<223> OTHER INFORMATION: Synthetic construct

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
                20                  25                  30

Trp Ile Ser Trp Val Arg Gln Ala Pro Gly Gln Gly Leu Glu Trp Met
            35                  40                  45

Gly Gly Ile Tyr Pro Gly Asp Gly Thr Ile Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Tyr Trp Gly Gln Gly Thr
            100                 105                 110

Leu Val Thr Val Ser Ser
        115

<210> SEQ ID NO 35
<211> LENGTH: 118
<212> TYPE: PRT
<213> ORGANISM: Artificial Sequence
<220> FEATURE:
<223> OTHER INFORMATION: Synthetic construct

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
                20                  25                  30

Trp Ile Ser Trp Val Arg Gln Ala Pro Gly Gln Gly Leu Glu Trp Met
            35                  40                  45

Gly Gly Ile Tyr Pro Gly Asp Gly Glu Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Tyr Trp Gly Gln Gly Thr
            100                 105                 110

Leu Val Thr Val Ser Ser
        115

<210> SEQ ID NO 36
<211> LENGTH: 118
<212> TYPE: PRT
<213> ORGANISM: Artificial Sequence
<220> FEATURE:
<223> OTHER INFORMATION: Synthetic construct

<400> SEQUENCE: 36

Gln Val Gln Leu Val Gln Ser Gly Ala Glu Val Lys Lys Pro Gly Ser
```

```
1               5                   10                  15
Ser Val Lys Val Ser Cys Lys Ala Ser Gly Tyr Asp Phe Ser Ser Tyr
            20                  25                  30

Ala Ile Ser Trp Val Arg Gln Ala Pro Gly Gln Gly Leu Glu Trp Met
            35                  40                  45

Gly Gly Ile Tyr Pro Gly Asp Gly Glu Ile Asn Tyr Ala Gln Lys Phe
            50                  55                  60

Gln Gly Arg Val Thr Ile Thr Ala Asp Glu Ser Thr Ser Thr Ala Tyr
65                      70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Tyr Trp Gly Gln Gly Thr
            100                 105                 110

Leu Val Thr Val Ser Ser
            115

<210> SEQ ID NO 37
<211> LENGTH: 118
<212> TYPE: PRT
<213> ORGANISM: Artificial Sequence
<220> FEATURE:
<223> OTHER INFORMATION: Synthetic construct

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Ser Phe
            20                  25                  30

Trp Ile Ser Trp Val Arg Gln Ala Pro Gly Gln Gly Leu Glu Trp Met
            35                  40                  45

Gly Gly Ile Tyr Pro Gly Asp Gly Glu Ile Asn Tyr Ala Gln Lys Phe
            50                  55                  60

Gln Gly Arg Val Thr Ile Thr Ala Asp Glu Ser Thr Ser Thr Ala Tyr
65                      70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Tyr Trp Gly Gln Gly Thr
            100                 105                 110

Leu Val Thr Val Ser Ser
            115

<210> SEQ ID NO 38
<211> LENGTH: 118
<212> TYPE: PRT
<213> ORGANISM: Artificial Sequence
<220> FEATURE:
<223> OTHER INFORMATION: Synthetic construct

<400> SEQUENCE: 38

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Ser Tyr
            20                  25                  30

Trp Ile Ser Trp Val Arg Gln Ala Pro Gly Gln Gly Leu Glu Trp Met
            35                  40                  45

Gly Gly Ile Tyr Pro Gly Asp Gly Glu Ile Asn Tyr Ala Gln Lys Phe
            50                  55                  60
```

-continued

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Asp Tyr Leu Arg Ala Met Asp Tyr Trp Gly Gln Gly Thr
            100                 105                 110

Leu Val Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: Synthetic construct

<400> SEQUENCE: 39

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Asp Phe Ser Asn Tyr
                 20                  25                  30

Ala Ile Ser Trp Val Arg Gln Ala Pro Gly Gln Gly Leu Glu Trp Met
             35                  40                  45

Gly Gly Ile Tyr Pro Gly Asp Gly Glu Ile Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Asp Tyr Leu Arg Ala Met Asp Tyr Trp Gly Gln Gly Thr
            100                 105                 110

Leu Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Synthetic construct

<400> SEQUENCE: 40

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Asp Phe Ser Asn Phe
                 20                  25                  30

Trp Ile Ser Trp Val Arg Gln Ala Pro Gly Gln Gly Leu Glu Trp Met
             35                  40                  45

Gly Gly Ile Tyr Pro Gly Phe Gly Glu Ile Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Asp Tyr Leu Arg Ala Met Asp Tyr Trp Gly Gln Gly Thr
            100                 105                 110

Leu Val Thr Val Ser Ser
        115
```

<210> SEQ ID NO 41
<211> LENGTH: 118
<212> TYPE: PRT
<213> ORGANISM: Artificial Sequence
<220> FEATURE:
<223> OTHER INFORMATION: Synthetic construct

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
            20                  25                  30

Trp Met Asn Trp Val Arg Gln Ala Pro Gly Gln Gly Leu Glu Trp Met
        35                  40                  45

Gly Gly Ile Tyr Pro Gly Asp Gly Glu Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Val Trp Gly Gln Gly Thr
            100                 105                 110

Met Val Thr Val Ser Ser
        115

<210> SEQ ID NO 42
<211> LENGTH: 118
<212> TYPE: PRT
<213> ORGANISM: Artificial Sequence
<220> FEATURE:
<223> OTHER INFORMATION: Synthetic construct

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
            20                  25                  30

Trp Met Asn Trp Val Arg Gln Ala Pro Gly Gln Gly Leu Glu Trp Met
        35                  40                  45

Gly Gly Ile Tyr Pro Gly Asp Gly Glu Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Ile Trp Gly Gln Gly Thr
            100                 105                 110

Met Val Thr Val Ser Ser
        115

<210> SEQ ID NO 43
<211> LENGTH: 118
<212> TYPE: PRT
<213> ORGANISM: Artificial Sequence
<220> FEATURE:
<223> OTHER INFORMATION: Synthetic construct

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Gly Ser Gly Tyr Asp Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Glu Ile Lys Tyr Asn Gln Lys Phe
    50                  55                  60

Gln Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
            85                  90                  95

Ala Arg Asp Asp Tyr Leu Arg Ala Met Asp Tyr Trp Gly Gln Gly Thr
            100                 105                 110

Leu Val Thr Val Ser Ser
        115

<210> SEQ ID NO 44
<211> LENGTH: 118
<212> TYPE: PRT
<213> ORGANISM: Artificial Sequence
<220> FEATURE:
<223> OTHER INFORMATION: Synthetic construct

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
            20                  25                  30

Trp Met Asn Trp Val Arg Gln Ala Pro Gly Gln Gly Leu Glu Trp Met
        35                  40                  45

Gly Gly Ile Tyr Pro Gly Asp Gly Glu Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Asp Tyr Leu Arg Ala Met Asp Tyr Trp Gly Gln Gly Thr
            100                 105                 110

Leu Val Thr Val Ser Ser
        115

<210> SEQ ID NO 45
<211> LENGTH: 118
<212> TYPE: PRT
<213> ORGANISM: Artificial Sequence
<220> FEATURE:
<223> OTHER INFORMATION: Synthetic construct

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Glu Ile Lys Tyr Asn Gln Lys Phe
    50                  55                  60

Gln Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Asp Tyr Leu Arg Ala Met Asp Tyr Trp Gly Gln Gly Thr
            100                 105                 110

Leu Val Thr Val Ser Ser
        115

<210> SEQ ID NO 46
<211> LENGTH: 118
<212> TYPE: PRT
<213> ORGANISM: Artificial Sequence
<220> FEATURE:
<223> OTHER INFORMATION: Synthetic construct

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Gly Ser Gly Tyr Asp Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Glu Ile Lys Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Asp Tyr Leu Arg Ala Met Asp Tyr Trp Gly Gln Gly Thr
            100                 105                 110

Leu Val Thr Val Ser Ser
        115

<210> SEQ ID NO 47
<211> LENGTH: 118
<212> TYPE: PRT
<213> ORGANISM: Artificial Sequence
<220> FEATURE:
<223> OTHER INFORMATION: Synthetic construct

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Gly Ser Gly Tyr Asp Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Glu Ile Lys Tyr Asn Gln Lys Phe
    50                  55                  60

Gln Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Ile Trp Gly Gln Gly Thr
            100                 105                 110

Met Val Thr Val Ser Ser

<210> SEQ ID NO 48
<211> LENGTH: 118
<212> TYPE: PRT
<213> ORGANISM: Artificial Sequence
<220> FEATURE:
<223> OTHER INFORMATION: Synthetic construct

<400> SEQUENCE: 48

```
Gln Val Gln Leu Val Gln Ser Gly Ala Glu Val Lys Lys Pro Gly Ser
1               5                   10                  15

Ser Val Lys Val Ser Cys Lys Gly Ser Gly Tyr Asp Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Glu Ile Lys Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Ile Trp Gly Gln Gly Thr
            100                 105                 110

Met Val Thr Val Ser Ser
        115
```

<210> SEQ ID NO 49
<211> LENGTH: 118
<212> TYPE: PRT
<213> ORGANISM: Artificial Sequence
<220> FEATURE:
<223> OTHER INFORMATION: Synthetic construct

<400> SEQUENCE: 49

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Glu Ile Lys Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Asp Tyr Leu Arg Ala Met Asp Tyr Trp Gly Gln Gly Thr
            100                 105                 110

Leu Val Thr Val Ser Ser
        115
```

<210> SEQ ID NO 50
<211> LENGTH: 118
<212> TYPE: PRT
<213> ORGANISM: Artificial Sequence
<220> FEATURE:
<223> OTHER INFORMATION: Synthetic construct

<400> SEQUENCE: 50

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
                20                  25                  30

Trp Met Asn Trp Val Arg Gln Ala Pro Gly Gln Gly Leu Glu Trp Met
            35                  40                  45

Gly Gln Ile Tyr Pro Gly Asp Gly Glu Ile Lys Tyr Asn Gln Lys Phe
        50                  55                  60

Gln Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Ile Trp Gly Gln Gly Thr
                100                 105                 110

Met Val Thr Val Ser Ser
        115

<210> SEQ ID NO 51
<211> LENGTH: 118
<212> TYPE: PRT
<213> ORGANISM: Artificial Sequence
<220> FEATURE:
<223> OTHER INFORMATION: Synthetic construct

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
                20                  25                  30

Trp Met Asn Trp Val Arg Gln Ala Pro Gly Gln Gly Leu Glu Trp Met
            35                  40                  45

Gly Gln Ile Tyr Pro Gly Asp Gly Glu Ile Lys Tyr Asn Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Ile Trp Gly Gln Gly Thr
                100                 105                 110

Met Val Thr Val Ser Ser
        115

<210> SEQ ID NO 52
<211> LENGTH: 118
<212> TYPE: PRT
<213> ORGANISM: Artificial Sequence
<220> FEATURE:
<223> OTHER INFORMATION: Synthetic construct

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
                20                  25                  30

Trp Met Asn Trp Val Arg Gln Ala Pro Gly Gln Gly Leu Glu Trp Met
            35                  40                  45

Gly Gln Ile Tyr Pro Gly Asp Gly Glu Ile Asn Tyr Asn Gln Lys Phe

```
                50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Asp Asp Tyr Leu Arg Ala Met Asp Ile Trp Gly Gln Gly Thr
                100                 105                 110

Met Val Thr Val Ser Ser
            115

<210> SEQ ID NO 53
<211> LENGTH: 118
<212> TYPE: PRT
<213> ORGANISM: Artificial Sequence
<220> FEATURE:
<223> OTHER INFORMATION: Synthetic construct

<400> SEQUENCE: 53

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Asp Phe Ser Asn Phe
                20                  25                  30

Trp Met Asn Trp Val Arg Gln Ala Pro Gly Gln Gly Leu Glu Trp Met
            35                  40                  45

Gly Gly Ile Tyr Pro Gly Asp Gly Glu Ile Lys Tyr Asn Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Asp Asp Tyr Leu Arg Ala Met Asp Ile Trp Gly Gln Gly Thr
                100                 105                 110

Met Val Thr Val Ser Ser
            115

<210> SEQ ID NO 54
<211> LENGTH: 118
<212> TYPE: PRT
<213> ORGANISM: Artificial Sequence
<220> FEATURE:
<223> OTHER INFORMATION: Synthetic construct

<400> SEQUENCE: 54

Gln Val Gln Leu Val Gln Ser Gly Ala Glu Val Lys Lys Pro Gly Ser
  1               5                  10                  15

Ser Val Lys Val Ser Cys Lys Gly Ser Gly Tyr Asp Phe Ser Asn Phe
                20                  25                  30

Trp Met Asn Trp Val Arg Gln Ala Pro Gly Gln Gly Leu Glu Trp Met
            35                  40                  45

Gly Gly Ile Tyr Pro Gly Asp Gly Glu Ile Lys Tyr Asn Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Asp Asp Tyr Leu Arg Ala Met Asp Ile Trp Gly Gln Gly Thr
                100                 105                 110
```

```
Met Val Thr Val Ser Ser
        115

<210> SEQ ID NO 55
<211> LENGTH: 118
<212> TYPE: PRT
<213> ORGANISM: Artificial Sequence
<220> FEATURE:
<223> OTHER INFORMATION: Synthetic construct

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Glu Ile Lys Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Tyr Trp Gly Gln Gly Thr
            100                 105                 110

Leu Val Thr Val Ser Ser
        115

<210> SEQ ID NO 56
<211> LENGTH: 118
<212> TYPE: PRT
<213> ORGANISM: Artificial Sequence
<220> FEATURE:
<223> OTHER INFORMATION: Synthetic construct

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Glu Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Ile Trp Gly Gln Gly Thr
            100                 105                 110

Met Val Thr Val Ser Ser
        115

<210> SEQ ID NO 57
<211> LENGTH: 118
<212> TYPE: PRT
<213> ORGANISM: Artificial Sequence
<220> FEATURE:
<223> OTHER INFORMATION: Synthetic construct
```

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Asp Gly Glu Ile Lys Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Asp Tyr Leu Arg Ala Met Asp Ile Trp Gly Gln Gly Thr
            100                 105                 110

Met Val Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: Synthetic construct

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Tyr
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Glu Ile Lys Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Asp Tyr Leu Arg Ala Met Asp Ile Trp Gly Gln Gly Thr
            100                 105                 110

Met Val Thr Val Ser Ser
        115

<210> SEQ ID NO 59
<211> LENGTH: 118
<212> TYPE: PRT
<213> ORGANISM: Artificial Sequence
<220> FEATURE:
<223> OTHER INFORMATION: Synthetic construct

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Tyr
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Glu Ile Lys Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Tyr Trp Gly Gln Gly Thr
            100                 105                 110

Leu Val Thr Val Ser Ser
            115

<210> SEQ ID NO 60
<211> LENGTH: 118
<212> TYPE: PRT
<213> ORGANISM: Artificial Sequence
<220> FEATURE:
<223> OTHER INFORMATION: Synthetic construct

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
            20                  25                  30

Ala Met Asn Trp Val Arg Gln Ala Pro Gly Gln Gly Leu Glu Trp Met
        35                  40                  45

Gly Gln Ile Tyr Pro Gly Asp Gly Glu Ile Lys Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Tyr Trp Gly Gln Gly Thr
            100                 105                 110

Leu Val Thr Val Ser Ser
            115

<210> SEQ ID NO 61
<211> LENGTH: 118
<212> TYPE: PRT
<213> ORGANISM: Artificial Sequence
<220> FEATURE:
<223> OTHER INFORMATION: Synthetic construct

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Ser Asn Phe
            20                  25                  30

Ala Met Asn Trp Val Arg Gln Ala Pro Gly Gln Gly Leu Glu Trp Met
        35                  40                  45

Gly Gln Ile Tyr Pro Gly Asp Gly Glu Ile Lys Tyr Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Leu Arg Ala Met Asp Ile Trp Gly Gln Gly Thr
            100                 105                 110

Met Val Thr Val Ser Ser
            115

<210> SEQ ID NO 62
<211> LENGTH: 107
<212> TYPE: PRT
<213> ORGANISM: Artificial Sequence
<220> FEATURE:
<223> OTHER INFORMATION: Synthetic construct

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Ala Pro Lys Leu Leu Leu
        35                  40                  45

Tyr Ser Ala Lys Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gly Gly Thr Lys Val Glu Ile Lys
            100                 105

<210> SEQ ID NO 63
<211> LENGTH: 107
<212> TYPE: PRT
<213> ORGANISM: Artificial Sequence
<220> FEATURE:
<223> OTHER INFORMATION: Synthetic construct

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Ser
            20                  25                  30

Leu Ala Trp Tyr Gln Gln Lys Pro Gly Lys Ala Pro Lys Leu Leu Leu
        35                  40                  45

Tyr Ser Ala Lys Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gly Gly Thr Lys Val Glu Ile Lys
            100                 105

<210> SEQ ID NO 64
<211> LENGTH: 107
<212> TYPE: PRT
<213> ORGANISM: Artificial Sequence
<220> FEATURE:
<223> OTHER INFORMATION: Synthetic construct

<400> SEQUENCE: 64

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gly Asn Ile His Asn Tyr
            20                  25                  30

Leu Ala Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gly Gly Thr Lys Val Glu Ile Lys
            100                 105

<210> SEQ ID NO 65
<211> LENGTH: 107
<212> TYPE: PRT
<213> ORGANISM: Artificial Sequence
<220> FEATURE:
<223> OTHER INFORMATION: Synthetic construct

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Ala Pro Lys Leu Leu Leu
        35                  40                  45

Tyr Ser Ala Ser Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gly Gly Thr Lys Val Glu Ile Lys
            100                 105

<210> SEQ ID NO 66
<211> LENGTH: 107
<212> TYPE: PRT
<213> ORGANISM: Artificial Sequence
<220> FEATURE:
<223> OTHER INFORMATION: Synthetic construct

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Gly Ile His Asn Tyr
            20                  25                  30

Leu Ala Trp Tyr Gln Gln Lys Pro Gly Lys Ala Pro Lys Leu Leu Leu
        35                  40                  45

Tyr Ser Ala Lys Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gly Gly Thr Lys Val Glu Ile Lys
            100                 105
```

```
<210> SEQ ID NO 67
<211> LENGTH: 107
<212> TYPE: PRT
<213> ORGANISM: Artificial Sequence
<220> FEATURE:
<223> OTHER INFORMATION: Synthetic construct

<400> SEQUENCE: 67
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile His Asn Tyr
            20                  25                  30

Leu Ala Trp Tyr Gln Gln Lys Pro Gly Lys Ala Pro Lys Leu Leu Leu
        35                  40                  45

Tyr Ser Ala Lys Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gly Gly Thr Lys Val Glu Ile Lys
            100                 105

```
<210> SEQ ID NO 68
<211> LENGTH: 107
<212> TYPE: PRT
<213> ORGANISM: Artificial Sequence
<220> FEATURE:
<223> OTHER INFORMATION: Synthetic construct

<400> SEQUENCE: 68
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile Ser Asn Tyr
            20                  25                  30

Leu Ala Trp Tyr Gln Gln Lys Pro Gly Lys Ala Pro Lys Leu Leu Leu
        35                  40                  45

Tyr Ser Ala Lys Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gly Gly Thr Lys Val Glu Ile Lys
            100                 105

```
<210> SEQ ID NO 69
<211> LENGTH: 107
<212> TYPE: PRT
<213> ORGANISM: Artificial Sequence
<220> FEATURE:
<223> OTHER INFORMATION: Synthetic construct

<400> SEQUENCE: 69
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

-continued

Leu Ala Trp Tyr Gln Gln Lys Pro Gly Lys Ala Pro Lys Phe Leu Leu
                35                  40                  45

Tyr Ser Ala Lys Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Trp Ser Ser Pro Tyr
                 85                  90                  95

Thr Phe Gly Gly Gly Thr Lys Val Glu Ile Lys
                100                 105

<210> SEQ ID NO 70
<211> LENGTH: 107
<212> TYPE: PRT
<213> ORGANISM: Artificial Sequence
<220> FEATURE:
<223> OTHER INFORMATION: Synthetic construct

<400> SEQUENCE: 70

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asn Ile His Asn Tyr
                20                  25                  30

Leu Ala Trp Tyr Gln Gln Lys Pro Gly Lys Ala Pro Lys Phe Leu Leu
                35                  40                  45

Tyr Ser Ala Lys Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Trp Ser Ser Pro Tyr
                 85                  90                  95

Thr Phe Gly Gly Gly Thr Lys Val Glu Ile Lys
                100                 105

<210> SEQ ID NO 71
<211> LENGTH: 107
<212> TYPE: PRT
<213> ORGANISM: Artificial Sequence
<220> FEATURE:
<223> OTHER INFORMATION: Synthetic construct

<400> SEQUENCE: 71

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Asn Ile His Asn Tyr
                20                  25                  30

Leu Ala Trp Tyr Gln Gln Lys Pro Gly Lys Ala Pro Lys Phe Leu Leu
                35                  40                  45

Tyr Ser Ala Lys Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Trp Ser Ser Pro Tyr
                 85                  90                  95

Thr Phe Gly Gln Gly Thr Lys Leu Glu Ile Lys
                100                 105

<210> SEQ ID NO 72

```
<211> LENGTH: 107
<212> TYPE: PRT
<213> ORGANISM: Artificial Sequence
<220> FEATURE:
<223> OTHER INFORMATION: Synthetic construct

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Ala Pro Lys Leu Leu Leu
        35                  40                  45

Tyr Ser Ala Lys Arg Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gly Gly Thr Lys Val Glu Ile Lys
            100                 105

<210> SEQ ID NO 73
<211> LENGTH: 107
<212> TYPE: PRT
<213> ORGANISM: Artificial Sequence
<220> FEATURE:
<223> OTHER INFORMATION: Synthetic construct

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Ala Pro Lys Leu Leu Leu
        35                  40                  45

Tyr Ser Ala Lys Arg Leu Glu Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gly Gly Thr Lys Val Glu Ile Lys
            100                 105

<210> SEQ ID NO 74
<211> LENGTH: 107
<212> TYPE: PRT
<213> ORGANISM: Artificial Sequence
<220> FEATURE:
<223> OTHER INFORMATION: Synthetic construct

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile His Asn Tyr
            20                  25                  30

Leu Ala Trp Tyr Gln Gln Lys Pro Gly Lys Ala Pro Lys Leu Leu Leu
        35                  40                  45
```

Tyr Ser Ala Lys Arg Leu Ala Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gly Gly Thr Lys Val Glu Ile Lys
            100                 105

<210> SEQ ID NO 75
<211> LENGTH: 107
<212> TYPE: PRT
<213> ORGANISM: Artificial Sequence
<220> FEATURE:
<223> OTHER INFORMATION: Synthetic construct

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile His Asn Tyr
                20                  25                  30

Leu Ala Trp Tyr Gln Gln Lys Pro Gly Lys Ala Pro Lys Leu Leu Leu
            35                  40                  45

Tyr Ser Ala Lys Arg Leu Glu Asp Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gly Gly Thr Lys Val Glu Ile Lys
            100                 105

<210> SEQ ID NO 76
<211> LENGTH: 107
<212> TYPE: PRT
<213> ORGANISM: Artificial Sequence
<220> FEATURE:
<223> OTHER INFORMATION: Synthetic construct

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile His Asn Tyr
                20                  25                  30

Leu Ala Trp Tyr Gln Gln Lys Pro Gly Lys Ala Pro Lys Phe Leu Leu
            35                  40                  45

Tyr Ser Ala Lys Arg Leu Glu Asp Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gly Gly Thr Lys Val Glu Ile Lys
            100                 105

<210> SEQ ID NO 77
<211> LENGTH: 107
<212> TYPE: PRT
<213> ORGANISM: Artificial Sequence
<220> FEATURE:
<223> OTHER INFORMATION: Synthetic construct

<400> SEQUENCE: 77

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile His Asn Tyr
            20                  25                  30

Leu Ala Trp Tyr Gln Gln Lys Pro Gly Lys Ala Pro Lys Phe Leu Leu
        35                  40                  45

Tyr Ser Ala Lys Arg Leu Glu Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys
            100                 105
```

<210> SEQ ID NO 78
<211> LENGTH: 107
<212> TYPE: PRT
<213> ORGANISM: Artificial Sequence
<220> FEATURE:
<223> OTHER INFORMATION: Synthetic construct

<400> SEQUENCE: 78

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile His Asn Tyr
            20                  25                  30

Leu Ala Trp Tyr Gln Gln Lys Pro Gly Lys Ala Pro Lys Phe Leu Leu
        35                  40                  45

Tyr Ser Ala Lys Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys
            100                 105
```

<210> SEQ ID NO 79
<211> LENGTH: 7
<212> TYPE: PRT
<213> ORGANISM: Artificial Sequence
<220> FEATURE:
<223> OTHER INFORMATION: Synthetic construct

<400> SEQUENCE: 79

```
Gly Tyr Asp Phe Ser Asn Phe
1               5
```

<210> SEQ ID NO 80
<211> LENGTH: 6
<212> TYPE: PRT
<213> ORGANISM: Artificial Sequence
<220> FEATURE:
<223> OTHER INFORMATION: Synthetic construct

<400> SEQUENCE: 80

```
Tyr Pro Gly Asp Gly Glu
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic construct

<400> SEQUENCE: 81

Asp Asp Tyr Leu Arg Ala Met Asp Tyr
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic construct

<400> SEQUENCE: 82

Gly Tyr Thr Phe Ser Asn Phe
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic construct

<400> SEQUENCE: 83

Gly Gly Asp Phe Ser Asn Phe
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic construct

<400> SEQUENCE: 84

Ile Pro Gly Asp Gly Glu
1               5

<210> SEQ ID NO 85
<211> LENGTH: 6
<212> TYPE: PRT
<213> ORGANISM: Artificial Sequence
<220> FEATURE:
<223> OTHER INFORMATION: Synthetic construct

<400> SEQUENCE: 85

Tyr Pro Ile Asp Gly Glu
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic construct

<400> SEQUENCE: 86
```

-continued

Tyr Pro Gly Asp Gly Thr
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic construct

<400> SEQUENCE: 87

Gly Tyr Asp Phe Ser Ser Tyr
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic construct

<400> SEQUENCE: 88

Gly Tyr Asp Phe Ser Ser Phe
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic construct

<400> SEQUENCE: 89

Gly Tyr Asp Phe Ser Asn Tyr
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic construct

<400> SEQUENCE: 90

Tyr Pro Gly Phe Gly Glu
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic construct

<400> SEQUENCE: 91

Asp Asp Tyr Leu Arg Ala Met Asp Val
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic construct

<400> SEQUENCE: 92

Asp Asp Tyr Leu Arg Ala Met Asp Ile

```
1               5

<210> SEQ ID NO 93
<211> LENGTH: 11
<212> TYPE: PRT
<213> ORGANISM: Artificial Sequence
<220> FEATURE:
<223> OTHER INFORMATION: Synthetic construct

<400> SEQUENCE: 93

Arg Ala Ser Gly Asn Ile His Asn Tyr Leu Ala
1               5                   10

<210> SEQ ID NO 94
<211> LENGTH: 7
<212> TYPE: PRT
<213> ORGANISM: Artificial Sequence
<220> FEATURE:
<223> OTHER INFORMATION: Synthetic construct

<400> SEQUENCE: 94

Ser Ala Lys Arg Leu Glu Ser
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic construct

<400> SEQUENCE: 95

Gln His Phe Trp Ser Ser Pro Tyr Thr
1               5

<210> SEQ ID NO 96
<211> LENGTH: 11
<212> TYPE: PRT
<213> ORGANISM: Artificial Sequence
<220> FEATURE:
<223> OTHER INFORMATION: Synthetic construct

<400> SEQUENCE: 96

Arg Ala Ser Gly Asn Ile His Asn Ser Leu Ala
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Synthetic construct

<400> SEQUENCE: 97

Ala Ala Ser Arg Leu Glu Ser
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic construct

<400> SEQUENCE: 98

Ser Ala Ser Arg Leu Glu Ser
1               5
```

```
<210> SEQ ID NO 99
<211> LENGTH: 11
<212> TYPE: PRT
<213> ORGANISM: Artificial Sequence
<220> FEATURE:
<223> OTHER INFORMATION: Synthetic construct

<400> SEQUENCE: 99

Arg Ala Ser Gly Gly Ile His Asn Tyr Leu Ala
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Synthetic construct

<400> SEQUENCE: 100

Arg Ala Ser Gln Asn Ile His Asn Tyr Leu Ala
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Synthetic construct

<400> SEQUENCE: 101

Arg Ala Ser Gly Asn Ile Ser Asn Tyr Leu Ala
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Synthetic construct

<400> SEQUENCE: 102

Ser Ala Lys Arg Leu Ala Ser
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic construct

<400> SEQUENCE: 103

Ser Ala Lys Arg Leu Glu Asp
1               5

<210> SEQ ID NO 104
<211> LENGTH: 118
<212> TYPE: PRT
<213> ORGANISM: Artificial Sequence
<220> FEATURE:
<223> OTHER INFORMATION: Synthetic construct

<400> SEQUENCE: 104

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Phe Ser Leu Thr Thr Tyr
            20                  25                  30

Gly Trp Ser Trp Ile Arg Gln Pro Pro Gly Lys Gly Leu Glu Trp Ile
        35                  40                  45

Gly Tyr Ile Trp Gly Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys His Lys Gly Thr Ser His Ala Met Glu Tyr Trp Gly Gln Gly Thr
                100                 105                 110

Met Val Thr Val Ser Ser
            115

<210> SEQ ID NO 105
<211> LENGTH: 106
<212> TYPE: PRT
<213> ORGANISM: Artificial Sequence
<220> FEATURE:
<223> OTHER INFORMATION: Synthetic construct

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Arg Val Ile Phe Leu
            20                  25                  30

Ala Trp Tyr Gln Gln Lys Pro Gly Gln Ala Pro Arg Leu Leu Ile Tyr
        35                  40                  45

Asp Thr Ser Asn Lys Ala Thr Gly Val Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Tyr Pro Pro Thr
                85                  90                  95

Phe Gly Gly Gly Thr Lys Val Glu Ile Lys
            100                 105

<210> SEQ ID NO 106
<211> LENGTH: 118
<212> TYPE: PRT
<213> ORGANISM: Artificial Sequence
<220> FEATURE:
<223> OTHER INFORMATION: Synthetic construct

<400> SEQUENCE: 106

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Gly Val Asp Trp Val Arg Gln Pro Pro Gly Lys Gly Leu Glu Trp Ile
        35                  40                  45

Gly Val Ile Trp Gly Gly Asn Thr Asn Tyr Asn Ser Ser Leu Lys
    50                  55                  60

Ser Arg Val Thr Ile Ser Lys Asp Thr Ser Lys Asn Gln Val Phe Leu
65                  70                  75                  80

Lys Leu Ser Ser Val Thr Ala Ala Asp Thr Ala Val Tyr Tyr Cys Ala
                85                  90                  95
```

Lys His Lys Gly Thr Ser His Ala Met Glu Tyr Trp Gly Gln Gly Thr
                100                 105                 110

Met Val Thr Val Ser Ser
        115

<210> SEQ ID NO 107
<211> LENGTH: 106
<212> TYPE: PRT
<213> ORGANISM: Artificial Sequence
<220> FEATURE:
<223> OTHER INFORMATION: Synthetic construct

<400> SEQUENCE: 107

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Arg Val Ile Phe Met
            20                  25                  30

Tyr Trp Tyr Gln Gln Lys Pro Gly Gln Ser Pro Arg Leu Leu Ile Tyr
        35                  40                  45

Asp Thr Ser Asn Leu Ala Thr Gly Val Pro Ala Arg Phe Ser Gly Gly
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Tyr Pro Pro Thr
                85                  90                  95

Phe Gly Gly Gly Thr Lys Val Glu Ile Lys
            100                 105

<210> SEQ ID NO 108
<211> LENGTH: 467
<212> TYPE: PRT
<213> ORGANISM: Homo sapiens

<400> SEQUENCE: 108

Met Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
            20                  25                  30

Ser Val Thr Val Gln Glu Gly Met Cys Val His Val Arg Cys Ser Phe
        35                  40                  45

Ser Tyr Pro Val Asp Ser Gln Thr Asp Ser Asp Pro Val His Gly Tyr
    50                  55                  60

Trp Phe Arg Ala Gly Asn Asp Ile Ser Trp Lys Ala Pro Val Ala Thr
65                  70                  75                  80

Asn Asn Pro Ala Trp Ala Val Gln Glu Glu Thr Arg Asp Arg Phe His
                85                  90                  95

Leu Leu Gly Asp Pro Gln Thr Lys Asn Cys Thr Leu Ser Ile Arg Asp
            100                 105                 110

Ala Arg Met Ser Asp Ala Gly Arg Tyr Phe Phe Arg Met Glu Lys Gly
        115                 120                 125

Asn Ile Lys Trp Asn Tyr Lys Tyr Asp Gln Leu Ser Val Asn Val Thr
    130                 135                 140

Ala Leu Thr His Arg Pro Asn Ile Leu Ile Pro Gly Thr Leu Glu Ser
145                 150                 155                 160

Gly Cys Phe Gln Asn Leu Thr Cys Ser Val Pro Trp Ala Cys Glu Gln
                165                 170                 175

Gly Thr Pro Pro Met Ile Ser Trp Met Gly Thr Ser Val Ser Pro Leu
            180                 185                 190

His Pro Ser Thr Thr Arg Ser Ser Val Leu Thr Leu Ile Pro Gln Pro
            195                 200                 205

Gln His His Gly Thr Ser Leu Thr Cys Gln Val Thr Leu Pro Gly Ala
        210                 215                 220

Gly Val Thr Thr Asn Arg Thr Ile Gln Leu Asn Val Ser Tyr Pro Pro
225                 230                 235                 240

Gln Asn Leu Thr Val Thr Val Phe Gln Gly Glu Gly Thr Ala Ser Thr
                245                 250                 255

Ala Leu Gly Asn Ser Ser Leu Ser Val Leu Glu Gly Gln Ser Leu
            260                 265                 270

Arg Leu Val Cys Ala Val Asp Ser Asn Pro Pro Ala Arg Leu Ser Trp
        275                 280                 285

Thr Trp Arg Ser Leu Thr Leu Tyr Pro Ser Gln Pro Ser Asn Pro Leu
        290                 295                 300

Val Leu Glu Leu Gln Val His Leu Gly Asp Gly Glu Phe Thr Cys
305                 310                 315                 320

Arg Ala Gln Asn Ser Leu Gly Ser Gln His Val Ser Leu Asn Leu Ser
                325                 330                 335

Leu Gln Gln Glu Tyr Thr Gly Lys Met Arg Pro Val Ser Gly Val Leu
            340                 345                 350

Leu Gly Ala Val Gly Gly Ala Gly Ala Thr Ala Leu Val Phe Leu Ser
            355                 360                 365

Phe Cys Val Ile Phe Ile Val Val Arg Ser Cys Arg Lys Lys Ser Ala
        370                 375                 380

Arg Pro Ala Ala Asp Val Gly Asp Ile Gly Met Lys Asp Ala Asn Thr
385                 390                 395                 400

Ile Arg Gly Ser Ala Ser Gln Gly Asn Leu Thr Glu Ser Trp Ala Asp
                405                 410                 415

Asp Asn Pro Arg His Gly Leu Ala Ala His Ser Ser Gly Glu Glu
            420                 425                 430

Arg Glu Ile Gln Tyr Ala Pro Leu Ser Phe His Lys Gly Glu Pro Gln
            435                 440                 445

Asp Leu Ser Gly Gln Glu Ala Thr Asn Asn Glu Tyr Ser Glu Ile Lys
        450                 455                 460

Ile Pro Lys
465

<210> SEQ ID NO 109
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa = Gly or Tyr
<220> FEATURE:
<221> NAME/KEY: MISC_FEATURE
<222> LOCATION: (3)..(3)
<223> OTHER INFORMATION: Xaa = Lys or Thr
<220> FEATURE:
<221> NAME/KEY: MISC_FEATURE
<222> LOCATION: (6)..(6)
<223> OTHER INFORMATION: Xaa = Trp or Ser or Tyr
<220> FEATURE:
<221> NAME/KEY: MISC_FEATURE
<222> LOCATION: (7)..(7)

```
<223> OTHER INFORMATION: Xaa = Phe or Tyr

<400> SEQUENCE: 109

Gly Xaa Xaa Phe Ser Xaa Xaa
1               5

<210> SEQ ID NO 110
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa = Gly or Ile
<220> FEATURE:
<221> NAME/KEY: MISC_FEATURE
<222> LOCATION: (4)..(4)
<223> OTHER INFORMATION: Xaa = Asp or Phe

<400> SEQUENCE: 110

Tyr Pro Xaa Xaa Gly Glu
1               5

<210> SEQ ID NO 111
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: Xaa = Tyr or Ile or Val

<400> SEQUENCE: 111

Asp Tyr Leu Arg Ala Met Asp Xaa
1               5

<210> SEQ ID NO 112
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa = Gly or Gln
<220> FEATURE:
<221> NAME/KEY: MISC_FEATURE
<222> LOCATION: (5)..(5)
<223> OTHER INFORMATION: Xaa = Asn or Gly
<220> FEATURE:
<221> NAME/KEY: MISC_FEATURE
<222> LOCATION: (7)..(7)
<223> OTHER INFORMATION: Xaa = His or Ser

<400> SEQUENCE: 112

Arg Ala Ser Xaa Xaa Ile Xaa Asn Tyr Leu Ala
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
```

```
<222> LOCATION: (1)..(1)
<223> OTHER INFORMATION: Xaa = Ser or Ala
<220> FEATURE:
<221> NAME/KEY: MISC_FEATURE
<222> LOCATION: (3)..(3)
<223> OTHER INFORMATION: Xaa = Lys or Ser
<220> FEATURE:
<221> NAME/KEY: MISC_FEATURE
<222> LOCATION: (6)..(6)
<223> OTHER INFORMATION: Xaa = Glu or Ala
<220> FEATURE:
<221> NAME/KEY: MISC_FEATURE
<222> LOCATION: (7)..(7)
<223> OTHER INFORMATION: Xaa = Ser or Asp

<400> SEQUENCE: 113

Xaa Ala Xaa Arg Leu Xaa Xaa
1               5
```

ANTI-SIGLEC-7 ANTIBODIES FOR THE TREATMENT OF CANCER

CROSS-REFERENCE TO RELATED APPLICATIONS

This application is a national stage of international application no. PCT/US2017/045641, filed Aug. 4, 2017, which claims priority benefit of U.S. provisional application No. 62/371,680, filed Aug. 5, 2016, the disclosure of which is herein incorporated by reference.

REFERENCE TO SEQUENCE LISTING

This application includes a Sequence Listing as a text file named "101413-1057130-000110US_SEQLIST.txt" created Jan. 24, 2019, and containing 98,902 bytes. The material contained in this text file is incorporated by reference in its entirety for all purposes.

BACKGROUND OF THE INVENTION

Siglec-7, also known as p75 or AIRM, is a member of the sialic acid-binding lectins (Siglec) of the immunoglobulin (Ig) superfamily. Siglec receptors bind glycans containing sialic acid, but differ in their recognition of the linkage regiochemistry and spatial distribution of sialic residues. The members of the family also have distinct expression patterns. High level expression of Siglec-7 has been observed on Natural Killer (NK) cells. Expression has also been observed on a subset CD8+ T cells. Siglec-7 has also been observed to have an inhibitory role on NK cell-mediated tumor clearance (Jandus, et al., *J. Clin. Invest.* 124: 1810-20, 2014); Hudak et al., *Nat. Chem. Biol.* 10:69-77, 2014).

A broad range of human malignancies overexpress Siglec-7 ligands sialoglycans, including sialocglycans that are the ligands for Siglec-7. Siglec-7 has also been observed to have an inhibitory role on NK cell-mediated tumor clearance (Jandus, et al., *J. Clin. Invest.* 124: 1810-20, 2014).

BRIEF SUMMARY OF ASPECTS OF THE DISCLOSURE

The disclosure is based, in part, on the discovery that an elevated level of tumor-infiltrating CD8+ T cells express Siglec-7; and further, that an antibody that blocks Siglec-7-ligand binding interactions and/or decreases the level of Siglec-7 that is expressed on CD8+ cells increases killing of tumor cells. Accordingly, the disclosure provides antibodies and uses of such antibodies for inhibiting tumor growth.

In one aspect, the disclosure provides a method of inhibiting proliferation of tumor cells, the method comprising administering a therapeutically effective amount of an anti-Siglec-7 antibody to a patient that has cancer, wherein the patient has a primary tumor or metastatic lesion that comprises an elevated level of CD8+ infiltrating-T cells that express Siglec-7, and further, wherein the tumor or metastatic lesion comprises cancer cells that express sialylated Siglec-7 ligands. In some embodiments, the anti-Siglec-7 antibody has a $K_D$ of 50 pM or less. In some embodiments, the anti-Siglec-7 antibody blocks ligand binding at an $IC_{50}$ of less than about 4000 pM, or blocks ligand binding at an $IC_{50}$ of less than about 3500 pM, and optionally may have a $K_D$ of 50 pM or less. In some embodiments, which may be combined with the foregoing embodiments, the anti-Siglec-7 antibody has an internalization activity of less than about 70 pM or than about 25 pM. In some embodiments, the anti-Siglec-7 antibody has an internalization activity of less than about 70 pM or than about 25 pM; and does not block ligand binding.

In some embodiments, the anti-Siglec-7 antibody for use in the method blocks binding of ligand to Siglec-7 and competes with an antibody QA79 produced from the hybridoma deposited under accession number ICLC PD99003 for binding to Siglec-7, but does not compete with antibody Z176 or antibody S7.7 for binding to Siglec-7. In some embodiments, the antibody competes with an antibody comprising the $V_H$ and $V_L$ of 2G12 as designated in FIGS. 1 and 2 for binding to Siglec-7. In some embodiments, the anti-Siglec-7 antibody has a $V_H$ region that comprises at least one CDR, or at least two CDRs, of a heavy chain variable region sequence of SEQ ID NO:2. In some embodiments, the anti-Siglec-7 antibody has a $V_H$ region that comprises a CDR3 of a heavy chain variable region sequence of SEQ ID NO:2. In some embodiments, the anti-Siglec-7 antibody has a $V_H$ region that comprises a CDR1, CDR2, and CDR3 of a heavy chain variable region sequence of SEQ ID NO:2. In some embodiments, the anti-Siglec-7 antibody has a $V_L$ region that comprises at least one CDR, or at least two CDRs, of a light chain variable region sequence of SEQ ID NO: 16. In some embodiments, the anti-Siglec-7 antibody has a $V_L$ region that comprises a CDR3 of a light chain variable region sequence of SEQ ID NO: 16. In some embodiments, the anti-Siglec-7 antibody has a $V_L$ region that comprises a CDR1, CDR2, and CDR3 of a light chain variable region sequence of SEQ ID NO: 16. In some embodiments, the antibody has six CDRs of antibody 2G12 as designated in FIGS. 1 and 2.

In some embodiments, the anti-Siglec-7 antibody for use in the method has internalization activity, does not block ligand binding to Siglec-7, and competes with antibody S7.7, but not with antibody QA79 or antibody Z176 for binding to Siglec-7. In some embodiments, the antibody competes with an antibody comprising the $V_H$ and $V_L$ of 8A2 as designated in FIGS. 1 and 2 for binding to Siglec-7. In some embodiments, the anti-Siglec-7 antibody has a $V_H$ region that comprises at least one CDR, or at least two CDRs, of a heavy chain variable region sequence of SEQ ID NO:4. In some embodiments, the anti-Siglec-7 antibody has a $V_H$ region that comprises a CDR3 of a heavy chain variable region sequence of SEQ ID NO:4. In some embodiments, the anti-Siglec-7 antibody has a $V_H$ region that comprises a CDR1, CDR2, and CDR3 of a heavy chain variable region sequence of SEQ ID NO:4. In some embodiments, the anti-Siglec-7 antibody has a $V_L$ region that comprises at least one CDR, or at least two CDRs, of a light chain variable region sequence of SEQ ID NO: 18. In some embodiments, the anti-Siglec-7 antibody has a $V_L$ region that comprises a CDR3 of a light chain variable region sequence of SEQ ID NO:18. In some embodiments, the anti-Siglec-7 antibody has a $V_L$ region that comprises a CDR1, CDR2, and CDR3 of a light chain variable region sequence of SEQ ID NO: 18. In some embodiments, the anti-Siglec-7 antibody has six CDRs of the antibody designated as 8A2 in FIGS. 1 and 2.

In some embodiments, the anti-Siglec-7 antibody for use in the method, has internalization activity, does not block ligand binding to Siglec-7, and competes with antibody Z176, but not with QA79 or S7.7 for binding to Siglec-7. In some embodiments, the anti-Siglec-7 antibody competes with an antibody comprising the $V_H$ and $V_L$ of the antibody designated as 5D1 for binding to Siglec-7. In some embodiments, the anti-Siglec-7 antibody has a $V_H$ region that comprises at least one CDR, or at least two CDRs, of a heavy chain variable region sequence of SEQ ID NO:3. In some embodiments, the anti-Siglec-7 antibody has a $V_H$ region that comprises a CDR3 of a heavy chain variable region sequence of SEQ ID NO:3. In some embodiments, the anti-Siglec-7 antibody has a $V_H$ region that comprises a CDR1, CDR2, and CDR3 of a heavy chain variable region sequence of SEQ ID NO:3. In some embodiments, the anti-Siglec-7 antibody has a $V_L$ region that comprises at least one CDR, or at least two CDRs, of a light chain variable region sequence of SEQ ID NO: 17. In some embodiments, the anti-Siglec-7 antibody has a $V_L$ region that comprises a CDR3 of a light chain variable region sequence of SEQ ID NO: 17. In some embodiments, the anti-Siglec-7 antibody has a $V_L$ region that comprises a CDR1, CDR2, and CDR3 of a light chain variable region sequence of SEQ ID NO: 17. In some embodiments, the antibody has six CDRs of the antibody designated as 5D1 in FIGS. 1 and 2.

In some embodiments, the anti-Siglec-7 antibody for use in the method has internalization activity, does not block ligand binding to Siglec-7, and does not compete with antibody Z176, QA79, or S7.7 for binding to Siglec-7. In some embodiments, the antibody competes with an antibody comprising a $V_H$ and $V_L$ of the antibody designated as 4B12 in FIGS. 1 and 2 for binding to Siglec-7. In some embodiments, the anti-Siglec-7 antibody has a $V_H$ region that comprises at least one CDR, or at least two CDRs, of a heavy chain variable region sequence of SEQ ID NO: 11. In some embodiments, the anti-Siglec-7 antibody has a $V_H$ region that comprises a CDR3 of a heavy chain variable region sequence of SEQ ID NO: 11. In some embodiments, the anti-Siglec-7 antibody has a $V_H$ region that comprises a CDR1, CDR2, and CDR3 of a heavy chain variable region sequence of SEQ ID NO: 11. In some embodiments, the anti-Siglec-7 antibody has a $V_L$ region that comprises at least one CDR, or at least two CDRs, of a light chain variable region sequence of SEQ ID NO:25. In some embodiments, the anti-Siglec-7 antibody has a $V_L$ region that comprises a CDR3 of a light chain variable region sequence of SEQ ID NO:25. In some embodiments, the anti-Siglec-7 antibody has a $V_L$ region that comprises a CDR1, CDR2, and CDR3 of a light chain variable region sequence of SEQ ID NO:25. In some embodiments, the anti-Siglec-7 antibody has six CDRs of the antibody designated as 4B12 in FIGS. 1 and 2.

In any of the foregoing embodiments, the antibody may be in a monovalent format or may be in an Fv, Fab, Fab', scFv, diabody, or F(ab')$_2$ fragment. In some embodiments, such an antibody is PEGylated.

In some embodiments, the patient that is administered the antibody has a solid tumor, such as melanoma, lung cancer, or colorectal cancer.

In a further aspect, the disclosure provide an anti-Siglec-7 antibody that blocks binding of ligand to Siglec-7 and competes with antibody QA79 produced from the hybridoma deposited under accession number ICLC PD99003 for binding to Siglec-7, but does not compete with antibody Z176 or antibody S7.7 for binding to Siglec-7. In some embodiments, the antibody competes with an antibody comprising the $V_H$ and $V_L$ of 2G12 as designated in FIGS. 1 and 2 for binding to Siglec-7. In some embodiments, the anti-Siglec-7 antibody has a $V_H$ region that comprises at least one CDR, or at least two CDRs, of a heavy chain variable region sequence of SEQ ID NO:2. In some embodiments, the anti-Siglec-7 antibody has a $V_H$ region that comprises a CDR3 of a heavy chain variable region sequence of SEQ ID NO:2. In some embodiments, the anti-Siglec-7 antibody has a $V_H$ region that comprises a CDR1, CDR2, and CDR3 of a heavy chain variable region sequence of SEQ ID NO:2. In some embodiments, the anti-Siglec-7 antibody has a $V_L$ region that comprises at least one CDR, or at least two CDRs, of a light chain variable region sequence of SEQ ID NO: 16. In some embodiments, the anti-Siglec-7 antibody has a $V_L$ region that comprises a CDR3 of a light chain variable region sequence of SEQ ID NO: 16. In some embodiments, the anti-Siglec-7 antibody has a $V_L$ region that comprises a CDR1, CDR2, and CDR3 of a light chain variable region sequence of SEQ ID NO: 16. In some embodiments, the antibody has six CDRs of antibody 2G12 as designated in FIGS. 1 and 2.

In another aspect, the disclosure provides an anti-Siglec-7 antibody that has internalization activity, does not block ligand binding to Siglec-7, and competes with antibody S7.7, but not with antibody QA79 or antibody Z176 for binding to Siglec-7. In some embodiments, the antibody competes with an antibody comprising the $V_H$ and $V_L$ of 8A2 as designated in FIGS. 1 and 2 for binding to Siglec-7. In some embodiments, the anti-Siglec-7 antibody has a $V_H$ region that comprises at least one CDR, or at least two CDRs, of a heavy chain variable region sequence of SEQ ID NO:4, SEQ ID NO:104, or SEQ ID NO:106. In some embodiments, the anti-Siglec-7 antibody has a $V_H$ region that comprises a CDR3 of a heavy chain variable region sequence of SEQ ID NO:4, SEQ ID NO:104, or SEQ ID NO: 106. In some embodiments, the anti-Siglec-7 antibody has a $V_H$ region that comprises a CDR1, CDR2, and CDR3 of a heavy chain variable region sequence of SEQ ID NO:4, SEQ ID NO:104, or SEQ ID NO:106. In some embodiments, the anti-Siglec-7 antibody has a $V_L$ region that comprises at least one CDR, or at least two CDRs, of a light chain variable region sequence of SEQ ID NO:18, SEQ ID NO:105, or SEQ ID NO:107. In some embodiments, the anti-Siglec-7 antibody has a $V_L$ region that comprises a CDR3 of a light chain variable region sequence of SEQ ID NO:18, SEQ ID NO: 105, or SEQ ID NO: 107. In some embodiments, the anti-Siglec-7 antibody has a $V_L$ region that comprises a CDR1, CDR2, and CDR3 of a light chain variable region sequence of SEQ ID NO: 18. SEQ ID NO: 105, or SEQ ID NO: 107. In some embodiments, the anti-Siglec-7 antibody has six CDRs of the antibody designated as 8A2 in FIGS. 1 and 2.

In still another aspect, the disclosure provides an anti-Siglec-7 antibody that has internalization activity, does not block ligand binding to Siglec-7, and competes with antibody Z176, but not with QA79 or S7.7 for binding to Siglec-7. In some embodiments, the anti-Siglec-7 antibody competes with an antibody comprising the $V_H$ and $V_L$ of the antibody designated as 5D1 for binding to Siglec-7. In some embodiments, the anti-Siglec-7 antibody has a $V_H$ region that comprises at least one CDR, or at least two CDRs, of a heavy chain variable region sequence of SEQ ID NO:3. In some embodiments, the anti-Siglec-7 antibody has a $V_H$ region that comprises a CDR3 of a heavy chain variable region sequence of SEQ ID NO:3. In some embodiments, the anti-Siglec-7 antibody has a $V_H$ region that comprises a CDR1, CDR2, and CDR3 of a heavy chain variable region sequence of SEQ ID NO:3. In some embodiments, the anti-Siglec-7 antibody has a $V_L$ region that comprises at least one CDR, or at least two CDRs, of a light chain variable region sequence of SEQ ID NO: 17. In some embodiments, the anti-Siglec-7 antibody has a $V_L$ region that comprises a CDR3 of a light chain variable region sequence of SEQ ID NO: 17. In some embodiments, the anti-Siglec-7 antibody has a $V_L$ region that comprises a CDR1, CDR2, and CDR3 of a light chain variable region sequence of SEQ ID NO: 17. In some embodiments, the antibody has six CDRs of the antibody designated as 5D1 in FIGS. 1 and 2.

In a further aspect, the disclosure provide an anti-Siglec-7 antibody that has internalization activity, does not block ligand binding to Siglec-7, and does not compete with antibody Z176, QA79, or S7.7 for binding to Siglec-7. In some embodiments, the antibody competes with an antibody comprising a $V_H$ and $V_L$ of the antibody designated as 4B12 in FIGS. 1 and 2 for binding to Siglec-7. In some embodiments, the anti-Siglec-7 antibody has a $V_H$ region that comprises at least one CDR, or at least two CDRs, of a heavy chain variable region sequence of SEQ ID NO: 11. In some embodiments, the anti-Siglec-7 antibody has a $V_H$ region that comprises a CDR3 of a heavy chain variable region sequence of SEQ ID NO: 11. In some embodiments, the anti-Siglec-7 antibody has a $V_H$ region that comprises a CDR1, CDR2, and CDR3 of a heavy chain variable region sequence of SEQ ID NO: 11. In some embodiments, the anti-Siglec-7 antibody has a $V_L$ region that comprises at least one CDR, or at least two CDRs, of a light chain variable region sequence of SEQ ID NO:25. In some embodiments, the anti-Siglec-7 antibody has a $V_L$ region that comprises a CDR3 of a light chain variable region sequence of SEQ ID NO:25. In some embodiments, the anti-Siglec-7 antibody has a $V_L$ region that comprises a CDR1, CDR2, and CDR3 of a light chain variable region sequence of SEQ ID NO:25. In some embodiments, the anti-Siglec-7 antibody has six CDRs of the antibody designated as 4B12 in FIGS. 1 and 2.

The disclosure additionally provides an anti-Siglec-7 antibody having a $V_H$ region that comprises at least one CDR, or at least two CDRs, of a $V_H$ region sequence set forth in FIG. 1; or an anti-Siglec-7 antibody having a $V_H$ region that comprises a CDR1, CDR2, and CDR3 of one of the heavy chain variable region sequences set forth in FIG. 1.

The disclosure further provides an anti-Siglec-7 antibody having a $V_L$ region that comprises at least one CDR, or at least two CDRs, of a $V_L$ region sequence set forth in FIG. 2; or an anti-Siglec-7 antibody having a $V_L$ region that comprises a CDR1, CDR2, and CDR3 of one of the light chain variable region sequences set forth in FIG. 2.

In some aspects, the invention provides an anti-Siglec-7 antibody comprising a $V_H$ region that comprises at least one CDR, or at least two CDRs, of a $V_H$ region sequence set forth in FIG. 1; and a $V_L$ region that comprises at least one CDR, or at least two CDRs, of a $V_L$ region sequence set forth in FIG. 2, where the $V_L$ sequence in FIG. 2 has the same antibody designation as the $V_H$ sequence in FIG. 1.

In some embodiment an anti-Siglec-7 antibody of the disclosure comprises a $V_H$ region that comprises a CDR1, CDR2, and CDR3 of a heavy chain variable region sequences set forth in FIG. 1; and a $V_L$ region that comprises a CDR1, CDR2, and CDR3 of a light chain variable region sequence set forth in FIG. 2, where the $V_L$ sequence in FIG. 2 has the same antibody designation as the $V_H$ sequence in FIG. 1.

In another aspect, provided herein is an anti-Siglec-7 antibody that competes with an antibody having a variable heavy chain sequence of SEQ ID NO: 1 and a variable light chain sequence of SEQ ID NO: 15 for binding to Siglec-7. In some embodiments, the antibody comprises a heavy chain variable region comprising a CDR3 having a sequence as set forth in any one of SEQ ID NOS:29-31, 33, and 35-61, in which 1, 2, or 3 amino acids are substituted; or comprises a heavy chain variable region comprising a CDR3 as set forth in any one of SEQ ID NOS:29-31, 33, and 35-61. In some embodiments, the heavy chain variable region comprises a CDR1 having a sequence as set forth in any one of SEQ ID NOS:29-31, 33, and 35-61 in which 1, 2, or 3 amino acids are substituted; and/or a CDR2 having a sequence as set forth in any one of SEQ ID NOS:29-31, 33, and 35-61 in which 1, 2, or 3 amino acids are substituted. In some embodiments, the heavy chain variable region comprises a CDR1 having a sequence as set forth in any one of SEQ ID NOS:29-31, 33, and 35-61 and a CDR2 having a sequence as set forth in any one of SEQ ID NOS:29-31, 33, and 35-61. In some embodiments, which can be combined with any of the preceding embodiments in this paragraph, the anti-Siglec-7 antibody comprises a light chain variable region comprising a CDR3 having a sequence as set forth in any one of SEQ ID NOS:62 and 64-78 in which 1, 2, or 3 amino acids are substituted; or comprises a light chain variable region comprising a CDR3 as set forth in any one of SEQ ID NOS:62 and 64-78. In some embodiments, the light chain variable region comprises a CDR1 having a sequence as set forth in any one of SEQ ID NOS:62 and 64-78 in which 1, 2, or 3 amino acids are substituted; and/or a CDR2 having a sequence as set forth in any one of SEQ ID NOS:62 and 64-78 in which 1, 2, or 3 amino acids are substituted. In some embodiments, the light chain variable region comprises a CDR1 having a sequence as set forth in any one of SEQ ID NOS:62 and 64-78 and a CDR2 having a sequence as set forth in any one of SEQ ID NOS:62 and 64-78. In some embodiments, the anti-Siglec-7 antibody has ligand blocking activity; and/or has a $K_D$ of less than about 100 pM when measured as a monovalent Fab; and/or has an internalization activity of less than about 100 pM. In some embodiments, the anti-Siglec-7 antibody has a $K_D$ of less than about 75 pM when measured as a monovalent Fab. In some embodiments, the anti-Siglec-7 antibody has an internalization activity of about 70 pM or less. In some embodiments, the anti-Siglec-7 antibody has an internalization activity of less than about 25 pM.

In another aspect, provided herein is an anti-Siglec-7 antibody that comprises a heavy chain variable region having at least 80%, or at least 85%, 90%, 91%, 92%, 93%, 94%, 95%, 96%, 97%, 98%, 99%, or 100% sequence identity to the amino acid sequence of a heavy chain variable region of any one of SEQ ID NOS:29-31, 33, and 35-61; and/or a light chain variable region having at least 80%, or at least 85%, 90%, 91%, 92%, 93%, 94%, 95%, 96%, 97%, 98%, 99%, or 100% sequence identity to the amino acid sequence of a light chain variable region of any one of SEQ ID NOS:62 and 64-78. In some embodiments, the anti-Siglec-7 antibody comprises a heavy chain variable region having at least 80%, 85%, 90%, 91%, 92%, 93%, 94%, 95%, 96%, 97%, 98%, 99%, or 100% sequence identity to the amino acid sequence of a heavy chain variable region of any of SEQ ID NOS:41, 42, 43, 44, 45, 46, 47, 48, 49, 50, 51, 52, 53, 54, 55, 57, 58, 59, 60 or 61; and a light chain variable region having at least 80%, 85%, 90%, 91%, 92%, 93%, 94%, 95%, 96%, 97%, 98%, 99%, or 100% sequence identity to the amino acid sequence of a light chain variable region of SEQ ID NO:69, 70, 71, 72, 73, 74, 75, 76, 77, or 78. In some embodiments, the anti-Siglec-7 antibody has ligand blocking activity; and/or has a $K_D$ of less than about 100 pM when measured as a monovalent Fab; and/or has an internalization activity of less than about 100 pM. In some embodiments, the anti-Siglec-7 antibody has a $K_D$ of less than about 75 pM when measured as a monovalent Fab. In some embodiments, the anti-Siglec-7 antibody has an internalization activity of about 70 pM or less. In some embodiments, the anti-Siglec-7 antibody has an internalization activity of less than about 25 pM.

In a further aspect, provided herein is an anti-Siglec-7 antibody comprises a heavy chain variable region comprising the CDR1, CDR2, and CDR3 sequences as set forth in a heavy chain variable region sequence selected from SEQ ID NO:43, 45, 46, 47, 48, 49, 50, 51, 54, 55, 57, and 58; and a light chain variable region comprising the CDR1, CDR2, and CDR3 sequences of SEQ ID NO:69. Additionally provided herein is an anti-Siglec-7 antibody that comprises a heavy chain variable region comprising the CDR1, CDR2, and CDR3 sequences as set forth in a heavy chain variable region sequence selected from SEQ ID NO:53, 54, 51, 55, 58, and 59; and a light chain variable region comprising the CDR1, CDR2, and CDR3 sequences of SEQ ID NO:78. In some embodiments, the anti-Siglec-7 antibody has ligand blocking activity; and/or has a $K_D$ of less than about 100 pM when measured as a monovalent Fab; and/or has an internalization activity of less than about 100 pM. In some embodiments, the anti-Siglec-7 antibody has a $K_D$ of less than about 75 pM when measured as a monovalent Fab. In some embodiments, the anti-Siglec-7 antibody has an internalization activity of about 70 pM or less. In some embodiments, the anti-Siglec-7 antibody has an internalization activity of less than about 25 pM.

In a further aspect, provided herein is an anti-Siglec-7 antibody that comprises:
a) a heavy chain variable region comprising the CDR1, CDR2, and CDR3 sequences as set forth in SEQ ID NO:43, and a light chain variable region comprising the CDR1, CDR2, and CDR3 sequences as set forth in SEQ ID NO:69;
(b) a heavy chain variable region comprising the CDR1, CDR2, and CDR3 sequences as set forth in SEQ ID NO:45, and a light chain variable region comprising the CDR1, CDR2, and CDR3 sequences as set forth in SEQ ID NO:69;
(c) a heavy chain variable region comprising the CDR1, CDR2, and CDR3 sequences as set forth in SEQ ID NO:46, and a light chain variable region comprising the CDR1, CDR2, and CDR3 sequences as set forth in SEQ ID NO:69;
(d) a heavy chain variable region comprising the CDR1, CDR2, and CDR3 sequences as set forth in SEQ ID NO:47, and a light chain variable region comprising the CDR1, CDR2, and CDR3 sequences as set forth in SEQ ID NO:69;
(e) a heavy chain variable region comprising the CDR1, CDR2, and CDR3 sequences as set forth in SEQ ID NO:48, and a light chain variable region comprising the CDR1, CDR2, and CDR3 sequences as set forth in SEQ ID NO:69;
(f) a heavy chain variable region comprising the CDR1, CDR2, and CDR3 sequences as set forth in SEQ ID NO:49, and a light chain variable region comprising the CDR1, CDR2, and CDR3 sequences as set forth in SEQ ID NO:69;
(g) a heavy chain variable region comprising the CDR1, CDR2, and CDR3 sequences as set forth in SEQ ID NO:50, and a light chain variable region comprising the CDR1, CDR2, and CDR3 sequences as set forth in SEQ ID NO:69;
(h) a heavy chain variable region comprising the CDR1, CDR2, and CDR3 sequences as set forth in SEQ ID NO:51, and a light chain variable region comprising the CDR1, CDR2, and CDR3 sequences as set forth in SEQ ID NO:69;
(i) CDR1, CDR2, and CDR3 sequences as set forth in a heavy chain variable region sequence SEQ ID NO:54, and a light chain variable region comprising the CDR1, CDR2, and CDR3 sequences as set forth in SEQ ID NO:69;
(j) a heavy chain variable region comprising the CDR1, CDR2, and CDR3 sequences as set forth in SEQ ID NO:55, and a light chain variable region comprising the CDR1, CDR2, and CDR3 sequences as set forth in SEQ ID NO:69;
(k) a heavy chain variable region comprising the CDR1, CDR2, and CDR3 sequences as set forth in SEQ ID NO:57, and a light chain variable region comprising the CDR1, CDR2, and CDR3 sequences as set forth in SEQ ID NO:69;
or
(l) a heavy chain variable region comprising the CDR1, CDR2, and CDR3 sequences as set forth in SEQ ID NO:58, and a light chain variable region comprising the CDR1, CDR2, and CDR3 sequences as set forth in SEQ ID NO:69.
In some embodiments, the anti-Siglec-7 antibody has ligand blocking activity; and/or has a $K_D$ of less than about 100 pM when measured as a monovalent Fab; and/or has an internalization activity of less than about 100 pM. In some embodiments, the anti-Siglec-7 antibody has a $K_D$ of less than about 75 pM when measured as a monovalent Fab. In some embodiments, the anti-Siglec-7 antibody has an internalization activity of about 70 pM or less. In some embodiments, the anti-Siglec-7 antibody has an internalization activity of less than about 25 pM.

In an additional aspect, provided herein is an anti-Siglec-7 antibody that comprises:
a) a heavy chain variable region comprising the CDR1, CDR2, and CDR3 sequences as set forth in SEQ ID NO:53; and a light chain variable region comprising the CDR1, CDR2, and CDR3 sequences as set forth in SEQ ID NO:78;
(b) heavy chain variable region comprising the CDR1, CDR2, and CDR3 sequences as set forth in SEQ ID NO:54; and a light chain variable region comprising the CDR1, CDR2, and CDR3 sequences as set forth in SEQ ID NO:78;
(c) heavy chain variable region comprising the CDR1, CDR2, and CDR3 sequences as set forth in SEQ ID NO:51; and a light chain variable region comprising the CDR1, CDR2, and CDR3 sequences as set forth in SEQ ID NO:78;
(d) heavy chain variable region comprising the CDR1, CDR2, and CDR3 sequences as set forth in SEQ ID NO:55; and a light chain variable region comprising the CDR1, CDR2, and CDR3 sequences as set forth in SEQ ID NO:78;
(e) heavy chain variable region comprising the CDR1, CDR2, and CDR3 sequences as set forth in SEQ ID NO:58; and a light chain variable region comprising the CDR1, CDR2, and CDR3 sequences as set forth in SEQ ID NO:78;
or
(f) heavy chain variable region comprising the CDR1, CDR2, and CDR3 sequences as set forth in SEQ ID NO:59; and a light chain variable region comprising the CDR1, CDR2, and CDR3 sequences as set forth in SEQ ID NO:78.
In some embodiments, the anti-Siglec-7 antibody has ligand blocking activity; and/or has a $K_D$ of less than about 100 pM when measured as a monovalent Fab; and/or has an internalization activity of less than about 100 pM. In some embodiments, the anti-Siglec-7 antibody has a $K_D$ of less than about 75 pM when measured as a monovalent Fab. In some embodiments, the anti-Siglec-7 antibody has an internalization activity of about 70 pM or less. In some embodiments, the anti-Siglec-7 antibody has an internalization activity of less than about 25 pM.

In a further aspect, provided herein is an anti-Siglec-7 antibody that comprises:
a) a heavy chain variable region comprising the amino acid sequence SEQ ID NO:43 and a light chain variable region comprising the amino acid sequence of SEQ ID NO:69;
(b) a heavy chain variable region comprising the amino acid sequence of SEQ ID NO:45 and a light chain variable region comprising the amino acid sequence of SEQ ID NO:69;
(c) a heavy chain variable region comprising the amino acid sequence of SEQ ID NO:46 and a light chain variable region comprising the amino acid sequence of SEQ ID NO:69;

(d) a heavy chain variable region comprising the amino acid sequence of SEQ ID NO:47 and a light chain variable region comprising the amino acid sequence of SEQ ID NO:69;
(e) a heavy chain variable region comprising the amino acid sequence of SEQ ID NO:48 and a light chain variable region comprising the amino acid sequence of SEQ ID NO:69;
(f) a heavy chain variable region comprising the amino acid sequence of SEQ ID NO:49 and a light chain variable region comprising the amino acid sequence of SEQ ID NO:69;
(g) a heavy chain variable region comprising the amino acid sequence of SEQ ID NO:50 and a light chain variable region comprising the amino acid sequence of SEQ ID NO:69;
(h) a heavy chain variable region comprising the amino acid sequence of SEQ ID NO:51 and a light chain variable region comprising the amino acid sequence of SEQ ID NO:69;
(i) a heavy chain variable region comprising the amino acid sequence of SEQ ID NO:54 and a light chain variable region comprising the amino acid sequence of SEQ ID NO:69;
(j) a heavy chain variable region comprising the amino acid sequence of SEQ ID NO:55 and a light chain variable region comprising the amino acid sequence of SEQ ID NO:69;
(k) a heavy chain variable region comprising the amino acid sequence of SEQ ID NO:57 and a light chain variable region comprising the amino acid sequence of SEQ ID NO:69; or
(l) a heavy chain variable comprising the amino acid sequence of SEQ ID NO:58 and a light chain variable region comprising the amino acid sequence of SEQ ID NO:69. In some embodiments, the anti-Siglec-7 antibody has ligand blocking activity; and/or has a $K_D$ of less than about 100 pM when measured as a monovalent Fab; and/or has an internalization activity of less than about 100 pM. In some embodiments, the anti-Siglec-7 antibody has a $K_D$ of less than about 75 pM when measured as a monovalent Fab. In some embodiments, the anti-Siglec-7 antibody has an internalization activity of about 70 pM or less. In some embodiments, the anti-Siglec-7 antibody has an internalization activity of less than about 25 pM.

In an additional aspect, provided herein is an anti-Siglec-7 antibody that comprises:
a) a heavy chain variable region comprising the amino acid sequence of SEQ ID NO:53 and a light chain variable region comprising the amino acid sequence of SEQ ID NO:78;
(b) heavy chain variable region comprising the amino acid sequence of SEQ ID NO:54 and a light chain variable region comprising the amino acid sequence of SEQ ID NO:78;
(c) heavy chain variable region comprising the amino acid sequence of SEQ ID NO:51 and a light chain variable region comprising the amino acid sequence of SEQ ID NO:78;
(d) heavy chain variable region comprising the amino acid sequence of SEQ ID NO:55 and a light chain variable region comprising the amino acid sequence of SEQ ID NO:78;
(e) heavy chain variable region comprising the amino acid sequence of SEQ ID NO:58 and a light chain variable region comprising the amino acid sequence of SEQ ID NO:78; or
(f) heavy chain variable region comprising the amino acid sequence of SEQ ID NO:59 and a light chain variable region comprising the amino acid sequence of SEQ ID NO:78. In some embodiments, the anti-Siglec-7 antibody has ligand blocking activity; and/or has a $K_D$ of less than about 100 pM when measured as a monovalent Fab; and/or has an internalization activity of less than about 100 pM. In some embodiments, the anti-Siglec-7 antibody has a $K_D$ of less than about 75 pM when measured as a monovalent Fab. In some embodiments, the anti-Siglec-7 antibody has an internalization activity of about 70 pM or less. In some embodiments, the anti-Siglec-7 antibody has an internalization activity of less than about 25 pM.

In some embodiments, the anti-Siglec-7 antibody of the disclosure as described in the foregoing paragraphs is in a monovalent format, or an antibody fragment format, such as an Fv, Fab, Fab', scFv, diabody, or F(ab')$_2$ fragment.

In some embodiments, the anti-Siglec-7 antibody of the disclosure as described in the foregoing paragraphs is a multivalent form or bivalent form. In some embodiments, the antibody isn IgG, such as an IgG1, IgG2, IgG3, or IgG4.

In a further aspect, the invention provides a bispecific or multi-specific antibody that comprises an antibody of any one of the foregoing embodiments.

In an additional aspect, the invention provides a method of inhibiting proliferation of tumor cells, the method comprising administering a therapeutically effective amount of an antibody of any of the antibodies described in the foregoing paragraphs, or a bispecific or multi-specific antibody comprising such an antibody, to a patient that has a tumor that expresses sialylated Siglec-7 ligands. In some embodiments, the tumor expresses sialylated Siglec-7 ligands in an amount above that which is detected in normal cells of the corresponding cell type. In some embodiments, the tumor comprises an elevated level of CD8+ infiltrating T cells that express Siglec-7.

In a further aspect, the invention provides a method of identifying a patient that is a candidate for treatment with an anti-Siglec-7 antibody, the method comprising determining the proportion of CD8+ T cells that have infiltrated a tumor, or a metastatic lesion, that express detectable Siglec-7 on the cell surface. In some embodiments, a patient that has a tumor that is a candidate for treatment with an anti-Siglec-7 antibody, has at least 10% or at least 20%, or greater of tumor-infiltrating CD8+ T cells in the tumor or a metastatic lesion that express detectable Siglec-7 on the cell surface. In some embodiments, the level of Siglec-7 expression is determined using an anti-Siglec-7 antibody. In some embodiments, the level of expression is determined by flow cytometry or immunohistochemistry.

The disclosure additionally provides a method of identifying a patient that has a tumor that is a candidate for treatment with an anti-Siglec-7 antibody, the method comprising determining the proportion of CD8+ infiltrating T cells in a tumor or metastatic lesion that express detectable Siglec-7, wherein a patient that has a tumor or metastatic lesion in which at least 10%, or at least 20%, of infiltrating CD8+ T express Siglec-7 is a candidate for treatment with an anti-Siglec-7 antibody. In some embodiments, the level of Siglec-7 expression is determined using an anti-Siglec-7 antibody. In some embodiments, the level of expression is determined by flow cytometry or immunohistochemistry.

In a further aspect, the disclosure provides a method of inhibiting proliferation of tumor cells, the method comprising administering a therapeutically effective amount of an anti-Siglec-7 antibody to a patient that has cancer, wherein the patient has a primary tumor or metastatic lesion that comprises an elevated level of CD8+ infiltrating-T cells that express Siglec-7; and further, wherein the tumor or metastatic lesion comprises cancer cells that express sialylated Siglec-7 ligands, e.g., express sialyated Siglec-7 ligands at a level higher than normal tissue. In some embodiments, the anti-Siglec-7 antibody has a $K_D$ of 70 pM or less when measured as a monovalent Fab.

In a further aspect, the disclosure further provides use of an anti-Siglec-7 antibody as described herein in a method of treating a cancer as described herein.

BRIEF DESCRIPTION OF THE DRAWINGS

FIG. 1 provides illustrative heavy chain variable region sequences of anti-Siglec-7 antibodies of the invention. The CDRs as defined by Kabat are underlined.

FIG. 2 provides illustrative heavy chain variable region sequences of anti-Siglec-7 antibodies of the invention. The CDRs as defined by Chothia are underlined.

FIG. 3 provides illustrative light chain variable region sequences of anti-Siglec-7 antibodies of the invention. The CDRs as defined by both Kabat and Chothia are underlined.

FIG. 10 provides data illustrating rapid concentration-dependent, antibody-induced internalization of Siglec-7 on human NK cells using an antibody of the present disclosure.

FIG. 11 provides data illustrating non-ligand blocking, internalization activity of an antibody of the present disclosure.

DETAILED DESCRIPTION OF ASPECTS OF THE DISCLOSURE

Terminology

Figure 4:
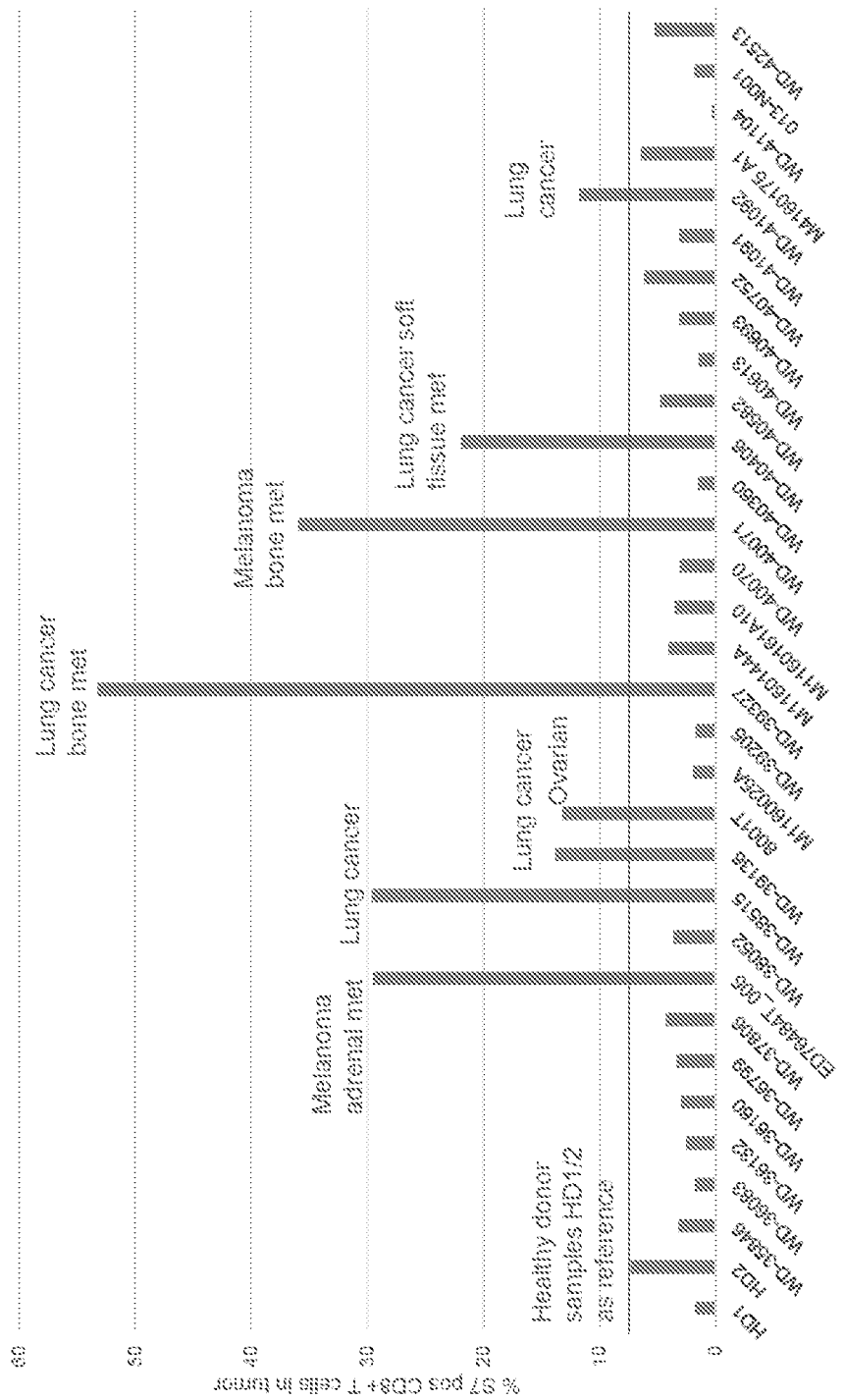
FIG. 4 provides illustrative data showing that Siglec-7 is detected on a high percentage of tumor-infiltrating CD8+ cells in fresh primary tumors.

As used in herein, the singular forms "a", "an" and "the" include plural referents unless the content clearly dictates otherwise. Thus, for example, reference to "an antibody" optionally includes a combination of two or more such molecules, and the like.

The term "about" as used herein refers to the usual error range for the respective value readily known to the skilled person in this technical field, for example ±20%, ±10%, or ±5%, are within the intended meaning of the recited value.

Siglec-7, also known as p75 or AIRM, is a member of the sialic acid-binding lectins (Siglec) of the immunoglobulin (Ig) superfamily. Siglec receptors bind glycans containing sialic acid, but differ in their recognition of specific carbohydrate structures. A human Siglec-7 protein sequence available under accession number NP_055200.1 is The term "antibody" is used herein in the broadest sense and encompasses various antibody structures, including but not limited to monoclonal antibodies, polyclonal antibodies, multispecific antibodies, such as bispecific antibodies, and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules, such as scFv molecules; and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation.

(SEQ ID NO: 108)

```
  1  mlllllpll  wgrervegqk  snrkdysltm  qssvtvqegm  cvhvrcsfsy  pvdsqtdsdp 61  vhgywfragn  diswkapvat  nnpawavqee  trdrfhllgd  pqtknctlsi  rdarmsdagr 121  yffrmekgni  kwnykydqls  vnvtalthrp  nilipgtles  gcfqnltcsv  pwaceqgtpp 181  miswmgtsvs  plhpsttrss  vltlipqpqh  hgtsltcqvt  lpgagvttnr  tiqlnvsypp 241  qnltvtvfqg  egtastalgn  ssslsvlegq  slrlvcavds  npparlswtw  rsltlypsqp 301  snplvlelqv  hlgdegeftc  raqnslgsqh  vslnlslqqe  ytgkmrpvsg  vllgavggag 361  atalvflsfc  vifivvrscr  kksarpaadv  gdigmkdant  irgsasqgnl  teswaddnpr 421  hhglaahssg  eereiqyapl  sfhkgepqdl  sgqeatnney  seikipk.
```

As used herein, "complementarity-determining region (CDR)" refers to the three hypervariable regions (HVRs) in each chain that interrupt the four "framework" regions established by the light and heavy chain variable regions. The CDRs are the primary contributors to binding to an epitope of an antigen. The CDRs of each chain are referred to as CDR1, CDR2, and CDR3, numbered sequentially starting from the N-terminus, and are also identified by the chain in which the particular CDR is located. Thus, a VH CDR3 is located in the variable domain of the heavy chain of the antibody in which it is found, whereas a $V_L$ CDR1 is the CDR1 from the variable domain of the light chain of the antibody in which it is found. The term "CDR" may be used interchangeably with "HVR".

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., J. Mol. Biol 1997, 273(4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29(1):207-9 (2001); MacCallum et al, Antibody-antigen interactions: Contact analysis and binding site topography, J. Mol. Biol., 262 (5), 732-745 (1996); and Martin et al, Proc. Natl Acad. Sci. USA, 86, 9268-9272 (1989); Martin, et al, Methods Enzymol., 203, 121-153, (1991); Pedersen et al, Immunomethods, 1, 126, (1992); and Rees et al, In Stemberg M. J. E. (ed.), Protein Structure Prediction. Oxford University Press, Oxford, 141-172 1996). Reference to CDRs as determined by Kabat numbering are based, for example, on Kabat et al., Sequences of Proteins of Immunological Interest, 5th Ed. Public Health Service, National Institute of Health, Bethesda, Md. (1991)). Chothia CDRs are determined as defined by Chothia (see, e.g., Chothia and Lesk J. Mol. Biol. 196:901-917 (1987)).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

As used herein, "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

An "Fc region" refers to the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ. It is understood in the art that the boundaries of the Fc region may vary, however, the human IgG heavy chain Fc region is usually defined to comprise residues C226 or P230 to its carboxyl-terminus, using the numbering according to the EU index as in Kabat et al. (1991, NIH Publication 91-3242, National Technical Information Service, Springfield, Va.). The term "Fc region" may refer to this region in isolation or this region in the context of an antibody or antibody fragment. "Fc region" includes naturally occurring allelic variants of the Fc region as well as modifications that modulate effector function. Fc regions also include variants that don't result in alterations to biological function. For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, et al., *Science* 247:306-1310, 1990). For example, for IgG4 antibodies, a single amino acid substitution (S228P according to Kabat numbering; designated IgG4Pro) may be introduced to abolish the heterogeneity observed in recombinant IgG4 antibody (see, e.g., Angal, et al., *Mol Immunol* 30:105-108, 1993).

The term "equilibrium dissociation constant" abbreviated ($K_D$), refers to the dissociation rate constant ($k_d$, time$^{-1}$) divided by the association rate constant ($k_a$, time$^{-1}$ M$^{-1}$).

Equilibrium dissociation constants can be measured using any method. Thus, in some embodiments antibodies of the present disclosure have a $K_D$ of less than about 50 nM, typically less than about 25 nM, or less than 10 nM, e.g., less than about 5 nM or than about 1 nM and often less than about 10 nM as determined by surface plasmon resonance analysis using a biosensor system such as a Biacore® system performed at 37° C. In some embodiments, an antibody of the present disclosure has a $K_D$ of less than $5\times10^{-5}$ M, less than $10^{-5}$ M, less than $5\times10^{-6}$ M, less than $10^{-6}$ M, less than $5\times10^{-7}$ M, less than $10^{-7}$ M, less than $5\times10^{-8}$ M, less than $10^{-8}$ M, less than $5\times10^{-9}$ M, less than $10^{-9}$ M, less than $5\times10^{-10}$ M, less than $10^{-10}$ M, less than $5\times10^{-11}$ M, less than $10^{-11}$ M, less than $5\times10^{-12}$ M, less than $10^{-12}$ M, less than $5\times10^{-13}$ M, less than $10^{-13}$ M, less than $5\times10^{-14}$ M, less than $10^{-14}$ M, less than $5\times10^{-15}$ M, or less than $10^{-15}$ M or lower as measured as a bivalent antibody. In the context of the present invention, an "improved" $K_D$ refers to a lower $K_D$. In some embodiments, an antibody of the present disclosure has a $K_D$ of less than $5\times10^{-5}$ M, less than $10^{-5}$ M, less than $5\times10^{-6}$ M, less than $10^{-6}$ M, less than $5\times10^{-7}$ M, less than $10^{-7}$ M, less than $5\times10^{-8}$ M, less than $10^{-8}$ M, less than $5\times10^{-9}$ M, less than $10^{-9}$ M, less than $5\times10^{-10}$ M, less than $10^{-10}$ M, less than $5\times10^{-11}$ M, less than $10^{-11}$ M, less than $5\times10^{-12}$ M, less than $10^{-12}$ M, less than $5\times10^{-13}$ M, less than $10^{-13}$ M, less than $5\times10^{-14}$ M, less than $10^{-14}$ M, less than $5\times10^{-15}$ M, or less than $10^{-15}$ M or lower as measured as a monovalent antibody, typically a monovalent Fab. In some embodiments, an anti-Siglec-7 antibody of the present disclosure has $K_D$ less than 100 pM, e.g., or less than 75 pM, e.g., in the range of 1 to 100 pM, when measured as a monovalent Fab by surface plasmon resonance analysis using a biosensor system such as a Biacore® system performed at 37° C. In some embodiments, an anti-Siglec-7 antibody of the present disclosure has $K_D$ less than 500 pM, e.g., in the range of 1 to 500 pM, or 1 to 200, or 1 to 250 pM, when measured as a monovalent Fab by surface plasmon resonance analysis using a biosensor system such as a Biacore® system performed at 37° C. In the context of the present invention, an "improved" $K_D$ refers to a lower $K_D$.

The term "monovalent molecule" as used herein refers to a molecule that has one antigen-binding site, e.g., a Fab.

The term "bivalent molecule" as used herein refers to a molecule that has two antigen-binding sites. In some embodiments, a bivalent molecule of the present invention is a bivalent antibody or a bivalent fragment thereof. In some embodiments, a bivalent molecule of the present invention is a bivalent antibody. In some embodiments, a bivalent molecule of the present invention is an IgG. In general monoclonal antibodies have a bivalent basic structure. IgG and IgE have only one bivalent unit, while IgA and IgM consist of multiple bivalent units (2 and 5, respectively) and thus have higher valencies. This bivalency increases the avidity of antibodies for antigens.

The terms "monovalent binding" or "monovalently binds to" as used herein refer to the binding of one antigen-binding site to its antigen.

The terms "bivalent binding" or "bivalently binds to" as used herein refer to the binding of both antigen-binding sites of a bivalent molecule to its antigen. Preferably both antigen-binding sites of a bivalent molecule share the same antigen specificity.

The term "valency" as used herein refers to the number of different binding sites of an antibody for an antigen. A monovalent antibody comprises one binding site for an antigen. A bivalent antibody comprises two binding sites for the same antigen.

The term "avidity" as used herein in the context of antibody binding to an antigen refers to the combined binding strength of multiple binding sites of the antibody. Thus, "bivalent avidity" refers to the combined strength of two binding sites.

The phrase "specifically (or selectively) binds" to an antigen or target or "specifically (or selectively) immunoreactive with," when referring to a protein or peptide, refers to a binding reaction whereby the antibody binds to the antigen or target of interest. In the context of this invention, the antibody binds to SIGLEC-7 with a $K_D$ that is at least 100-fold greater than its affinity for other antigens.

The terms "identical" or percent "identity," in the context of two or more polypeptide sequences, refer to two or more sequences or subsequences that are the same or have a specified percentage of amino acid residues that are the same (e.g., at least 70%, at least 75%, at least 80%, 85%, 90%, 91%, 92%, 93%, 94%, 95%, 96%, 97%, 98%, 99%, or higher) identity over a specified region, when compared and aligned for maximum correspondence over a comparison window or designated region. Alignment for purposes of determining percent amino acid sequence identity can be performed in various methods, including those using publicly available computer software such as BLAST, BLAST-2, ALIGN or Megalign (DNASTAR) software. Examples examples of algorithms that are suitable for determining percent sequence identity and sequence similarity the BLAST 2.0 algorithms, which are described in Altschul et al., Nuc. Acids Res. 25:3389-3402 (1977) and Altschul et al., J. Mol. Biol. 215:403-410 (1990). Thus, BLAST 2.0 can be used with the default parameters described to determine percent sequence.

A "conservative" substitution as used herein refers to a substitution of an amino acid such that charge, hydrophobicity, and/or size of the side group chain is maintained. Illustrative sets of amino acids that may be substituted for one another include (i) positively-charged amino acids Lys, Arg and His; (ii) negatively charged amino acids Glu and Asp; (iii) aromatic amino acids Phe, Tyr and Trp; (iv) nitrogen ring amino acids His and Trp; (v) large aliphatic nonpolar amino acids Val, Leu and Ile; (vi) slightly polar amino acids Met and Cys; (vii) small-side chain amino acids Ser, Thr, Asp, Asn, Gly, Ala, Glu, Gln and Pro; (viii) aliphatic amino acids Val, Leu, Ile, Met and Cys; and (ix) small hydroxyl amino acids Ser and Thr. Reference to the charge of an amino acid in this paragraph refers to the charge at physiological pH.

Anti-Siglec-7 Antibodies

Anti-Siglec-7 antibodies of the invention have improved binding characteristics compared to known anti-Siglec 7 antibodies, such as improved internalization activity and/or improved ligand-blocking activity. In some embodiments, an antibody of the invention has internalizing activity, but does not block ligand binding.

An antibody of the invention typically has a lower $K_D$ when compared to known anti-Siglec 7 monoclonal antibodies such as Z176, QA79, and S7.7. In some embodiments, an antibody of the invention has a $K_D$ of less than about 100 pM, or less than about 75 pM, or less than about 50 pM, or less than about 40 pM or less than about 35 pM. In some embodiments, an antibody of the invention has a $K_D$ of about 1 pM or less. In some embodiments, an antibody of the invention has at least one, at least two, or three CDRs of a $V_H$ sequence of the antibody designated as 16H11, 3F1, SL9, 8A2, 5D1, or 5G10 in FIG. 1 or FIG. 2. In some embodiments, an antibody of the invention that has an improved $K_D$ has at least one, at least two, or three CDRs of a $V_L$ sequence of the antibody designated as 16H11, 3F1, SL9, 8A2, 5D1, or 5G10 in FIG. 3. In embodiments has six CDRs of an antibody designated as 16H11, 3F1, SL9, 8A2, 5D1, or 5G10 in FIGS. 1-3.

In some embodiments, has an enhanced ability to block ligand binding compared to previously characterized anti-Siglec 7 monoclonal antibodies. In the context of the present invention, the ability to block ligand binding refers to the concentration of monoclonal antibody at which 50% of Siglec-7 does not bind ligand. In some embodiments, an antibody of the invention is more potent in ligand-blocking activity, i.e., the $IC_{50}$ for an antibody for ligand blocking, is lower than that of a known antibody, such as such as Z176, QA79, and S7. Ligand blocking activity can be assessed using known assays. For example, ligand blocking activity may be determined using a cell line, such as the human melanoma cell line A375, that expresses high levels of ligands for Siglec-7 on the cell surface. $IC_{50}$ values for blocking can be determined, for example, as explained in the examples section. In some embodiments, an antibody of the invention that has improved ligand blocking activity has an IC50 of less than 4000 pM, or less than about 3500 pM or less than about 3000 pM or less than about 2000 pM or less than about 1500 pM or less than about 1000 pM or about 500 pM or less when assayed under the assay conditions described in the Examples section. In some embodiments, an antibody of the invention that exhibits improved ligand blocking activity has at least one, at least two, or three CDRs of a $V_H$ sequence of the antibody designated as 9D4, SL13, or 5G10 in FIG. 1 or FIG. 2. In some embodiments, an antibody of the invention has at least one, at least two, or three CDRs of a $V_L$ sequence of the antibody designated as 9D4, SL13, or 5G10 in FIG. 3. In embodiments has six CDRs of an antibody designated as 9D4, SL13, or 5G10 in FIGS. 1-3.

In some embodiments, an anti-Siglec-7 antibody of the present invention exhibits improved internalization compared to previously characterized anti-Siglec-7 monoclonal antibodies. In the present disclosure, internalization activity refers to the concentration of antibody at which 50% of Siglec-7 is internalized in 24 hours on healthy donor Natural Killer (NK) cells. In the context of the present invention, an "enhanced" or "improved" internalization activity means that the $IC_{50}$ for internalization is lower than that of a known antibody, such as such as Z176, QA79, and S7. Internalization can be assessed using known assays. For example, PBMC obtained from healthy donors may be used to determine internalization activity of anti-Siglec-7 antibodies. $IC_{50}$ values for internalization can be determined, for example, as described in the Examples section. In some embodiments, an antibody of the invention has an internalizing IC50 of less than about 70 pM, In some embodiments, an antibody has an internalizing IC50 of less than about 60 pM, or less than about 50 pM, or less than about 40 pM, or less than about 30 pM, or less than about 25 pM, or less than about 20, or less than about 10 pM when assayed under the assay conditions described in the Examples section. In some embodiments, an antibody of the invention having an improved internalization activity has at least one, at least two, or three CDRs of a $V_H$ sequence of the antibody designated as 3F1, SL9, 16H11, 8A2, SL2, 5D1, or 10E11 in FIG. 1 or FIG. 2. In some embodiments, an antibody of the invention has at least one, at least two, or three CDRs of a $V_L$ sequence of the antibody designated as 3F1, SL9, 16H11, 8A2, SL2, 5D1, or 10E11 in FIG. 3. In embodiments has six CDRs of an antibody designated as 3F1, SL9, 16H11, 8A2, SL2, 5D1, or 10E11 in FIGS. 1-3. In some embodiments, an antibody of the invention having an improved internalization activity has at least one, at least two, or three CDRs of a $V_H$ sequence of the antibody designated as 3F1 or 16H11 in FIG. 1 or FIG. 2. In some embodiments, an antibody of the invention has at least one, at least two, or three CDRs of a $V_L$ sequence of the antibody designated as 3F1 or 16H11 in FIG. 3. In embodiments has six CDRs of an antibody designated as 9D4, SL13, or 5G10 in FIGS. 1-3.

In some embodiments, an anti-Siglec 7 antibody of the present invention, internalizes Siglec-7, but does not block binding of the Siglec-7 ligand to Siglec-7. In the context of the present invention, an antibody that does not block binding of ligand to Siglec-7 refers to an antibody that does not result in more than a 25% reduction in ligand binding when assayed under conditions as explained in the Examples section. In some embodiments, an antibody of the invention that internalizes Siglec-7 ligand, but does not block ligand binding to Siglec-7 has at least one, at least two, or three CDRs of a $V_H$ sequence of the antibody designated as 4B12 or 8A2 in FIG. 1 or FIG. 2. In some embodiments, an antibody of the invention has at least one, at least two, three CDRs of a $V_L$ sequence of the antibody designated as 4B12 or 8A2 in FIG. 3. In embodiments has six CDRs of an antibody designated as 4B12 or 8A2 in FIGS. 1-3.

In some embodiments, an anti-Siglec 7 antibody of the present invention binds to distinct epitopes relative to described anti-Siglec-7 antibodies such as such as Z176, QA79, and S7. Z176, and S7.7 are commercially available anti-Siglec-7 antibodies. QA79 is commercially available from eBiosciences. The hybridoma that produces QA79 is also available under ICLC accession number PD99003. Z176 is available from Beckman Coulter and S7.7 is available from BioLegend.

In some embodiments an antibody of the present invention does not compete with any of Z176, QA79, and S7 for binding to Siglec-7 ligand. In some embodiments, an antibody of the present invention competes with an antibody designated as 4B12 in FIGS. 1-3 for binding to Siglec-7. In some embodiments, an antibody of the invention has at least one, at least two, or three CDRs of a $V_H$ sequence of the antibody designated as 4B12 in FIG. 1 or FIG. 2. In some embodiments, an antibody of the invention has at least one, at least two, or three CDRs of a $V_L$ sequence of the antibody designated as 4B12 in FIG. 3. In embodiments has six CDRs of an antibody designated as 4B12 in FIGS. 1-3.

In some embodiments, an anti-Siglec-7 antibody of the present invention that binds to an epitope comprising W132 such that a W132A mutation compromises binding activity. In some embodiments, such an antibody competes with an antibody designated as 2G12 in FIGS. 1-3 for binding to Siglec-7. In some embodiments, such an antibody competes with an antibody designated as 2G12 in FIGS. 1-3 for binding to Siglec-7 ligand. In some embodiments, an antibody of the invention has at least one, at least two, or three CDRs of a $V_H$ sequence of the antibody designated as 2G121 in FIG. 1 or FIG. 2. In some embodiments, an antibody of the invention has at least one, at least two, or three CDRs of a $V_L$ sequence of the antibody designated as 2G12 in FIG. 3. In embodiments has six CDRs of an antibody designated as 2G12 in FIGS. 1-3.

In some embodiments, an anti-Siglec-7 antibody of the present invention competes with an antibody designated as 5D1 in FIGS. 1-3 for binding to Siglec-7. In some embodiments, such an antibody competes with an antibody designated as 2G12 in FIGS. 1-3 for binding to Siglec-7 ligand. In some embodiments, an antibody of the invention has at least one, at least two, or three CDRs of a $V_H$ sequence of the antibody designated as 5D1 in FIG. 1 or FIG. 2. In some embodiments, an antibody of the invention has at least one, at least two, or three CDRs of a $V_L$ sequence of the antibody designated as 5D1 in FIG. 3. In embodiments has six CDRs of an antibody designated as 5D1 in FIGS. 1-3.

In some embodiments, an anti-Siglec-7 antibody of the present invention competes with an antibody designated as 8A2 in FIGS. 1-3 for binding to Siglec-7. In some embodiments, an antibody of the invention has at least one, at least two, or three CDRs of a $V_H$ sequence of the antibody designated as 8A2 in FIG. 1 or FIG. 2. In some embodiments, an antibody of the invention has at least one, at least two, or three CDRs of a $V_L$ sequence of the antibody designated as 8A2 in FIG. 3. In embodiments has six CDRs of an antibody designated as 8A2 in FIGS. 1-3.

In some embodiments, an anti-Siglec-7 antibody of the invention comprises at least one, two, or three CDRs selected from a heavy chain variable amino acid sequence set forth in FIG. 1 or FIG. 2. In some embodiments, an anti-Siglec-7 antibody of the invention comprise one, two, or three CDRs selected from a light chain variable region set forth in FIG. 3. In some embodiments, an anti-Siglec-7 antibody comprises an HCDR3 selected from the HCDR3 sequence presented in FIG. 1 and an LCDR3 selected from the LCDR3 sequences presented in FIG. 3.

In some embodiments, an anti-Siglec-7 antibody of the present invention competes with an antibody designated as 16H11 in FIGS. 1-3 for binding to Siglec-7. In some embodiments, an antibody of the invention has at least one, at least two, or three CDRs of a $V_H$ sequence of the antibody designated as 8A2 in FIG. 1 or FIG. 2. In some embodiments, an antibody of the invention has at least one, at least two, or three CDRs of a $V_L$ sequence of the antibody designated as 8A2 in FIG. 3. In embodiments has six CDRs of an antibody designated as 8A2 in FIGS. 1-3.

In some embodiments, an anti-Siglec-7 antibody of the present invention comprises a heavy chain variable region having at least 80%, 85%, 90%, 91%, 92%, 93%, 94%, 95%, 96%, 97%, 98%, 99%, or 100% sequence identity to the amino acid sequence of a heavy chain variable region of FIG. 1. In certain embodiments, a $V_H$ sequence having at least 80%, 85%, 90%, 91%, 92%, 93%, 94%, 95%, 96%, 97%, 98%, or 99% identity to the amino acid sequence of a heavy chain variable region of FIG. 1 or FIG. 2 contains substitutions (e.g., conservative substitutions), insertions, or deletions relative to the reference sequence, but an anti-Siglec-7 antibody comprising that sequence retains the ability to bind to Siglec-7. In certain embodiments, a total of 1 to 20 amino acids have been substituted, inserted and/or deleted in the amino acid sequence of a heavy chain variable region of FIG. 1. In certain embodiments, the substitutions, insertions, or deletions occur in the framework regions.

In some embodiments, an anti-Siglec-7 antibody of the present invention comprises a light chain variable region having at least 80%, 85%, 90%, 91%, 92%, 93%, 94%, 95%, 96%, 97%, 98%, 99%, or 100% sequence identity to the amino acid sequence of a light chain variable region of FIG. 3. In certain embodiments, a $V_L$ sequence having at least 80%, 85%, 90%, 91%, 92%, 93%, 94%, 95%, 96%, 97%, 98%, or 99% identity to the amino acid sequence of a light chain variable region of FIG. 3 contains substitutions (e.g., conservative substitutions), insertions, or deletions relative to the reference sequence, but an anti-Siglec-7 antibody comprising that sequence retains the ability to bind to Siglec-7. In certain embodiments, a total of 1 to 20 amino acids have been substituted, inserted and/or deleted in the amino acid sequence of a light chain variable region of FIG. 3. In certain embodiments, the substitutions, insertions, or deletions occur in the framework regions.

In some embodiments, an anti-Siglec-7 antibody of the present invention comprises a heavy chain variable region having at least 80%, 85%, 90%, 91%, 92%, 93%, 94%, 95%, 96%, 97%, 98%, 99%, or 100% sequence identity to the amino acid sequence of a heavy chain variable region of FIG. 1 or FIG. 2; and a light chain variable region of the corresponding antibody of FIG. 3, where the light chain variable region has at least 80%, 85%, 90%, 91%, 92%, 93%, 94%, 95%, 96%, 97%, 98%, 99%, or 100% sequence identity to the amino acid sequence of the light chain variable region of FIG. 3. In some embodiments, the anti-Siglec-7 antibody has a modification to the heavy chain variable region and/or the light chain variable region as described in the preceding two paragraphs.

In some embodiments, an anti-Siglec-7 antibody comprises a heavy chain variable region that comprises a CDR3 as set forth in FIG. 1 in which 1, 2, or 3 amino acids are substituted, e.g., conservatively substituted. In some embodiments, a heavy chain variable region comprises three CDRs of a variable region sequence set forth in FIG. 1 in which the CDR1 has 1, 2, or 3 amino acid substitutions and/or the CDR2 has at least 1, 2, 3, 4, 5, 6, 7, or 8 amino acid substitutions. In some embodiments, a heavy chain variable region comprises three CDRs of a variable region sequence set forth in FIG. 2 in which the CDR1 has 1, 2, 3, or 4 amino acid substitutions and/or the CDR2 has at least 1, 2, or 3 amino acid substitutions.

In some embodiments, an anti-Siglec-7 antibody comprises a heavy chain variable region that comprises a CDR3 as set forth in FIG. 2 in which 1, 2, or 3 amino acids are substituted, e.g., conservatively substituted. In some embodiments, such a heavy chain variable region comprises three CDRs of a variable region sequence set forth in FIG. 2 in which the CDR1 has 1, 2, or 3 amino acid substitutions and/or the CDR2 has at least 1, 2, 3, 4, 5, 6, 7, or 8 amino acid substitutions; or comprises three CDRs of a variable region sequence set forth in FIG. 2 in which the CDR1 has 1, 2, 3, or 4 amino acid substitutions and/or the CDR2 has at least 1, 2, or 3 amino acid substitutions.

In some embodiments, an anti-Siglec-7 antibody comprises a light chain variable region comprising a CDR3 as set forth in FIG. 3 in which 1, 2, or 3 amino acids are substituted, e.g., conservatively substituted. In some embodiments, a light chain variable region comprises three CDRs of a variable region sequence set forth in FIG. 3 in which the CDR1 and/or the CDR2 have at least 1, 2, 3, or 4 amino acid substitutions.

In some embodiments, an anti-Siglec-7 antibody of the present invention internalizes Siglec-7 and competes with an antibody designated as 16H11 in FIGS. 1-3 for binding to Siglec-7. In some embodiments, an anti-Siglec-7 antibody of the present invention internalizes Siglec-7 and competes with an antibody designated as 16H11 in FIGS. 1-3 for binding to Siglec-7 ligand. In some embodiments, an antibody of the invention has at least one, at least two, or three CDRs of a $V_H$ sequence as set forth in any one of SEQ ID NOS:29-31, 33, and 35-61. In some embodiments, an antibody of the invention has at least one, at least two, or three CDRs of a $V_L$ sequence as set forth in any one of SEQ ID NOS:62 and 64-78. In some embodiments, an anti-Siglec-7 antibody comprises an HCDR3 selected from the HCDR3 sequences as set forth in any one of SEQ ID NOS:29-31, 33, and 35-61 and an LCDR3 selected from the LCDR3 sequences as set forth in any one of SEQ ID NOS:62 and 64-78. In embodiments has six CDRs as set forth in any one of the $V_H$-$V_L$ region pairs set forth in Table 1.

In some embodiments, an anti-Siglec-7 antibody of the present invention comprises a heavy chain variable region having at least 80%, 85%, 90%, 91%, 92%, 93%, 94%, 95%, 96%, 97%, 98%, 99%, or 100% sequence identity to the amino acid sequence of a heavy chain variable region of any one of SEQ ID NOS:29-31, 33, and 35-61. In certain embodiments, a $V_H$ sequence having at least 80%, 85%, 90%, 91%, 92%, 93%, 94%, 95%, 96%, 97%, 98%, or 99% identity to the amino acid sequence of a heavy chain variable region of any one of SEQ ID NOS:29-31, 33, and 35-61 contains substitutions (e.g., conservative substitutions), insertions, or deletions relative to the reference sequence, but an anti-Siglec-7 antibody comprising that sequence retains the ability to bind to Siglec-7. In certain embodiments, a total of 1 to 20 amino acids have been substituted, inserted and/or deleted in the amino acid sequence of a heavy chain variable region of any one of SEQ ID NOS: 29-31, 33, and 35-61. In certain embodiments, all of the substitutions, insertions, or deletions occur in the framework regions. In certain embodiments, 1, 2, or 3 substitutions occur in a CDR region.

In some embodiments, an anti-Siglec-7 antibody of the present invention comprises a light chain variable region having at least 80%, 85%, 90%, 91%, 92%, 93%, 94%, 95%, 96%, 97%, 98%, 99%, or 100% sequence identity to the amino acid sequence of a light chain variable region of any one of SEQ ID NOS:62 and 64-78. In certain embodiments, a $V_L$ sequence having at least 80%, 85%, 90%, 91%, 92%, 93%, 94%, 95%, 96%, 97%, 98%, or 99% identity to the amino acid sequence of a light chain variable region of any one of SEQ ID NOS:62 and 64-78 contains substitutions (e.g., conservative substitutions), insertions, or deletions relative to the reference sequence, but an anti-Siglec-7 antibody comprising that sequence retains the ability to bind to Siglec-7. In certain embodiments, a total of 1 to 20 amino acids have been substituted, inserted and/or deleted in the amino acid sequence of a light chain variable region of any one of SEQ ID NOS:62 and 64-78. In certain embodiments, all of the substitutions, insertions, or deletions occur in the framework regions. In certain embodiments, 1, 2, or 3 substitutions occur in a CDR region.

In some embodiments, an anti-Siglec-7 antibody of the present invention comprises a heavy chain variable region having at least 80%, 85%, 90%, 91%, 92%, 93%, 94%, 95%, 96%, 97%, 98%, 99%, or 100% sequence identity to the amino acid sequence of a heavy chain variable region of any of SEQ ID NOS:41, 42, 43, 44, 45, 46, 47, 48, 49, 50, 51, 52, 53, 54, 55, 57, 58, 59, 60 or 61; and a light chain variable region having at least 80%, 85%, 90%, 91%, 92%, 93%, 94%, 95%, 96%, 97%, 98%, 99%, or 100% sequence identity to the amino acid sequence of a light chain variable region of SEQ ID NO:69, 70, 71, 72, 73, 74, 75, 76, 77, or 78. In some embodiments, the anti-Siglec-7 antibody has a modification to the heavy chain variable region and/or the light chain variable region as described in the preceding two paragraphs.

In some embodiments, an anti-Siglec-7 antibody comprises a heavy chain variable region that comprises a CDR3 as set forth in any one of SEQ ID NOS:29-31, 33, and 35-61 in which 1, 2, or 3 amino acids are substituted, e.g., conservatively substituted; or 1 or 2 amino acids are substituted, e.g., conservatively substituted. In some embodiments, a heavy chain variable region comprises a CDR3 as set forth in any one of SEQ ID NOS:29-31, 33, and 35-61 in which one amino acid is substituted, e.g., conservatively substituted. In some embodiments, a heavy chain variable region comprises three CDRs of a variable region sequence as set forth in any one of SEQ ID NOS:29-31, 33, and 35-61 in which the CDR1 has 1, 2, or 3 amino acid substitutions, e.g., conservative substitutions and/or the CDR2 has 1, 2, or 3 amino acid substitutions, e.g., conservative substitutions. In some embodiments, a heavy chain variable region comprises three CDRs of a variable region sequence as set forth in any one of SEQ ID NOS:29-31, 33, and 35-61 in which the CDR1 has 1 or 2 amino acid substitutions, e.g., conservative substitutions; and/or the CDR2 has 1 or 2 amino acid substitutions, e.g., conservative substitutions. In some embodiments, the heavy chain variable region comprises three CDRs of a variable region sequence as set forth in any one of SEQ ID NOS:29-31, 33, and 35-61 in which the CDR1 and/or the CDR2 has 1 amino acid substitution e.g., a conservative substitution.

In some embodiments, an anti-Siglec-7 antibody of the present invention comprises a heavy chain CDR1 sequence G(G/Y)(K/T)FS(W/S/Y)(F/Y) (SEQ ID NO: 109), a heavy chain CDR2 sequence YP(G/I)(D/F)GE (SEQ ID NO: 110), and a heavy chain CDR3 sequence DYLRAMD(Y/I/V) (SEQ ID NO: 111). In some embodiments, an anti-Siglec-7 antibody of the present invention comprises a heavy chain variable region comprising: a heavy chain CDR3 (HCDR3) sequence DDYLRAMDY (SEQ ID NO:81), DDYLRAMDV (SEQ ID NO:91), or DDYLRAMDI (SEQ ID NO:92); a heavy chain CDR1 (HCDR1) sequence GYDFSNF (SEQ ID NO:79), GYTFSNF (SEQ ID NO:82), GGDFSNF (SEQ ID NO:83), GYDFSSY (SEQ ID NO:87), GYDFSSF (SEQ ID NO:88), or GYDFSNY (SEQ ID NO:89); and a heavy chain CDR2 (HCDR2) sequence YPGDGE (SEQ ID NO:80), YPIDGE (SEQ ID NO:85), or YPGFGE (SEQ ID NO:90). Illustrative CDR2 sequences having mutations that abolish binding are IPGDGE (SEQ ID NO:84) and YPGDGT (SEQ ID NO:86).

In some embodiments, an anti-Siglec-7 antibody comprises a light chain variable region that comprises a CDR3 as set forth in any one of SEQ ID NOS:62 and 64-78 in which 1, 2, or 3 amino acids are substituted, e.g., conservatively substituted; or 1 or 2 amino acids are substituted, e.g., conservatively substituted. In some embodiments, a light chain variable region comprises a CDR3 as set forth in any one of SEQ ID NOS:62 and 64-78 in which one amino acid is substituted, e.g., conservatively substituted. In some embodiments, a light chain variable region comprises three CDRs of a variable region sequence as set forth in any one of SEQ ID NOS:62 and 64-78 in which the CDR1 has 1, 2, 3, or 4 amino acid substitutions, or 1, 2, or 3 amino acid substitutions, e.g., conservative substitutions; and/or the CDR2 has 1, 2, 3, or 4 amino acid substitutions, or 1, 2, or 3 amino acid substitutions, e.g., conservative substitutions. In some embodiments, a light chain variable region comprises three CDRs of a variable region sequence as set forth in any one of SEQ ID NOS:62 and 64-78 in which the CDR1 and/or the CDR2 has 1 or 2 amino acid substitutions, e.g., conservative substitutions. In some embodiments, a light chain variable region comprises three CDRs of a variable region sequence as set forth in any one SEQ ID NOS:62 and 64-78 in which the CDR1 and/or the CDR2 has 1 amino acid substitution e.g., a conservative substitution.

In some embodiments, an anti-Siglec-7 antibody of the present invention comprises a light chain CDR1 sequence RAS(G/Q)(N/G)I(H/S)NYLA (SEQ ID NO: 112), a light chain CDR2 sequence (S/A)A(K/S)RL(E/A)(S/D) (SEQ ID NO: 113) and a light chain CDR3 sequence QHFWSSPYT (SEQ ID NO:95). In some embodiments, an anti-Siglec-7 antibody of the present invention comprises a light chain variable region comprising: a light chain CDR3 (LCDR3) sequence QHFWSSPYT (SEQ ID NO:95); a light chain CDR1 (LCDR1) sequence RASGNIHNYLA (SEQ ID NO:93), RASGGIHNYLA (SEQ ID NO:99), RASQNIHNYLA (SEQ ID NO:100), or RASGNISNYLA (SEQ ID NO:101); and a light chain CDR2 (LCDR2) sequence SAKRLES (SEQ ID NO:94), AASRLES (SEQ ID NO:97), SASRLES (SEQ ID NO:98), SAKRLAS (SEQ ID NO:102), or SAKRLED (SEQ ID NO: 103). An illustrative CDR1 mutation that abolishes binding is RASGNIHNSLA (SEQ ID NO:96).

In some embodiments, an anti-Siglec-7 antibody of the present invention comprises a heavy chain variable region, wherein the heavy chain variable region comprises: a heavy chain CDR3 (HCDR3) sequence DDYLRAMDY (SEQ ID NO:81), DDYLRAMDV (SEQ ID NO:91), or DDYLRAMDI (SEQ ID NO:92); a heavy chain CDR1 (HCDR1) sequence GYDFSNF (SEQ ID NO:79), GYTFSNF (SEQ ID NO:82), GGDFSNF (SEQ ID NO:83), GYDFSSY (SEQ ID NO:87), GYDFSSF (SEQ ID NO:88), or GYDFSNY (SEQ ID NO:89); and a heavy chain CDR2 (HCDR2) sequence YPGDGE (SEQ ID NO:80), YPIDGE (SEQ ID NO:85), or YPGFGE (SEQ ID NO:90); and a light chain variable region, wherein the light chain variable region comprises: a light chain CDR3 (LCDR3) sequence QHFWSSPYT (SEQ ID NO:95); a light chain CDR1 (LCDR1) sequence RASGNIHNYLA (SEQ ID NO:93), RASGGIHNYLA (SEQ ID NO:99), RASQNIHNYLA (SEQ ID NO:100), or RASGNISNYLA (SEQ ID NO:101); and a light chain CDR2 (LCDR2) sequence SAKRLES (SEQ ID NO:94), AASRLES (SEQ ID NO:97), SASRLES (SEQ ID NO:98), SAKRLAS (SEQ ID NO:102), or SAKRLED (SEQ ID NO:103).

In some embodiments, an anti-Siglec-7 antibody of the present invention comprises a heavy chain variable region comprises CDR1, CDR2, and CDR3 sequences as set forth in a heavy chain variable region sequence selected from SEQ ID NO:43, 45, 46, 47, 48, 49, 50, 51, 54, 55, 57, and 58; and a light chain variable region comprising the CDR1, CDR2, and CDR3 sequences of SEQ ID NO:69. In some embodiments, the heavy chain variable region comprises CDR1, CDR2, and CDR3 sequences as set forth in a heavy chain variable region sequence selected from SEQ ID NO:53, 54, 51, 55, 58, and 59; and a light chain variable region comprising the CDR1, CDR2, and CDR3 sequences of SEQ ID NO:78.

In some embodiments, an anti-Siglec-7 of the present invention comprises:
(a) a heavy chain variable region comprising the CDR1, CDR2, and CDR3 sequences as set forth in SEQ ID NO:43, and a light chain variable region comprising the CDR1, CDR2, and CDR3 sequences as set forth in SEQ ID NO:69;
(b) a heavy chain variable region comprising the CDR1, CDR2, and CDR3 sequences as set forth in SEQ ID NO:45, and a light chain variable region comprising the CDR1, CDR2, and CDR3 sequences as set forth in SEQ ID NO:69;
(c) a heavy chain variable region comprising the CDR1, CDR2, and CDR3 sequences as set forth in SEQ ID NO:46, and a light chain variable region comprising the CDR1, CDR2, and CDR3 sequences as set forth in SEQ ID NO:69;
(d) a heavy chain variable region comprising the CDR1, CDR2, and CDR3 sequences as set forth in SEQ ID NO:47, and a light chain variable region comprising the CDR1, CDR2, and CDR3 sequences as set forth in SEQ ID NO:69;
(e) a heavy chain variable region comprising the CDR1, CDR2, and CDR3 sequences as set forth in SEQ ID NO:48, and a light chain variable region comprising the CDR1, CDR2, and CDR3 sequences as set forth in SEQ ID NO:69;
(f) a heavy chain variable region comprising the CDR1, CDR2, and CDR3 sequences as set forth in SEQ ID NO:49, and a light chain variable region comprising the CDR1, CDR2, and CDR3 sequences as set forth in SEQ ID NO:69;
(g) a heavy chain variable region comprising the CDR1, CDR2, and CDR3 sequences as set forth in SEQ ID NO:50, and a light chain variable region comprising the CDR1, CDR2, and CDR3 sequences as set forth in SEQ ID NO:69;
(h) a heavy chain variable region comprising the CDR1, CDR2, and CDR3 sequences as set forth in SEQ ID NO:51, and a light chain variable region comprising the CDR1, CDR2, and CDR3 sequences as set forth in SEQ ID NO:69;
(i) CDR1, CDR2, and CDR3 sequences as set forth in a heavy chain variable region sequence SEQ ID NO:54, and a light chain variable region comprising the CDR1, CDR2, and CDR3 sequences as set forth in SEQ ID NO:69;
(j) a heavy chain variable region comprising the CDR1, CDR2, and CDR3 sequences as set forth in SEQ ID NO:55, and a light chain variable region comprising the CDR1, CDR2, and CDR3 sequences as set forth in SEQ ID NO:69;
(k) a heavy chain variable region comprising the CDR1, CDR2, and CDR3 sequences as set forth in SEQ ID NO:57, and a light chain variable region comprising the CDR1, CDR2, and CDR3 sequences as set forth in SEQ ID NO:69; or
(l) a heavy chain variable region comprising the CDR1, CDR2, and CDR3 sequences as set forth in SEQ ID NO:58, and a light chain variable region comprising the CDR1, CDR2, and CDR3 sequences as set forth in SEQ ID NO:69.

In some embodiments, an anti-Siglec-7 of the present invention comprises:
(a) a heavy chain variable region comprising the CDR1, CDR2, and CDR3 sequences as set forth in SEQ ID NO:53; and a light chain variable region comprising the CDR1, CDR2, and CDR3 sequences as set forth in SEQ ID NO:78;
(b) heavy chain variable region comprising the CDR1, CDR2, and CDR3 sequences as set forth in SEQ ID NO:54; and a light chain variable region comprising the CDR1, CDR2, and CDR3 sequences as set forth in SEQ ID NO:78;
(c) heavy chain variable region comprising the CDR1, CDR2, and CDR3 sequences as set forth in SEQ ID NO:51; and a light chain variable region comprising the CDR1, CDR2, and CDR3 sequences as set forth in SEQ ID NO:78;
(d) heavy chain variable region comprising the CDR1, CDR2, and CDR3 sequences as set forth in SEQ ID NO:55; and a light chain variable region comprising the CDR1, CDR2, and CDR3 sequences as set forth in SEQ ID NO:78;
(e) heavy chain variable region comprising the CDR1, CDR2, and CDR3 sequences as set forth in SEQ ID NO:58; and a light chain variable region comprising the CDR1, CDR2, and CDR3 sequences as set forth in SEQ ID NO:78; or
(f) heavy chain variable region comprising the CDR1, CDR2, and CDR3 sequences as set forth in SEQ ID NO:59; and a light chain variable region comprising the CDR1, CDR2, and CDR3 sequences as set forth in SEQ ID NO:78.

In some embodiments, an anti-Siglec-7 antibody of the present invention internalizes Siglec-7 and competes with an antibody designated as 8A2 in FIGS. 1-3 for binding to Siglec-7. In some embodiments, an anti-Siglec-7 antibody of the invention has at least one, at least two, or three CDRs of a $V_H$ sequence as set forth in any one of SEQ ID NO: 104 or 106. In some embodiments, an anti-Siglec-7 antibody of the invention has at least one, at least two, or three CDRs of a $V_L$ sequence as set forth in SEQ ID NO: 105 or 107. In some embodiments, an anti-Siglec-7 antibody comprises an HCDR3 sequence as set forth in SEQ ID NO: 104 or 106 and an LCDR3 sequence as set forth in SEQ ID NO: 105 or 107.

In some embodiments, an anti-Siglec-7 antibody of the present invention comprises a heavy chain variable region having at least 80%, 85%, 90%, 91%, 92%, 93%, 94%, 95%, 96%, 97%, 98%, 99%, or 100% sequence identity to the amino acid sequence of a heavy chain variable region of SEQ ID NO: 104 or 106. In certain embodiments, a $V_H$ sequence having at least 80%, 85%, 90%, 91%, 92%, 93%, 94%, 95%, 96%, 97%, 98%, or 99% identity to the amino acid sequence of a heavy chain variable region of SEQ ID NO: 104 or 106 contains substitutions (e.g., conservative substitutions), insertions, or deletions relative to the reference sequence, but an anti-Siglec-7 antibody comprising that sequence retains the ability to bind to Siglec-7 and has internalization activity. In certain embodiments, a total of 1 to 20 amino acids have been substituted, inserted and/or deleted in the amino acid sequence of a heavy chain variable region of SEQ ID NO: 104 or 106. In certain embodiments, all of the substitutions, insertions, or deletions occur in the framework regions. In certain embodiments, 1, 2, or 3 substitutions occur in a CDR region.

In some embodiments, an anti-Siglec-7 antibody of the present invention comprises a light chain variable region having at least 80%, 85%, 90%, 91%, 92%, 93%, 94%, 95%, 96%, 97%, 98%, 99%, or 100% sequence identity to the amino acid sequence of a light chain variable region of SEQ ID NO: 105 or 107. In certain embodiments, a $V_L$ sequence having at least 80%, 85%, 90%, 91%, 92%, 93%, 94%, 95%, 96%, 97%, 98%, or 99% identity to the amino acid sequence of a light chain variable region of SEQ ID NO: 105 or 107 contains substitutions (e.g., conservative substitutions), insertions, or deletions relative to the reference sequence, but an anti-Siglec-7 antibody comprising that sequence retains the ability to bind to Siglec-7. In certain embodiments, a total of 1 to 20 amino acids have been substituted, inserted and/or deleted in the amino acid sequence of a light chain variable region of SEQ ID NO: 105 or 107. In certain embodiments, all of the substitutions, insertions, or deletions occur in the framework regions. In certain embodiments, 1, 2, or 3 substitutions occur in a CDR region.

In some embodiments, an anti-Siglec-7 antibody of the present invention comprises a heavy chain variable region having at least 80%, 85%, 90%, 91%, 92%, 93%, 94%, 95%, 96%, 97%, 98%, 99%, or 100% sequence identity to the amino acid sequence of a heavy chain variable region of SEQ ID NO: 104 or 106; and a light chain variable region having at least 80%, 85%, 90%, 91%, 92%, 93%, 94%, 95%, 96%, 97%, 98%, 99%, or 100% sequence identity to the amino acid sequence of a light chain variable region of SEQ ID NO: 105 or 107. In some embodiments, the anti-Siglec-7 antibody has a modification to the heavy chain variable region and/or the light chain variable region as described in the preceding two paragraphs.

In some embodiments, an anti-Siglec-7 antibody comprises a heavy chain variable region that comprises a CDR3 as set forth SEQ ID NO:104 or 106 in which 1, 2, or 3 amino acids are substituted, e.g., conservatively substituted; or 1 or 2 amino acids are substituted, e.g., conservatively substituted. In some embodiments, a heavy chain variable region comprises a CDR3 as set forth in SEQ ID NO:104 or 106 in which one amino acid is substituted, e.g., conservatively substituted. In some embodiments, a heavy chain variable region comprises three CDRs of a variable region sequence as set forth in SEQ ID NO: 104 or 106 in which the CDR1 has 1, 2, or 3 amino acid substitutions, e.g., conservative substitutions and/or the CDR2 has 1 or 2, or 1 only, amino acid substitution, e.g., conservative substitutions.

In some embodiments, an anti-Siglec-7 antibody comprises a light chain variable region that comprises a CDR3 as set forth SEQ ID NO:105 or 107 in which 1, 2, or 3 amino acids are substituted, e.g., conservatively substituted; or 1 or 2 amino acids are substituted, e.g., conservatively substituted. In some embodiments, a light chain variable region comprises a CDR3 as set forth in SEQ ID NO:105 or 107 in which one amino acid is substituted, e.g., conservatively substituted. In some embodiments, a light chain variable region comprises three CDRs of a variable region sequence as set forth in SEQ ID NO: 105 or 107 in which the CDR1 has 1, 2, or 3 amino acid substitutions, e.g., conservative substitutions and/or the CDR2 has 1 or 2, or 1 only, amino acid substitution, e.g., conservative substitutions.

In a further aspect of the invention, an anti-Siglec-7 antibody according to any of the above embodiments is a monoclonal antibody, including a chimeric, humanized or human antibody. In one embodiment, an anti-Siglec-7 antibody is an antibody fragment, e.g., a Fv, Fab, Fab', scFv, diabody, or F(ab')$_2$ fragment. In another embodiment, the antibody is a substantially full length antibody, e.g., an IgG antibody or other antibody class or isotype as defined herein. For a review of certain antibody fragments, see Hudson et al. Nat. Med. 9: 129-134 (2003). Antibody fragments can be made by various techniques, including but not limited to proteolytic digestion of an intact antibody as well as production by recombinant host cells (e.g. *E. coli* or phage), as described herein.

In some embodiments an anti-Siglec-7 antibody in accordance with the present disclosure is a ligand blocking antibody in a monovalent format. In some embodiments, the nati-Siglec-7 antibody is in a fragment format, e.g., a Fv, Fab, Fab', scFv, diabody, or F(ab')$_2$ fragment. In some embodiments, an antibody in a monovalent or fragment format is modified, for example by PEGylation, to extend half-life.

In some embodiments, an anti-Siglec-7 antibody of the present invention is employed in a bispecific or multi-specific format. For example, in some embodiments, the antibody may be incorporated into a bispecific or multi-specific antibody that comprises a therapeutic antibody, as further discussed below.

Fc Engineering

In some embodiments, an antibody of the present disclosure comprises an Fc region. The Fc region may be an Fc region engineered to alter one or more functional properties of the antibody, such as serum half-life, complement fixation, Fc receptor binding, and/or antigen-dependent cellular cytotoxicity. Furthermore, an antibody of the disclosure may be chemically modified (e.g., one or more chemical moieties can be attached to the antibody) or be modified to alter its glycosylation, again to alter one or more functional properties of the antibody In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In one embodiment, an antibody of invention may have a human IgG4 Fc region modified to include a S228P substitution, where the amino acid residues are numbered according to the EU index as in Kabat.

In other embodiments, the Fc region is altered by replacing at least one amino acid residue with a different amino acid residue to alter the effector functions of the antibody. For example, one or more amino acids can be replaced with a different amino acid residue such that the antibody has an altered binding for an effector ligand but retains the antigen-binding ability of the parent antibody. The effector ligand to which binding is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1 q binding and/or reduced or abolished complement dependent cytotoxicity (CDC). This approach is described in further detail in U.S. Pat. No. 6,194,551.

In another embodiment, one or more amino acid residues are altered to thereby alter the ability of the antibody to fix complement. This approach is described further in PCT Publication W01994/29351 by Bodmer et al.

In yet another embodiment, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO2000/42072 by Presta. Moreover, the binding sites on human IgG1 for FcγRI, FcγRII, FcγRIII and FcR have been mapped and variants with improved binding have been described (see Shields et al., (2001) J. Biol. Chem. 276:6591-6604).

In still another embodiment, the glycosylation of an antibody is modified. For example, an aglycoslated antibody or antibody having an altered glycosylation pattern can be made. Glycosylation can be altered, for example, to increase the affinity of the antibody for an antigen or, if made in the Fc region, to influence effector function. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody preparation having reduced amounts of fucosyl residues or an antibody having increased bisecting GlcNac structures. Such altered glycosylation patterns have been demonstrated to increase the ADCC ability of antibodies.

Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, EP 1,176,195 by Hang et al. describes a cell line with a functionally disrupted FUT8 gene, which encodes a fucosyl-transferase, such that antibodies expressed in such a cell line exhibit hypofucosylation. PCT Publication WO2003/035835 by Presta describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277:26733-26740). PCT Publication W01999/54342 by Umana et al. describes cell lines engineered to express glycoprotein-modifying glycosyl-transferases (e.g., beta (1,4)-N acetylglucosaminyl-transferase III (GnTIII)) such that antibodies expressed in the engineered cell lines exhibit increased bisecting GlcNac structures which results in increased ADCC activity of the antibodies (see also Umana et al., (1999) Nat. Biotech. 17:176-180).

In another embodiment, the antibody is modified to increase its biological half-life. Various approaches are possible. For example, one or more of the following mutations can be introduced: T252L, T254S, and T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 region of an Fc region of an IgG, as described in U.S. Pat. Nos. 5,869,046 and 6,121,022 by Presta et al.

Treatment of Cancer

Anti-Siglec-7 antibodies of the invention can be used to treat any number of cancers. In some aspects of the present disclosure antibodies are used to treat cancers that exhibit infiltration of immune cells, such as CD8+ T cells, with high levels of Siglec-7 expression. In some embodiments, anti-Siglec-7 antibodies of the invention can be used to treat cancers that exhibit infiltration of NK cells or monocytes that express Siglec-7.

In some aspects, the disclosure thus provides methods of identifying subjects who are candidates for treatment with an anti-Siglec-7 antibody. Thus, in one embodiment, the invention provides a method of identifying the level of infiltration of Siglec-7 expressing CD8+ T cells in a tumor sample obtained from a patient. In some embodiments, the tumor sample is from a primary tumor. In alternative embodiments, the tumor sample is a metastatic lesion. The level of expression of Siglec-7 on the surface of cells, e.g., T cells, can be measured using any assay, such as immunohistochemistry or flow cytometry. In the context of the determination of levels of expression of Siglec-7 on tumor-infiltrating T cells, "overexpression" of Siglec-7 is considered to be where at least 10%, at least 20%, or at least 25%, or at least 30%, or greater, of the cells being analyzed, e.g., CD8+ T cells, express detectable Siglec-7 on the cell surface. Thus, "overexpress" in this context refers to the percentage of T cells that express detectable Siglec-7. "Overexpression" in this context is synonymous with the term "elevated numbers" or "elevated levels" of T cells that express detectable Siglec-7 in referring to the percentage of T cells that express detectable Siglec-7.

The level of Siglec-7 ligand expressed by a tumor is also typically evaluated. A tumor is considered to express Siglec-7 ligand when detectable binding of Siglec-7 is observed on the surface of tumor cells. In some embodiments, expression of Siglec-7 ligand on at least 10%, at least 20%, at least 30%, at least 50%, or greater of the tumor cells in a sample that is evaluated may be used as a selection criteria for determining a patient to be treated with an anti-Siglec-7 antibody.

Any cancer can be treated with an anti-Siglec-7 antibody as described herein. In some embodiments, the cancer is a carcinoma or a sarcoma. In some embodiments, the cancer is a hematological cancer. In some embodiments, the cancer is breast cancer, prostate cancer, testicular cancer, renal cell cancer, bladder cancer, ovarian cancer, cervical cancer, endometrial cancer, lung cancer, colorectal cancer, anal cancer, pancreatic cancer, gastric cancer, esophageal cancer, hepatocellular cancer, head and neck cancer, glioblastoma, mesothelioma, melanoma, or a bone or soft tissue sarcoma. In some embodiments, the cancer is acute lymphoblastic leukemia, acute myeloid leukemia, adrenocortical carcinoma, anal cancer, appendix cancer, astrocytoma, basal-cell carcinoma, bile duct cancer, bladder cancer, bone tumor, brainstem glioma, brain cancer, cerebellar astrocytoma, cerebral astrocytoma, ependymoma, medulloblastoma, supratentorial primitive neuroectodermal tumors, visual pathway and hypothalamic glioma, breast cancer, bronchial adenomas, Burkitt's lymphoma, central nervous system lymphoma, cerebellar astrocytoma, cervical cancer, chondrosarcoma, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, epitheliod hemangioendothelioma (EHE), esophageal cancer, Ewing's sarcoma, extracranial germ cell tumor, extragonadal germ cell tumor, extrahepatic bile duct cancer, eye cancer, intraocular melanoma, retinoblastoma, gallbladder cancer, gastric cancer, gastrointestinal carcinoid tumor, gastrointestinal stromal tumor (GIST), germ cell tumor, gestational trophoblastic tumor, gastric carcinoid, hairy cell leukemia, head and neck cancer, heart cancer, hepatocellular cancer, Hodgkin lymphoma, hypopharyngeal cancer, hypothalamic and visual pathway glioma, childhood, intraocular melanoma, islet cell carcinoma, Kaposi sarcoma, kidney cancer, laryngeal cancer, leukaemias, lip and oral cavity cancer, liposarcoma, liver cancer, non-small cell lung cancer, small-cell lung cancer, lymphomas, macroglobulinemia, male breast cancer, malignant fibrous histiocytoma of bone, medulloblastoma, melanoma, Merkel cell cancer, mesothelioma, metastatic squamous neck cancer, mouth cancer, multiple endocrine neoplasia syndrome, multiple myeloma, mycosis fungoides, myelodysplastic syndromes, myelogenous leukemia, myeloid leukemia, adult acute, myeloproliferative disorders, chronic, myxoma, nasal cavity and paranasal sinus cancer, nasopharyngeal carcinoma, neuroblastoma, non-Hodgkin lymphoma, oligodendroglioma, oral cancer, oropharyngeal cancer, osteosarcoma, ovarian cancer, ovarian epithelial cancer, ovarian germ cell tumor, ovarian low malignant potential tumor, pancreatic cancer, paranasal sinus and nasal cavity cancer, parathyroid cancer, penile cancer, pharyngeal cancer, pheochromocytoma, pineal astrocytoma, pineal germinoma, pineoblastoma, supratentorial primitive neuroectodermal tumors, pituitary adenoma. plasma cell neoplasia, pleuropulmonary blastoma, primary central nervous system lymphoma, prostate cancer, rectal cancer, renal cell carcinoma, retinoblastoma, rhabdomyosarcoma, salivary gland cancer, Ewing sarcoma, Kaposi sarcoma, soft tissue sarcoma, uterine sarcoma, Sdzary syndrome, non-melanoma skin cancer, melanoma Merkel cell skin carcinoma, small intestine cancer, squamous cell carcinoma, squamous neck cancer, stomach cancer, cutaneous T-Cell lymphoma, testicular cancer, throat cancer, thymoma, thyroid cancer, transitional cell cancer of the renal pelvis and ureter, trophoblastic tumor, gestational, urethral cancer, uterine cancer, vaginal cancer, vulvar cancer, Waldenstrom macroglobulinemia, or Wilms tumor.

In one aspect, methods of the disclosure comprise administering an anti-Siglec-7 antibody as a pharmaceutical composition to a cancer patient in a therapeutically effective amount using a dosing regimen suitable for treatment of the cancer. The composition can be formulated for use in a variety of drug delivery systems. One or more physiologically acceptable excipients or carriers can also be included in the compositions for proper formulation. Suitable formulations for use in the present invention are found, e.g., in Remington: The Science and Practice of Pharmacy, 21st Edition, Philadelphia, Pa. Lippincott Williams & Wilkins, 2005.

The anti-Siglec-7 antibody is provided in a solution suitable for administration to the patient, such as a sterile isotonic aqueous solution for injection. The antibody is dissolved or suspended at a suitable concentration in an acceptable carrier. In some embodiments the carrier is aqueous, e.g., water, saline, phosphate buffered saline, and the like. The compositions may contain auxillary pharmaceutical substances as required to approximate physiological conditions, such as pH adjusting and buffering agents, tonicity adjusting agents, and the like.

The pharmaceutical compositions are administered to a patient in an amount sufficient to cure or at least partially arrest the disease or symptoms of the disease and its complications. An amount adequate to accomplish this is defined as a "therapeutically effective dose." A therapeutically effective dose is determined by monitoring a patient's response to therapy. Typical benchmarks indicative of a therapeutically effective dose include amelioration of symptoms of the disease in the patient. Amounts effective for this use will depend upon the severity of the disease and the general state of the patient's health, including other factors such as age, weight, gender, administration route, etc. Single or multiple administrations of the antibody may be administered depending on the dosage and frequency as required and tolerated by the patient. In any event, the methods provide a sufficient quantity of anti-Siglec-7 antibody to effectively treat the patient.

An anti-Siglec-7 antibody can be administered by any suitable means, including, for example, parenteral, intrapulmonary, and intranasal, administration, as well as local administration, such as intratumor administration. Parenteral infusions include intramuscular, intravenous, intraarterial, intraperitoneal, or subcutaneous administration. In some embodiments, the antibody may be administered by insufflation. In an illustrative embodiment, the antibody may be stored at 10 mg/ml in sterile isotonic aqueous saline solution for injection at 4° C. and is diluted in either 100 ml or 200 ml 0.9% sodium chloride for injection prior to administration to the patient. In some embodiments, the antibody is administered by intravenous infusion over the course of 1 hour at a dose of between 0.01 and 25 mg/kg. In other embodiments, the antibody is administered by intravenous infusion over a period of between 15 minutes and 2 hours. In still other embodiments, the administration procedure is via sub-cutaneous bolus injection.

The dose of antibody is chosen in order to provide effective therapy for the patient and is in the range of less than 0.01 mg/kg body weight to about 25 mg/kg body weight or in the range 1 mg-2 g per patient. Preferably the dose is in the range 0.1-10 mg/kg or approximately 50 mg-1000 mg/patient. The dose may be repeated at an appropriate frequency which may be in the range once per day to once every three months, or every six months, depending on the pharmacokinetics of the antibody (e.g., half-life of the antibody in the circulation) and the pharmacodynamic response (e.g., the duration of the therapeutic effect of the antibody). In some embodiments, the in vivo half-life of between about 7 and about 25 days and antibody dosing is repeated between once per week and once every 3 months or once every 6 months. In other embodiments, the antibody is administered approximately once per month.

An anti-Siglec-7 antibody of may be administered with one or more additional therapeutic agents, e.g., chemotherapeutic agents and/or additional immunotherapies.

In some embodiments, an anti-Siglec-7 antibody can be administered in conjunction with another checkpoint inhibitor. In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In certain embodiments, the checkpoint inhibitor inhibits a checkpoint protein which may be CTLA-4, PDL1, ICOS, PDL2, IDO1, ID02, PD1, B7-H3, B7-H4, BTLA, HVEM, TIM3, GAL9, GITR, HAVCR2, LAG3, KIR, LAIR1, LIGHT, MARCO, OX-40, SLAM, 2B4, CD2, CD27, CD28, CD30, CD40, CD70, CD80, CD86, CD137, CD160, CD39, VISTA, TIGIT, CGEN-15049, 2B4, CHK 1, CHK2, A2aR, B-7 family ligands or a combination thereof. In some embodiments, the immune checkpoint inhibitor is an inhibitor of PD-L1. In some embodiments, the immune checkpoint inhibitor is an inhibitor of PD-1. In some embodiments, the immune checkpoint inhibitor is an inhibitor of CTLA-4. In some embodiments, the immune checkpoint inhibitor is an inhibitor of LAG3. In some embodiments, the immune checkpoint inhibitor is an inhibitor of TIM3. In some embodiments, the immune checkpoint inhibitor is ICOS.

In some embodiments, an anti-Siglec-7 antibody can be administered in conjunction with a therapeutic antibody, such as an antibody that targets a tumor cell antigen. Examples of therapeutic antibodies include rituximab, trastuzumab, tositumomab, ibritumomab, alemtuzumab, epratuzumab, bevacizumab, elotuzumab, necitumumab, blinatumomab, brentuximab, cetuximab, daratumumab, denosumab, dinutuximab, gemtuzumab ibritumomab ipilimumab, nivolumab, obinutuzumab, ofatumumab, adotrastuzumab, panitumumab, pembrolizumab, pertuzumab, ramucirumab, and ranibizumab.

In some embodiments, an anti-Siglec-7 antibody is administered with a chemotherapeutic agent. Examples of cancer chemotherapeutic agents include alkylating agents such as thiotepa and cyclophosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; antiadrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside; cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; docetaxel, platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylomithine (DMFO); retinoic acid derivatives such as bexarotene, alitretinoin; denileukin diftitox; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, mifepristone, aromatase inhibiting 4(5)-imidazoles, 4-hydroxytamoxifen, trioxifene, keoxifene, LY 1 17018, onapristone, and toremifene (Fareston); and anti-androgens such as flutamide, nilutamide, bicalutamide, leuprolide, and goserelin; and pharmaceutically acceptable salts, acids or derivatives of any of the above. Further cancer therapeutic agents include sorafenib and other protein kinase inhibitors such as afatinib, axitinib, crizotinib, dasatinib, erlotinib, fostamatinib, gefitinib, imatinib, lapatinib, lenvatinib, mubritinib, nilotinib, pazopanib, pegaptanib, ruxolitinib, vandetanib, vemurafenib, and sunitinib; sirolimus (rapamycin), everolimus and other mTOR inhibitors. Examples of additional chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea). Illustrative chemotherapeutic agents additionally include paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinasel and other inhibitors of proteins or enzymes known to be upregulated, over-expressed or activated in cancers, the inhibition of which down regulates cell replication. Additional agents include asparaginase and a Bacillus Calmete-Guerin preparation.

An anti-Siglec-7 antibody may also be administered to a cancer patient in conjunction with a cell based therapy, such as NK cell therapy or a cancer vaccine. In some instances, a cancer vaccine is a peptide-based vaccine, a nucleic acid based vaccine, a cell-based vaccine, a virus-based or viral fragment based vaccine or an antigen presenting cell (APC) based vaccine (e.g. dendritic cell based vaccine). Cancer vaccines include Gardasil®, Cervarix®, sipuleucel-T (Provenge®), NeuVax™, HER-2 ICD peptide-based vaccine, HER-2/neu peptide vaccine, AdHER2/neu dendritic cell vaccine, HER-2 pulsed DC1 vaccine, Ad-sig-hMUC-1/ecdCD40L fusion protein vaccine, MVX-ONCO-1, hTERT/survivin/CMV multipeptide vaccine, E39, J65, PlOs-PA-DRE, rV-CEA-Tricom, GVAX®, Lucanix®, HER2 VRP, AVX901, ONT-10, ISA101, ADXS1 1-001, VGX-3100, INO-9012, GSK1437173A, BPX-501, AGS-003, IDC-G305, HyperAcute®-Renal (HAR) immunotherapy, Prevenarl3, MAGER-3.A1, NA17.A2, DCVax-Direct, latent membrane protein-2 (LMP2)-loaded dendritic cell vaccine (NCT02115126), HS410-101 (NCT02010203, Heat Biologies), EAU RF 2010-01 (NCT01435356, GSK), 140036 (NCT02015104, Rutgers Cancer Institute of New Jersey), 130016 (NCTO 1730118, National Cancer Institute), MVX-201101 (NCT02193503, Maxivax SA), ITL-007-ATCR-MBC (NCT01741038, Immunovative Therapies, Limited), CDR0000644921 (NCT00923143, Abramson cancer center of the University of Pennsylvania), SuMo-Sec-01

(NCT00108875, Julius Maximilians Universitaet Hospital), or MCC-15651 (NCT01176474, Medarex, Inc, BMS).

In the context of the present invention a therapeutic agent that is administered in conjunction with an anti-Siglec-7 antibody of the present invention can be administered prior to administrations of the anti-Siglec-7 antibody or after administration of the anti-Siglec-7 antibody. In some embodiments, an anti-Siglec-7 antibody may be administered at the same time as the additional therapeutic agent.

The following examples are offered for illustrative purposes, and are not intended to limit the invention. Those of skill in the art will readily recognize a variety of non-critical parameters that can be changed or modified to yield essentially the same results.

EXAMPLES

Example 1. Siglec-7 Detection on Tumor-Infiltrating T Cells

Figure 5:
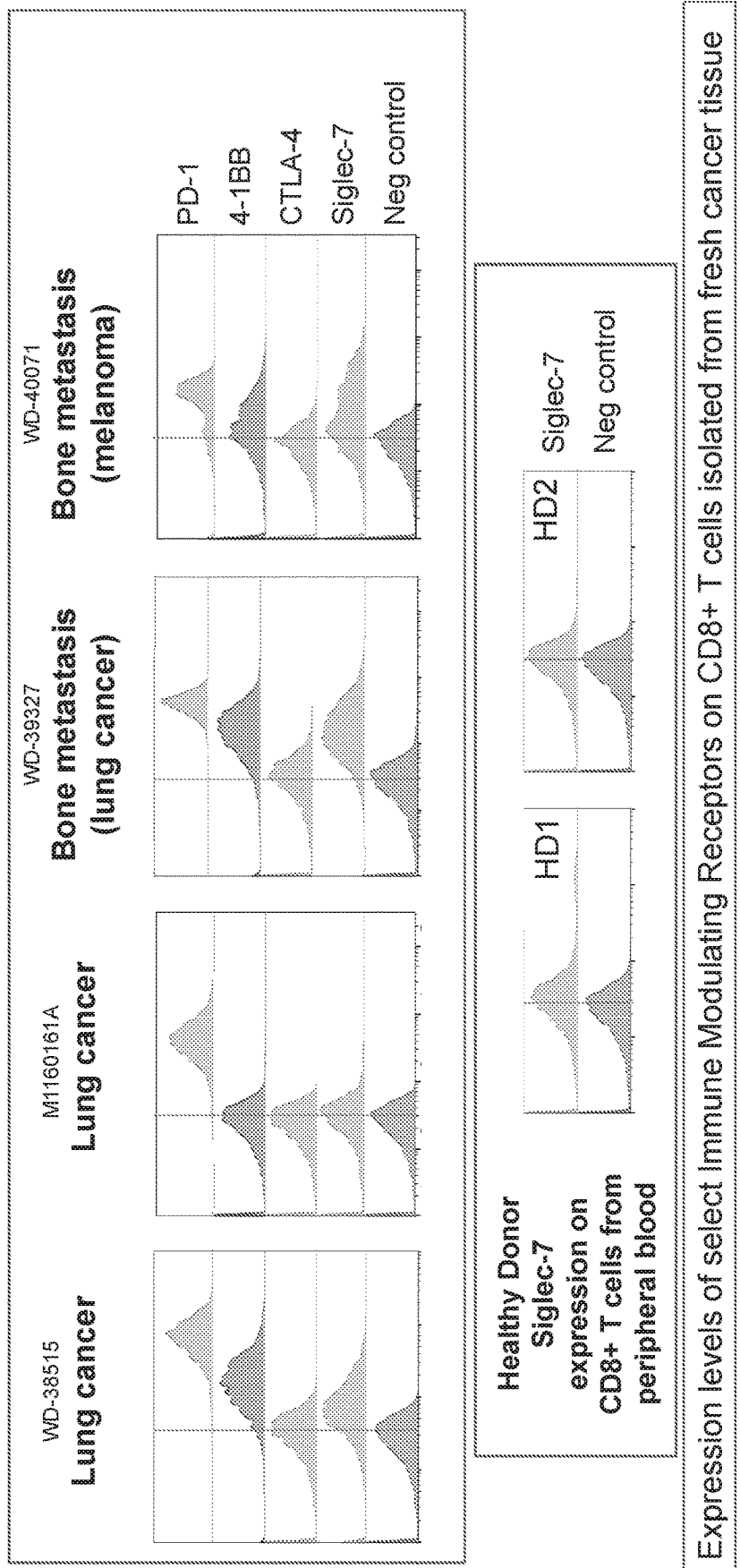
FIG. 5 provides data illustrating that CD8+ T cells isolated from subsets of tumors have a high level of Siglec-7.

Samples comprising cells from primary human tumor specimens were prepared using the Mylteni GentleMACS instrument according to the manufacturer's instructions. Cells were analyzed by fluorescent-activated cell sorting to determine immune cell surface markers including CD3, CD8, CD16, CD45 and 7-AAD as a viability marker. CD8+ T cells were identified and gated as 7-AAD− CD45+ CD3+ CD8+. Anti-Siglec-7-PE (clone S7.7 Biolegend) was used to detect Siglec-7 levels. The results demonstrated that both the percentage (FIG. 4) and the level (FIG. 5) of Siglec-7 expression is enhanced on CD8+ tumor-infiltrating T cells in a subset of tumors.

Example 2. Siglec-7 Ligand Detection on Tumor Cells

Figure 6:
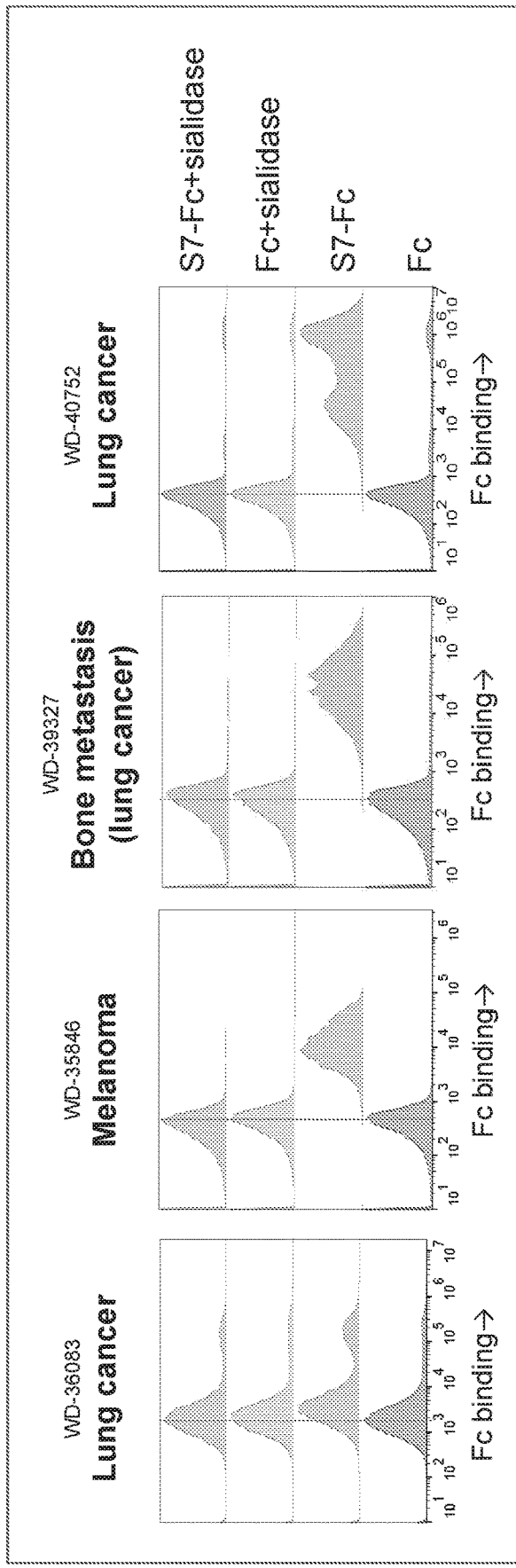
FIG. 6 data illustrating that Siglec-7 ligands are expressed on subsets of tumors.

Ligand levels on tumor cells were also evaluated. Specific binding of recombinant Siglec-7-Fc fusion protein was used to assess Siglec-7 ligand levels on cells isolated form fresh primary tumors. As a specificity control, cells were treated with sialidase/neuraminidase (Roche) at 0.1 U/mL to remove sialic acids from the cell surface. The results demonstrated that Siglec-7 ligands are detected on tumor cells from various subsets of tumors (FIG. 6). Sialidase treatment of cells (i.e. "stripping" of sialoglycans from the cell membrane) eliminated binding.

Example 3. Antibodies with Improved $K_D$

Figure 7:
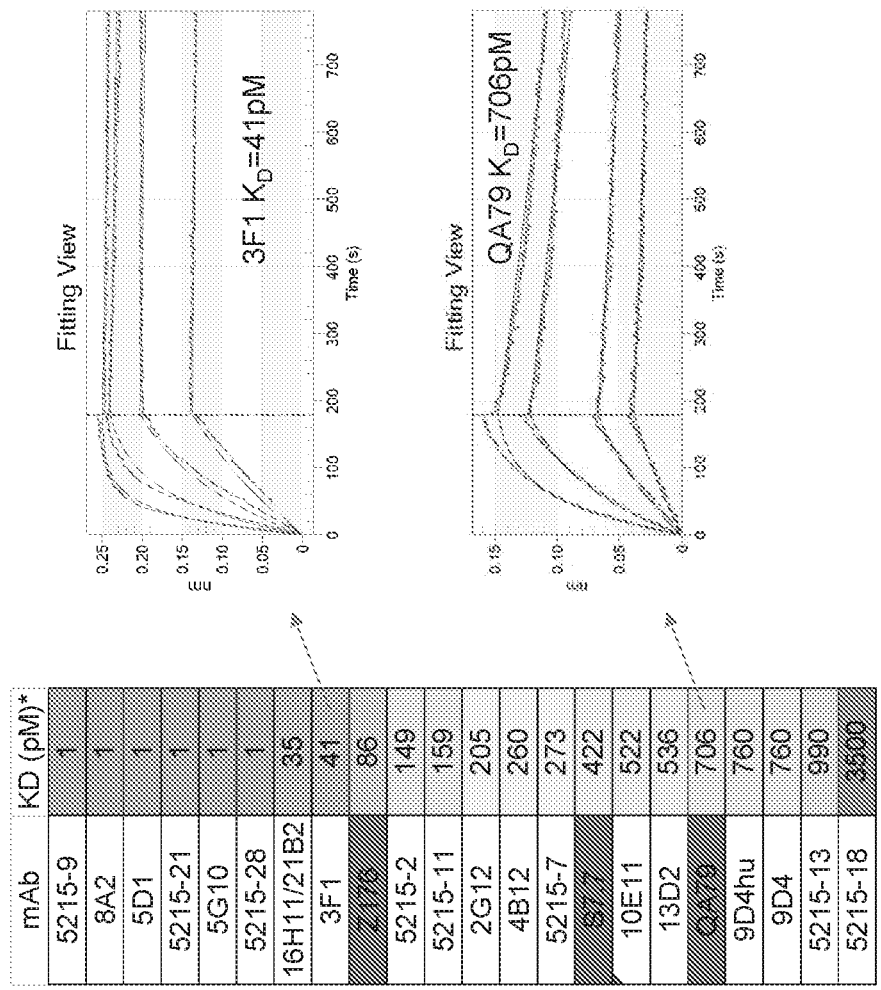
FIG. 7 provides data showing anti-Siglec-7 antibodies of the present disclosure that have improved $K_D$ values compared to antibodies Z176, S7.7, or QA79.

A panel of antibodies was evaluated for binding to Siglec-7. The results identified anti-Siglec-7 antibodies that have improved $K_D$ values compared to commercially available anti-Siglec-7 antibodies (FIG. 7).

Example 4. Antibodies with Siglec-7 Ligand Blocking Activity

Figure 8:
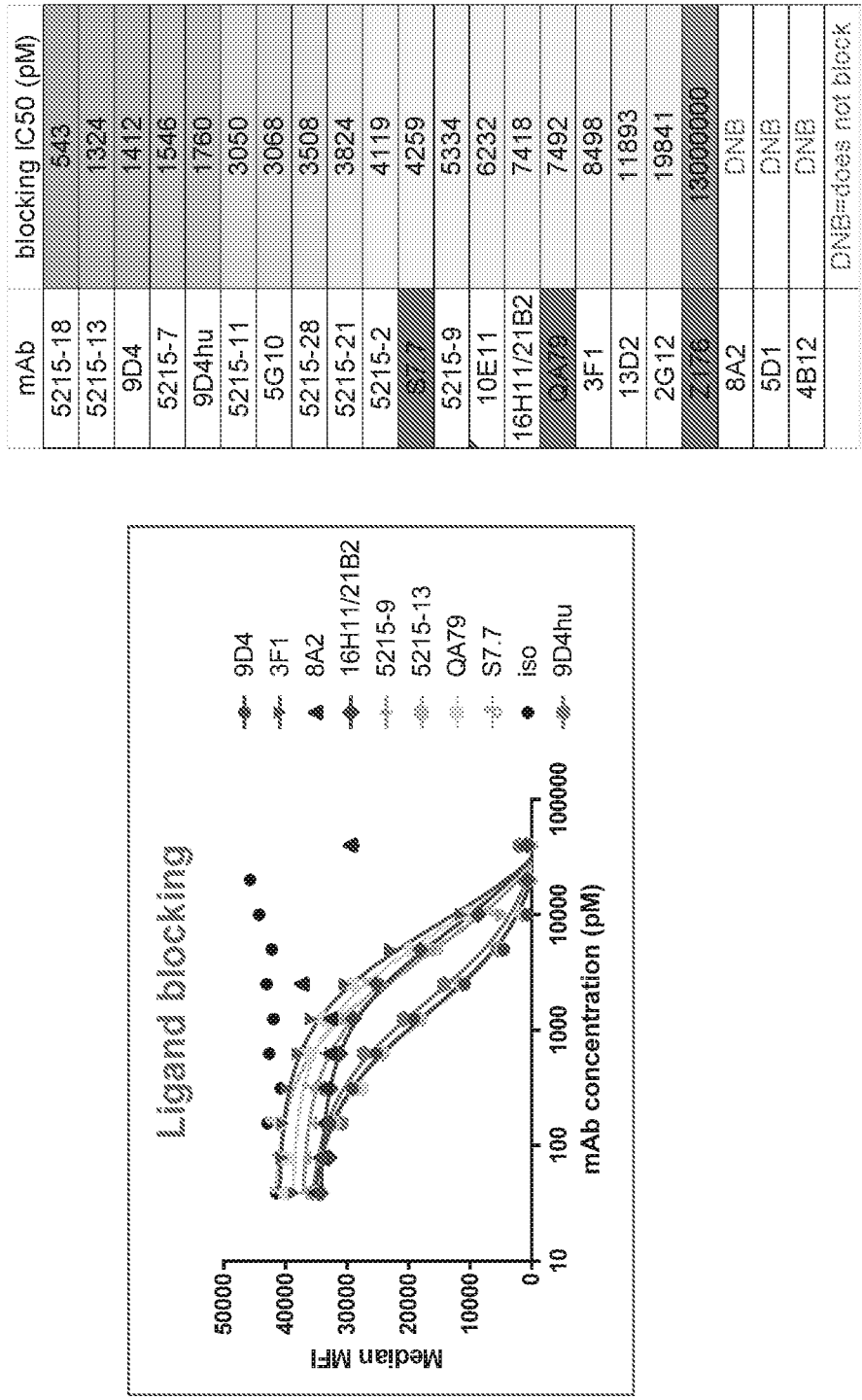
FIG. 8 provides data showing anti-Siglec-7 antibodies of the present disclosure that have improved ligand blocking activity compared to antibodies Z176, S7.7, or QA79.

Recombinant Siglec-7-Fc was added to A375 cells in the presence of anti-Siglec-7 antibodies at increasing concentrations and binding of the complex was detected on the cell surface. The results showed that anti-Siglec-7 antibodies blocked the interaction of Siglec-7 with ligands present on the surface of A375 melanoma human cells with various potencies (FIG. 8) and demonstrated antibodies that have improved ligand blocking activity relative to commercially available anti-Siglec-7 antibodies.

Example 5. Antibodies with Siglec-7 Internalization Activity

Figure 9:
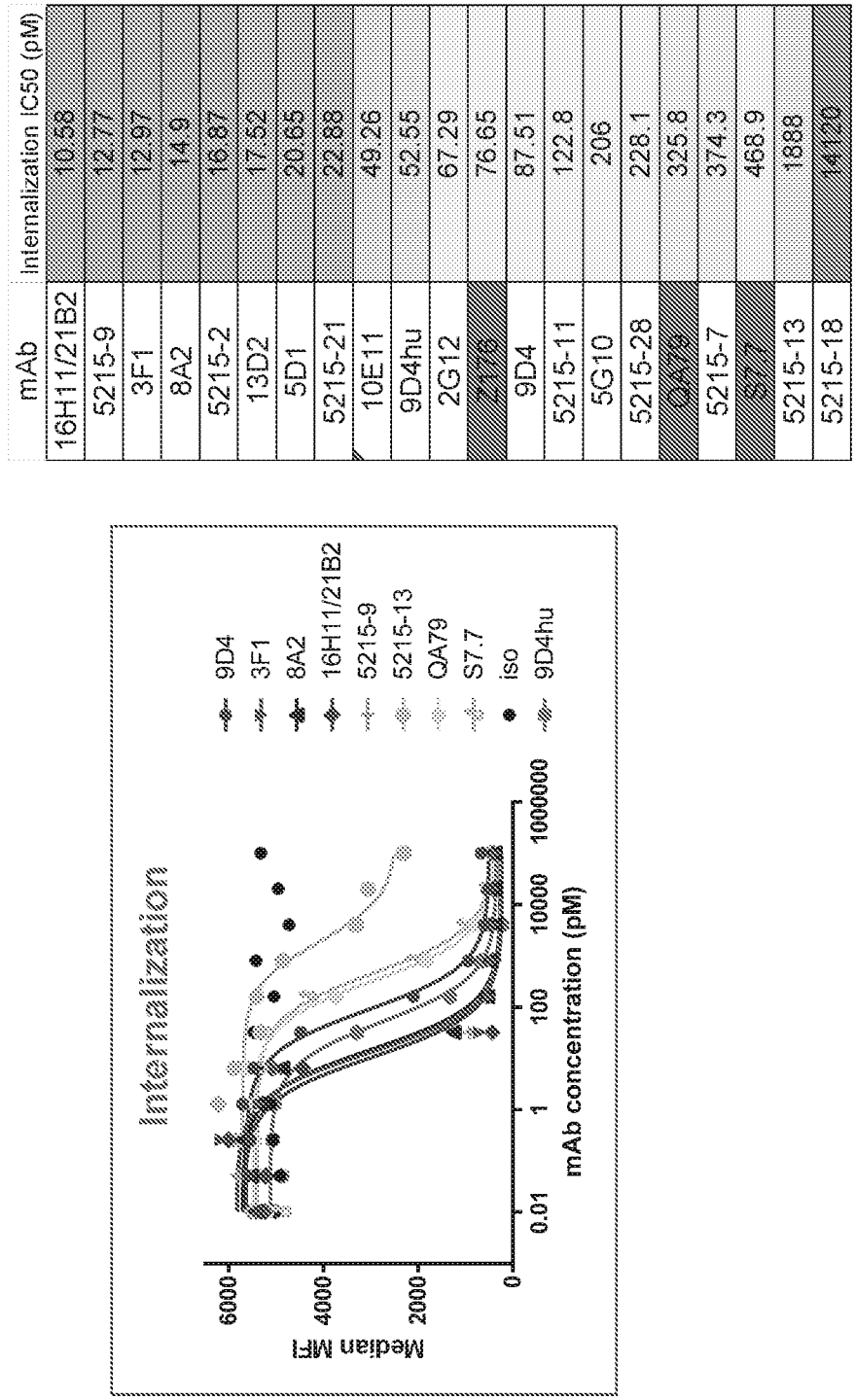
FIG. 9 provides data showing anti-Siglec-7 antibodies of the present disclosure that have improved internalization activity compared to antibodies Z176, S7.7, or QA79.

Primary human peripheral blood mononuclear cells (PBMC) were incubated with increasing concentrations of anti-Siglec-7 antibodies for 24 hours and remaining Siglec-7 in the cell surface of NK cells was detected using a non-competing anti-Siglec-7 antibody. The results showed that anti-Siglec-7 antibodies caused internalization of Siglec-7 on primary human NK cells with various potencies (FIG. 9) and demonstrated antibodies that have improved internalization activity compared to commercially available, or previously described, anti-Siglec-7 antibodies. Rapid, concentration-dependent antibody-induced internalization of Siglec-7 on human NK cells was further evaluated using monoclonal antibody 3F1. 3F1 showed more potent internalization activity compared to commercially available S7.7 antibody (FIG. 10)

Evaluation of monoclonal antibody 8A2 (FIG. 11) demonstrated that the antibody did not block Siglec-7/ligand interaction (left panel), but caused internalization (right panel) of Siglec-7 on primary human immune cells.

Example 6. Humanized Sequences

Humanized antibodies were generated using monoclonal antibodies 16H11 and 8A2 to generate humanized internalizing anti-Siglec 7 antibodies.

Humanized antibodies derived from 16H11 were evaluated for binding to Siglec 7. Antibody binding results (measured in the form of a monovalent Fab) are shown in Table 1. Antibodies having the following heavy and light chain variable regions demonstrated $K_D$ values (monovalent Fab) of about 75 nM or lower: VH438-4 and VL418-2; VH440-2 and VL418-2; VH441-2 and VL418-2; VH443-1 and VL418-2; VH444-2 and VL418-2, VH445-3 and VL418-2; VH449-4 and VL448-3; VH449-6 and VL418-2; VH387-11 and VL418-2; VH446-7 and VL418-2; VH 446-7 and VL448-3; VH463-2 and VL418-2; Vh463-2 and VL448-3; FH465-17 and VL418-2; VH484-6 and VL418-2; VH484-6 and VL448-3; and VH484-7 and VL448-3. The ligand blocking activity of the 16H11 anti-Siglec-7 antibody is preserved, as indicated by analysis of selected antibodies (indicated by the VH/VL pairs in Table 1): AK410-1/AK418-2, AK446-7/AK418-2, and AK446-7/AK448-3.

TABLE 1

$K_D$ values of humanized antibodies derived from 16H11 measured as monovalent Fabs:

| No. | VH | VL | KD (pM) |
|---|---|---|---|
| 1 | AK410-1 (SEQ ID NO: 44) | AK418-2 (SEQ ID NO: 69) | 250-500 |
| 2 | AK417-17 (SEQ ID NO: 42) | AK418-2 (SEQ ID NO: 69) | 250-500 |
| 3 | AK417-8 (SEQ ID NO: 41) | AK421-3 (SEQ ID NO: 71) | >500 |
| 4 | AK417-8 (SEQ ID NO: 41) | AK419-2 (SEQ ID NO: 70) | >500 |
| 5 | AK417-17 (SEQ ID NO: 42) | AK421-3 (SEQ ID NO: 71) | 250-500 |

TABLE 1-continued

K$_D$ values of humanized antibodies derived from
16H11 measured as monovalent Fabs:

| No. | VH | VL | KD (pM) |
|---|---|---|---|
| 6 | AK417-17 (SEQ ID NO: 42) | AK419-2 (SEQ ID NO: 70) | >500 |
| 7 | AK417-17 (SEQ ID NO: 42) | AK424-1 (SEQ ID NO: 72) | >500 |
| 8 | AK417-17 (SEQ ID NO: 42) | AK425-3 (SEQ ID NO: 73) | >500 |
| 9 | AK417-17 (SEQ ID NO: 42) | AK426-2 (SEQ ID NO: 74) | >500 |
| 10 | AK417-17 (SEQ ID NO: 42) | AK427-1 (SEQ ID NO: 75) | >500 |
| 12 | AK417-17 (SEQ ID NO: 42) | AK418-2 (SEQ ID NO: 69) | >500 |
| 13 | AK417-17 (SEQ ID NO: 42) | AK419-2 (SEQ ID NO: 70) | >500 |
| 14 | AK417-17 (SEQ ID NO: 42) | AK435-7 (SEQ ID NO: 76) | >500 |
| 15 | AK417-8 (SEQ ID NO: 41) | AK419-2 (SEQ ID NO: 70) | >500 |
| 16 | AK417-8 (SEQ ID NO: 41) | AK435-7 (SEQ ID NO: 76) | >500 |
| 17 | AK438-4 (SEQ ID NO: 45) | AK418-2 (SEQ ID NO: 69) | <75 |
| 18 | AK440-2 (SEQ ID NO: 46) | AK418-2 (SEQ ID NO: 69) | <100 |
| 19 | AK441-2 SEQ ID NO: 47) | AK418-2 (SEQ ID NO: 69) | <75 |
| 20 | AK417-17 (SEQ ID NO: 42) | AK435-7 (SEQ ID NO: 76) | 250-500 |
| 21 | AK417-17 (SEQ ID NO: 42) | AK439-5 (SEQ ID NO: 77) | 250-500 |
| 22 | AK417-8 (SEQ ID NO: 41) | AK439-5 (SEQ ID NO: 77) | 250 |
| 23 | AK443-1 (SEQ ID NO: 48) | AK418-2 (SEQ ID NO: 69) | <75 |
| 24 | AK444-2 (SEQ ID NO: 49) | AK418-2 (SEQ ID NO: 69) | <75 |
| 25 | AK445-3 (SEQ ID NO: 50) | AK418-2 (SEQ ID NO: 69) | <75 |
| 26 | AK447-2 (SEQ ID NO: 52) | AK418-2 (SEQ ID NO: 69) | 75-150 |
| 27 | AK447-2 (SEQ ID NO: 52) | AK448-3 (SEQ ID NO: 78) | 75-150 |
| 28 | AK449-4 (SEQ ID NO: 53) | AK418-2 (SEQ ID NO: 69) | 75-150 |
| 29 | AK449-4 (SEQ ID NO: 53) | AK448-3 (SEQ ID NO: 78) | <100 |
| 30 | AK449-6 (SEQ ID NO: 54) | AK418-2 (SEQ ID NO: 69) | <100 |
| 31 | AK449-6 (SEQ ID NO: 54) | AK448-3 (SEQ ID NO: 78) | 50-100 |
| 32 | AK387-11 (SEQ ID NO: 43) | AK418-2 (SEQ ID NO: 69) | <75 |
| 33 | AK446-7 (SEQ ID NO: 51) | AK418-2 (SEQ ID NO: 69) | <75 |
| 34 | AK446-7 (SEQ ID NO: 51) | AK448-3 (SEQ ID NO: 78) | <75 |
| 35 | AK463-2 (SEQ ID NO: 55) | AK418-2 (SEQ ID NO: 69) | <75 |
| 36 | AK463-2 (SEQ ID NO: 55) | AK448-3 (SEQ ID NO: 78) | <75 |
| 37 | AK446-7 (SEQ ID NO: 51) | AK419-2 (SEQ ID NO: 70) | >500 |
| 38 | AK463-2 (SEQ ID NO: 55) | AK419-2 (SEQ ID NO: 70) | >500 |
| 39 | AK465-17 (SEQ ID NO: 57) | AK418-2 (SEQ ID NO: 69) | <75 |
| 40 | AK465-17 (SEQ ID NO: 57) | AK419-2 (SEQ ID NO: 70) | 150-250 |
| 41 | AK465-17 (SEQ ID NO: 57) | AK448-3 (SEQ ID NO: 78) | 100-150 |
| 42 | AK484-6 (SEQ ID NO: 58) | AK418-2 (SEQ ID NO: 69) | <100 |
| 43 | AK484-6 (SEQ ID NO: 58) | AK448-3 (SEQ ID NO: 78) | <75 |
| 44 | AK484-7 (SEQ ID NO: 59) | AK448-3 (SEQ ID NO: 78) | <75 |
| 45 | AK485-5 (SEQ ID NO: 61) | AK418-2 (SEQ ID NO: 69) | >500 |
| 46 | AK485-5 (SEQ ID NO: 61) | AK448-3 (SEQ ID NO: 78) | >500 |
| 47 | AK485-4 (SEQ ID NO: 60) | AK448-3 (SEQ ID NO: 78) | >500 |

Methods

K$_D$ Measurements

Antibody binding analysis was carried out by bio-layer interferometry (ForteBio). The assay was conducted at 25° C. in 1× ForteBio Kinetics buffer (ForteBio18-132) in ultrapure water. Antibodies were captured on anti-mouse kinetic sensors at 0.5 ug/mL; Siglec-7-ECD was used as analyte and diluted in assay buffer from 50 nM to 1.56 nM with 2× dilutions. Two-minute associations were conducted, followed by 10-minute dissociations. Results were determined relative to a control empty reference AHC sensor, and analyzed using ForteBio analysis software with 1:1 global fit parameters.

Antibody Competition Using Fortebio

Siglec-7-ECD-huFc was captured on anti-human IgG kinetic sensors at 0.5 ug/ml under saturating conditions (15 min at 1 ug/ml), after which the competing antibody was tested for binding. Each anti-Siglec-7 antibody was tested both ways (i.e. as saturating antibody and as competing antibody) against all other antibodies. When the antibody on the sensor competes with the antibody in solution, no additional binding to the antigen is observed. When a binding signal is observed, the two antibodies bind to the antigen in a non-competitive manner.

Ligand Blocking Assay

Human melanoma cell line A375, which expresses high level of ligands for Siglec-7, was used to determine the blocking activity of anti-Siglec-7 antibodies in a cell based assay. Two-fold serial dilutions of anti-Siglec-7 antibodies (40 nM to 40 pM) were combined with 10 nM Siglec-7-ECD-Fc in FACS buffer (PBS/2% BSA) and incubated on ice for 30 minutes. 2.5×10e4 A375 cells per well were added to round bottom 96-well tissue culture plates in FACS buffer, plates were centrifuged at 400 g for 2 min, supernatant was removed and cells were re-suspended in 100 ul of the antibody-Siglec-7 complexes. After a 1 hour incubation on ice, cells were washed twice and incubated for 30 minutes with goat anti-human F(ab')$_2$ fragment conjugated to AF647 (Jackson IR labs) at 1 ug/ml in FACS buffer. After two more washes, cells were fixed in PBS/2% PFA and acquired on a Novocyte flow cytometer (ACEA biosciences). IC$_{50}$ values for blocking were determined based on plotting mean fluorescence in the APC channel and analysis using Prism Graphpad software.

Internalization Assay

Healthy donor peripheral blood mononuclear monocytes (PBMC) were used to determine internalization activity of anti-Siglec-7 antibodies. Previously cryopreserved PBMC were thawed and incubated for 90 minutes at 37° C. in complete medium (RPMI medium supplemented with 10% fetal bovine serum). Five-fold serial dilutions of anti-Siglec-7 antibodies (100 nM-0.01 pM) were prepared in complete medium. Cells (5×10e4 per well) and antibody dilutions were combined in 96-well tissue culture plates and incubated at 37° C. for 24 hours. Cells were re-suspended in huFc block (Becton Dickinson) in FACS buffer and stained with an antibody cocktail containing CD3-FITC, CD16-PE and anti-Siglec-7 antibody 4B12-AF647 for 1 hour on ice. After two washes, cells were fixed in PBS/2% PFA and acquired on a Novocyte flow cytometer. $IC_{50}$ values for internalization were determined based on plotting mean fluorescence in the APC channel on NK cells (gated as CD3-CD16+) and analysis using Prism Graphpad software.

Primary Tumor Analysis

Single cells from primary human tumor specimens were prepared using the Mylteni GentleMACS instrument according to the manufacturer's instructions. Cells were re-suspended in huFc block (Becton Dickinson) in FACS buffer and staining was performed using cocktails containing conjugated antibodies against immune cell surface markers, including CD3, CD8, CD16, CD45 and 7-AAD as a viability marker. CD8+ T cells were identified and gated as 7-AAD– CD45+ CD3+ CD8+. Anti-Siglec-7-PE (clone S7.7 Biolegend) was used to detect Siglec-7 levels. Cells were fixed in PBS/2% PFA and acquired on a Novocyte cytometer. Gating and analysis was performed using Flowjo software (Tristar).

Ligand levels on tumor cells were detected using Siglec-7-ECD-Fc as described under Ligand blocking assay above. As a specificity control, cells were treated with sialidase/neuraminidase (Roche) at 0.1 U/mL to remove sialic acids from the cell surface.

It is understood that the examples and embodiments described herein are for illustrative purposes only and that various modifications or changes in light thereof will be suggested to persons skilled in the art and are to be included within the spirit and purview of this application and scope of the appended claims. All publications, patents, accession numbers, and patent applications cited herein are hereby incorporated by reference for the purposes in the context of which they are cited.

Table of illustrative sequences

SEQ ID NO: 1 heavy chain variable region sequence (16H11); CDRs as defined by Kabat: underline; CDRs as defined by Chothia: bold, italics
QVQLHQSGAELVKPGASVKISCKGSGYDFSNFWMNWVKQRPGKGLEWIGQIYPGDGEIKYNGKFKGKATLT
ADESSSTAYIHLSSLTSEDSAVYFCARDDYLRAMDYWGQGTSVTVSS SEQ ID NO: 2 heavy chain variable region sequence (2G12); CDRs as defined by Kabat: underlined; CDRs as defined by Chothia: bold, italics
QVQLQQPGAELVKPGASVKLSCKASGYTFTSYWMQWVKQRPGQGLEWIGEIDPSVSYTEYNQKFKGKA
TLTVDTSSSTAYMQLSSLTSEDSAVYFCARWSKDYYGMDYWGQGTSVTVSS SEQ ID NO: 3 heavy chain variable region sequence (5D1); CDRs as defined by Kabat: underlined; CDRs as defined by Chothia: bold, italics
QVQLQQPGAELVKPGASVKMSCKASGYTFTSSWITWVKDRPGQGLEWIGDIYPGNGNTNYNEKFKSKA
TLTVDTSSNTVYMQLSSLTSEDSAVHYCARDGRGYFDYWGPGTTLTVSS SEQ ID NO: 4 heavy chain variable region sequence (8A2); CDRs as defined by Kabat: underlined; CDRs as defined by Chothia: bold, italics
QVQLKESGPGLVAPSQSLSITCTVSGFSLTTYGVDWVRQFPGKGLEWLGVIWGGGNTNYNSALMSRLS
ISKDTSKSQVFLKMNSLQTDDTAMYYCAKHKGTSHAMEYWGQGTSVTVSS SEQ ID NO: 11 heavy chain variable region sequence (4B12); CDRs as defined by Kabat: underlined; CDRs as defined by Chothia: bold, italics
EVQLQQSGPELVKPGASVKIPCKASGYTFTDYNMDWVKQSHEKSLEWIGDIDPHNGVTLYNQKFKDKA
TLTIDKSSNTAYMELRSLTSEDSAVYYCALTGSTYWGQGTLVTVSA SEQ ID NO: 15 light chain variable region sequence (16H11); CDRs as defined by both Kabat and Chothia are underlined
DIQMTQSPASLSASVGETVTITC<u>RASGNIHNYLA</u>WFQQKQGKSPHFLVY<u>SAKALAD</u>GVPSRFSGSGSG
TQYSLKINSLQPEDFGTYYC<u>QHFWSSPYT</u>FGGGTKLEIK SEQ ID NO: 16 light chain variable region sequence (2G12); CDRs as defined by both Kabat and Chothia are underlined.
DIVLTQSHKFMSTSVGDRVTITC<u>KASQDVSTAVA</u>WYQQKPGQSPKLLIY<u>WTSTRHT</u>GVPDRFTGSGSG
TDHTLTISSVQAEDLALYYC<u>HQQYSTPPT</u>FGGGTKLEIK SEQ ID NO: 18 light chain variable region sequence (8A2); CDRs as defined by both Kabat and Chothia are underlined.
QIVLTQSPAIMSASPGEKVTMTC<u>SASSRVIFMY</u>WYQQKPGSSPRLLIY<u>DTSNLAS</u>GVPVRFSGGGSGT
SYSLTISRMEAEDAATYYC<u>QQWSSYPPT</u>FGAGTKLELK SEQ ID NO: 17 light chain variable region sequence (5D1); CDRs as defined by both Kabat and Chothia are underlined.
DIQMTQTTSSLSASLGDRVTIIC<u>RASQDISNFLN</u>WYQQKPDGTVKLLMY<u>DTSILQS</u>GVPSRFSGRGSG
ADYSLTINNLEQEDLATYFC<u>QQGKTLPYT</u>FGGGTKLEIK SEQ ID NO: 25 light chain variable region sequence (4B12); CDRs as defined by both Kabat and Chothia are underlined.
DIVMTQSQKFMSTSVGDRVSVTC<u>KASQNVGTNVA</u>WYQQKPGQSPKAVIY<u>SASYRNS</u>GVPDRFTGSGSG
TDFTLTISNVQSEDLTEYFC<u>QQYNNYPYT</u>FGGGTKLEIK -continued Table of illustrative sequences SEQ ID NOS: 29-78-humanized variable region sequences derived from 16A11:
SEQ ID NO: 29 Humanized $V_H$ region 386-1 amino acid sequence; CDRs as defined by
Chothia are underlined
QVQLVQSGAEVKKPGSSVKVSCKAS<u>GYDFSNF</u>WISWVRQAPGQGLEWMGGI<u>YPGD
GE</u>INYAQKFQGRVTITADESTSTAYMELSSLRSEDTAVYYCAR<u>DDYLRAMDY</u>WGQG
TLVTVSS SEQ ID NO: 30 Humanized $V_H$ region 392-3 amino acid sequence; CDRs as defined by
Chothia are underlined
QVQLVQSGAEVKKPGSSVKVSCKAS<u>GYTFSNF</u>WISWVRQAPGQGLEWMGGI<u>YPGD
GE</u>INYAQKFQGRVTITADESTSTAYMELSSLRSEDTAVYYCAR<u>DDYLRAMDY</u>WGQG
TLVTVSS SEQ ID NO: 31 Humanized $V_H$ region 392-4 amino acid sequence; CDRs as defined by
Chothia are underlined
QVQLVQSGAEVKKPGSSVKVSCKAS<u>GGDFSNF</u>WISWVRQAPGQGLEWMGGI<u>YPGD
GE</u>INYAQKFQGRVTITADESTSTAYMELSSLRSEDTAVYYCAR<u>DDYLRAMDY</u>WGQG
TLVTVSS SEQ ID NO: 32 Humanized VH region 393-4 amino acid sequence; CDRs as defined by
Chothia are underlined
QVQLVQSGAEVKKPGSSVKVSCKAS<u>GYDFSNF</u>WISWVRQAPGQGLEWMGGI<u>IPGDG
E</u>INYAQKFQGRVTITADESTSTAYMELSSLRSEDTAVYYCAR<u>DDYLRAMDY</u>WGQGT
LVTVSS SEQ ID NO: 33 Humanized $V_H$ region 393-8 amino acid sequence; CDRs as defined by
Chothia are underlined
QVQLVQSGAEVKKPGSSVKVSCKAS<u>GYDFSNF</u>WISWVRQAPGQGLEWMGGI<u>YPIDG
E</u>INYAQKFQGRVTITADESTSTAYMELSSLRSEDTAVYYCAR<u>DDYLRAMDY</u>WGQGT
LVTVSS SEQ ID NO: 34 Humanized $V_H$ region 394-2 amino acid sequence; CDRs as defined by
Chothia are underlined
QVQLVQSGAEVKKPGSSVKVSCKAS<u>GYDFSNF</u>WISWVRQAPGQGLEWMGGI<u>YPGD
GT</u>INYAQKFQGRVTITADESTSTAYMELSSLRSEDTAVYYCAR<u>DDYLRAMDY</u>WGQG
TLVTVSS SEQ ID NO: 35 Humanized $V_H$ region 394-4 amino acid sequence; CDRs as defined by
Chothia are underlined
QVQLVQSGAEVKKPGSSVKVSCKAS<u>GYDFSNF</u>WISWVRQAPGQGLEWMGGI<u>YPGD
GEA</u>NYAQKFQGRVTITADESTSTAYMELSSLRSEDTAVYYCAR<u>DDYLRAMDY</u>WGQ
GTLVTVSS SEQ ID NO: 36 Humanized $V_H$ region 400-5 amino acid sequence; CDRs as defined by
Chothia are underlined
QVQLVQSGAEVKKPGSSVKVSCKAS<u>GYDFSSYA</u>ISWVRQAPGQGLEWMGGI<u>YPGD
GE</u>INYAQKFQGRVTITADESTSTAYMELSSLRSEDTAVYYCAR<u>DDYLRAMDY</u>WGQG
TLVTVSS SEQ ID NO: 37 Humanized $V_H$ region 400-7 amino acid sequence; CDRs as defined by
Chothia are underlined
QVQLVQSGAEVKKPGSSVKVSCKAS<u>GYDFSSF</u>WISWVRQAPGQGLEWMGGI<u>YPGD
GE</u>INYAQKFQGRVTITADESTSTAYMELSSLRSEDTAVYYCAR<u>DDYLRAMDY</u>WGQG
TLVTVSS SEQ ID NO: 38 Humanized $V_H$ region 400-9 amino acid sequence; CDRs as defined by
Chothia are underlined
QVQLVQSGAEVKKPGSSVKVSCKAS<u>GYDFSSY</u>WISWVRQAPGQGLEWMGGI<u>YPGD
GE</u>INYAQKFQGRVTITADESTSTAYMELSSLRSEDTAVYYCAR<u>DDYLRAMDY</u>WGQG
TLVTVSS SEQ ID NO: 39 Humanized $V_H$ region 400-14 amino acid sequence; CDRs as defined by
Chothia are underlined
QVQLVQSGAEVKKPGSSVKVSCKAS<u>GYDFSNYA</u>ISWVRQAPGQGLEWMGGI<u>YPGD
GE</u>INYAQKFQGRVTITADESTSTAYMELSSLRSEDTAVYYCAR<u>DDYLRAMDY</u>WGQG
TLVTVSS SEQ ID NO: 40 Humanized $V_H$ region 401-1 amino acid sequence; CDRs as defined by
Chothia are underlined
QVQLVQSGAEVKKPGSSVKVSCKAS<u>GYDFSNF</u>WISWVRQAPGQGLEWMGGI<u>YPGF
GE</u>INYAQKFQGRVTITADESTSTAYMELSSLRSEDTAVYYCAR<u>DDYLRAMDY</u>WGQG
TLVTVSS Table of illustrative sequences SEQ ID NO: 41 Humanized V_H region 417-8 amino acid sequence; CDRs as defined by Chothia are underlined
QVQLVQSGAEVKKPGSSVKVSCKAS<u>GYDFSNF</u>WMNWVRQAPGQGLEWMGG<u>IYPG
DGEINYAQKFQG</u>RVTITADESTSTAYMELSSLRSEDTAVYYCAR<u>DDYLRAMDV</u>WGQ
GTMVTVSS SEQ ID NO: 42 Humanized V_H region 417-17 amino acid sequence; CDRs as defined by Chothia are underlined
QVQLVQSGAEVKKPGSSVKVSCKAS<u>GYDFSNF</u>WMNWVRQAPGQGLEWMGG<u>IYPG
DGEINYAQKFQG</u>RVTITADESTSTAYMELSSLRSEDTAVYYCAR<u>DDYLRAMDI</u>WGQ
GTMVTVSS SEQ ID NO: 43 Humanized V_H region 387-11 amino acid sequence; CDRs as defined by Chothia are underlined
QVQLVQSGAEVKKPGSSVKVSCKGS<u>GYDFSNF</u>WMNWVRQAPGQGLEWMGQ<u>IYPG
DGEIKYNQKFQG</u>RVTLTADESTSTAYMELSSLRSEDTAVYFCAR<u>DDYLRAMDY</u>WG
QGTLVTVSS SEQ ID NO: 44 Humanized V_H region 410-1 amino acid sequence; CDRs as defined by Chothia are underlined
QVQLVQSGAEVKKPGSSVKVSCKAS<u>GYDFSNF</u>WMNWVRQAPGQGLEWMGG<u>IYPG
DGEINYAQKFQG</u>RVTITADESTSTAYMELSSLRSEDTAVYYCAR<u>DDYLRAMDY</u>WGQ
GTLVTVSS SEQ ID NO: 45 Humanized V_H region 438-4 amino acid sequence; CDRs as defined by Chothia are underlined
QVQLVQSGAEVKKPGSSVKVSCKAS<u>GYDFSNF</u>WMNWVRQAPGQGLEWMGQ<u>IYPG
DGEIKYNQKFQG</u>RVTLTADESTSTAYMELSSLRSEDTAVYFCAR<u>DDYLRAMDY</u>WG
QGTLVTVSS SEQ ID NO: 46 Humanized V_H region 440-2 amino acid sequence; CDRs as defined by Chothia are underlined
QVQLVQSGAEVKKPGSSVKVSCKGS<u>GYDFSNF</u>WMNWVRQAPGQGLEWMGQ<u>IYPG
DGEIKYNQKFQG</u>RVTLTADESTSTAYMELSSLRSEDTAVYFCAR<u>DDYLRAMDY</u>WGQ
GTLVTVSS SEQ ID NO: 47 Humanized V_H region 441-2 amino acid sequence; CDRs as defined by Chothia are underlined
QVQLVQSGAEVKKPGSSVKVSCKGS<u>GYDFSNF</u>WMNWVRQAPGQGLEWMGQ<u>IYPG
DGEIKYNQKFQG</u>RVTLTADESTSTAYMELSSLRSEDTAVYYCAR<u>DDYLRAMDI</u>WGQ
GTMVTVSS SEQ ID NO: 48 Humanized V_H region 443-1 amino acid sequence; CDRs as defined by Chothia are underlined
QVQLVQSGAEVKKPGSSVKVSCKGS<u>GYDFSNF</u>WMNWVRQAPGQGLEWMGQ<u>IYPG
DGEIKYNQKFQG</u>RVTLTADESTSTAYMELSSLRSEDTAVYYCAR<u>DDYLRAMDI</u>WGQ
GTMVTVSS SEQ ID NO: 49 Humanized V_H region 444-2 amino acid sequence; CDRs as defined by Chothia are underlined
QVQLVQSGAEVKKPGSSVKVSCKAS<u>GYDFSNF</u>WMNWVRQAPGQGLEWMGQ<u>IYPG
DGEIKYNQKFQG</u>RVTLTADESTSTAYMELSSLRSEDTAVYFCAR<u>DDYLRAMDY</u>WGQ
GTLVTVSS SEQ ID NO: 50 Humanized V_H region 445-3 amino acid sequence; CDRs as defined by Chothia are underlined
QVQLVQSGAEVKKPGSSVKVSCKAS<u>GYDFSNF</u>WMNWVRQAPGQGLEWMGQ<u>IYPG
DGEIKYNQKFQG</u>RVTLTADESTSTAYMELSSLRSEDTAVYYCAR<u>DDYLRAMDI</u>WGQ
GTMVTVSS SEQ ID NO: 51 Humanized V_H region 446-7 amino acid sequence; CDRs as defined by Chothia are underlined
QVQLVQSGAEVKKPGSSVKVSCKAS<u>GYDFSNF</u>WMNWVRQAPGQGLEWMGQ<u>IYPG
DGEIKYNQKFQG</u>RVTLTADESTSTAYMELSSLRSEDTAVYYCAR<u>DDYLRAMDI</u>WGQ
GTMVTVSS SEQ ID NO: 52 Humanized V_H region 447-2 amino acid sequence; CDRs as defined by Chothia are underlined
QVQLVQSGAEVKKPGSSVKVSCKAS<u>GYDFSNF</u>WMNWVRQAPGQGLEWMGQ<u>IYPG
DGEINYNQKFQG</u>RVTITADESTSTAYMELSSLRSEDTAVYYCAR<u>DDYLRAMDI</u>WGQ
GTMVTVSS SEQ ID NO: 53 Humanized V_H region 449-4 amino acid sequence; CDRs as defined by Chothia are underlined
QVQLVQSGAEVKKPGSSVKVSCKAS<u>GYDFSNF</u>WMNWVRQAPGQGLEWMGG<u>IYPG
DGEIKYNQKFQG</u>RVTITADESTSTAYMELSSLRSEDTAVYYCAR<u>DDYLRAMDI</u>WGQ
GTMVTVSS

| Table of illustrative sequences |
|---|
| SEQ ID NO: 54 Humanized V$_H$ region 449-6 amino acid sequence; CDRs as defined by Chothia are underlined<br>QVQLVQSGAEVKKPGSSVKVSCKGS<u>GYDFSNF</u>WMNWVRQAPGQGLEWMGG<u>IYPG</u><u>DGEI</u>KYNQKFQGRVTITADESTSTAYMELSSLRSEDTAVYYCAR<u>DDYLRAMDI</u>WGQGTMVTVSS |
| SEQ ID NO: 55 Humanized V$_H$ region 463-2 amino acid sequence; CDRs as defined by Chothia are underlined<br>QVQLVQSGAEVKKPGSSVKVSCKAS<u>GYDFSNF</u>WMNWVRQAPGQGLEWMGQ<u>IYPG</u><u>DGEI</u>KYNQKFQGRVTITADESTSTAYMELSSLRSEDTAVYYCAR<u>DDYLRAMDY</u>WGQGTLVTVSS |
| SEQ ID NO: 56 Humanized V$_H$ region 465-2 amino acid sequence; CDRs as defined by Chothia are underlined<br>QVQLVQSGAEVKKPGSSVKVSCKAS<u>GYDFSNF</u>WMNWVRQAPGQGLEWMGQ<u>IYPG</u><u>DGEI</u>NYAQKFQGRVTITADESTSTAYMELSSLRSEDTAVYYCAR<u>DDYLRAMDI</u>WGQGTMVTVSS |
| SEQ ID NO: 57 Humanized V$_H$ region 465-17 amino acid sequence; CDRs as defined by Chothia are underlined<br>QVQLVQSGAEVKKPGSSVKVSCKAS<u>GYDFSNF</u>WMNWVRQAPGQGLEWMGQ<u>IYPG</u><u>DGEI</u>KYAQKFQGRVTITADESTSTAYMELSSLRSEDTAVYYCAR<u>DDYLRAMDI</u>WGQGTMVTVSS |
| SEQ ID NO: 58 Humanized V$_H$ region 484-6 amino acid sequence; CDRs as defined by Chothia are underlined<br>QVQLVQSGAEVKKPGSSVKVSCKAS<u>GYDFSNY</u>WMNWVRQAPGQGLEWMGQ<u>IYPG</u><u>DGEI</u>KYNQKFQGRVTITADESTSTAYMELSSLRSEDTAVYYCAR<u>DDYLRAMDI</u>WGQGTMVTVSS |
| SEQ ID NO: 59 Humanized V$_H$ region 484-7 amino acid sequence; CDRs as defined by Chothia are underlined<br>QVQLVQSGAEVKKPGSSVKVSCKAS<u>GYDFSNY</u>WMNVVVRQAPGQGLEWMGQ<u>IYPG</u><u>DGEI</u>KYNQKFQGRVTITADESTSTAYMELSSLRSEDTAVYYCAR<u>DDYLRAMDY</u>WGQGTLVTVSS |
| SEQ ID NO: 60 Humanized V$_H$ region 485-4 amino acid sequence; CDRs as defined by Chothia are underlined<br>QVQLVQSGAEVKKPGSSVKVSCKAS<u>GYDFSNF</u>AMNWVRQAPGQGLEWMGQ<u>IYPG</u><u>DGEI</u>KYNQKFQGRVTITADESTSTAYMELSSLRSEDTAVYYCAR<u>DDYLRAMDY</u>WGQGTLVTVSS |
| SEQ ID NO: 61 Humanized V$_H$ region 485-5 amino acid sequence; CDRs as defined by Chothia are underlined<br>QVQLVQSGAEVKKPGSSVKVSCKAS<u>GYDFSNF</u>AMNWVRQAPGQGLEWMGQ<u>IYPG</u><u>DGEI</u>KYNQKFQGRVTITADESTSTAYMELSSLRSEDTAVYYCAR<u>DDYLRAMDI</u>WGQGTMVTVSS |
| SEQ ID NO: 62 Humanized V$_L$ region 381-1 amino acid sequence; CDRs as defined by Chothia are underlined<br>DIQMTQSPSSLSASVGDRVTITC<u>RASGNIHNYLA</u>WYQQKPGKAPKLLLY<u>SAKRLES</u>GVPSRFSGSGSGTDYTLTISSLQPEDFATYYC<u>QHFWSSPYT</u>FGGGTKVEIK |
| SEQ ID NO: 63 Humanized V$_L$ region 390-8 amino acid sequence; CDRs as defined by Chothia are underlined<br>DIQMTQSPSSLSASVGDRVTITC<u>RASGNIHNSLA</u>WYQQKPGKAPKLLLY<u>SAKRLES</u>GVPSRFSGSGSGTDYTLTISSLQPEDFATYYC<u>QHFWSSPYT</u>FGGGTKVEIK |
| SEQ ID NO: 64 Humanized V$_L$ region 391-1 amino acid sequence; CDRs as defined by Chothia are underlined<br>DIQMTQSPSSLSASVGDRVTITC<u>RASGNIHNYLA</u>WYQQKPGKAPKLLLY<u>AASRLES</u>GVPSRFSGSGSGTDYTLTISSLQPEDFATYYC<u>QHFWSSPYT</u>FGGGTKVEIK |
| SEQ ID NO: 65 Humanized V$_L$ region 391-8 amino acid sequence; CDRs as defined by Chothia are underlined<br>DIQMTQSPSSLSASVGDRVTITC<u>RASGNIHNYLA</u>WYQQKPGKAPKLLLY<u>SASRLES</u>GVPSRFSGSGSGTDYTLTISSLQPEDFATYYC<u>QHFWSSPYT</u>FGGGTKVEIK |
| SEQ ID NO: 66 Humanized V$_L$ region 395-1 amino acid sequence; CDRs as defined by Chothia are underlined<br>DIQMTQSPSSLSASVGDRVTITC<u>RASGGIHNYLA</u>WYQQKPGKAPKLLLY<u>SAKRLES</u>GVPSRFSGSGSGTDYTLTISSLQPEDFATYYC<u>QHFWSSPYT</u>FGGGTKVEIK |
| SEQ ID NO: 67 Humanized V$_L$ region 395-4 amino acid sequence; CDRs as defined by Chothia are underlined<br>DIQMTQSPSSLSASVGDRVTITC<u>RASQNIHNYLA</u>WYQQKPGKAPKLLLY<u>SAKRLES</u>GVPSRFSGSGSGTDYTLTISSLQPEDFATYYC<u>QHFWSSPYT</u>FGGGTKVEIK |

Table of illustrative sequences
-continued

SEQ ID NO: 68 Humanized V_L region 396-2 amino acid sequence; CDRs as defined by Chothia are underlined
DIQMTQSPSSLSASVGDRVTITC<u>RASGNISNYLA</u>WYQQKPGKAPKLLLY<u>SAKRLES</u>G
VPSRFSGSGSGTDYTLTISSLQPEDFATYYC<u>QHFWSSPYT</u>FGGGTKVEIK SEQ ID NO: 69 Humanized V_L region 418-2 amino acid sequence; CDRs as defined by Chothia are underlined
DIQMTQSPSSLSASVGDRVTITC<u>RASGNIHNYLA</u>WYQQKPGKAPKFLLY<u>SAKRLES</u>G
VPSRFSGSGSGTDYTLTISSLQPEDFATYYC<u>QHFWSSPYT</u>FGGGTKVEIK SEQ ID NO: 70 Humanized V_L region 419-2 amino acid sequence; CDRs as defined by Chothia are underlined
DIQMTQSPSSLSASVGDRVTITC<u>RASQNIHNYLA</u>WYQQKPGKAPKFLLY<u>SAKRLES</u>G
VPSRFSGSGSGTDYTLTISSLQPEDFATYYC<u>QHFWSSPYT</u>FGGGTKVEIK SEQ ID NO: 71 Humanized V_L region 421-3 amino acid sequence; CDRs as defined by Chothia are underlined
DIQMTQSPSSLSASVGDRVTITC<u>RASGNIHNYLA</u>WYQQKPGKAPKFLLY<u>SAKRLES</u>G
VPSRFSGSGSGTDYTLTISSLQPEDFATYYC<u>QHFWSSPYT</u>FGQGTKLEIK SEQ ID NO: 72 Humanized V_L region 424-1 amino acid sequence; CDRs as defined by Chothia are underlined
DIQMTQSPSSLSASVGDRVTITC<u>RASGNIHNYLA</u>WYQQKPGKAPKLLLY<u>SAKRLAS</u>G
VPSRFSGSGSGTDYTLTISSLQPEDFATYYC<u>QHFWSSPYT</u>FGGGTKVEIK SEQ ID NO: 73 Humanized V_L region 425-3 amino acid sequence; CDRs as defined by Chothia are underlined
DIQMTQSPSSLSASVGDRVTITC<u>RASGNIHNYLA</u>WYQQKPGKAPKLLLY<u>SAKRLED</u>G
VPSRFSGSGSGTDYTLTISSLQPEDFATYYC<u>QHFWSSPYT</u>FGGGTKVEIK SEQ ID NO: 74 Humanized V_L region 426-2 amino acid sequence; CDRs as defined by Chothia are underlined
DIQMTQSPSSLSASVGDRVTITC<u>RASQNIHNYLA</u>WYQQKPGKAPKLLLY<u>SAKRLAS</u>G
VPSRFSGSGSGTDYTLTISSLQPEDFATYYC<u>QHFWSSPYT</u>FGGGTKVEIK SEQ ID NO: 75 Humanized V_L region 427-1 amino acid sequence; CDRs as defined by Chothia are underlined
DIQMTQSPSSLSASVGDRVTITC<u>RASQNIHNYLA</u>WYQQKPGKAPKLLLY<u>SAKRLED</u>G
VPSRFSGSGSGTDYTLTISSLQPEDFATYYC<u>QHFWSSPYT</u>FGGGTKVEIK SEQ ID NO: 76 Humanized V_L region 435-7 amino acid sequence; CDRs as defined by Chothia are underlined
DIQMTQSPSSLSASVGDRVTITC<u>RASQNIHNYLA</u>WYQQKPGKAPKFLLY<u>SAKRLED</u>G
VPSRFSGSGSGTDYTLTISSLQPEDFATYYC<u>QHFWSSPYT</u>FGGGTKVEIK SEQ ID NO: 77 Humanized V_L region 439-5 amino acid sequence
DIQMTQSPSSLSASVGDRVTITC<u>RASQNIHNYLA</u>WYQQKPGKAPKFLLY<u>SAKRLED</u>G
VPSRFSGSGSGTDYTLTISSLQPEDFATYYC<u>QHFWSSPYT</u>FGQGTKLEIK SEQ ID NO: 78 Humanized V_L region 448-3 amino acid sequence
DIQMTQSPSSLSASVGDRVTITC<u>RASQNIHNYLA</u>WYQQKPGKAPKFLLY<u>SAKRLES</u>G
VPSRFSGSGSGTDYTLTISSLQPEDFATYYC<u>QHFWSSPYT</u>FGQGTKLEIK SEQ ID NOS: 104-107 humanized variable region sequences derived from 8A2:
SEQ ID NO: 104 humanized heavy chain variable region sequence RHA; CDRs as defined by Chothia are underlined
QVQLQESGPGLVKPSETLSLTCTVS<u>GFSLTTYGWS</u>WIRQPPGKGLEWIGYI<u>WGGGN</u>T
NYNPSLKSRVTISVDTSKNQFSLKLSSVTAADTAVYYCAK<u>HKGTSHAMEY</u>WGQGT
MVTVSS SEQ ID NO: 105: humanized light chain variable region sequence RKA; CDRs as defined by Chothia are underlined
EIVLTQSPATLSLSPGERATLSC<u>RASSRVIFLA</u>WYQQKPGQAPRLLIY<u>DTSNKAT</u>GVP
ARFSGSGSGTDFTLTISSLEPEDFAVYYC<u>QQWSSYPPT</u>FGGGTKVEIK SEQ ID NO: 106 humanized heavy chain variable region sequence RHB; CDRs as defined by Chothia are underlined
QVQLQESGPGLVKPSETLSLTCTVS<u>GFSLTTYG</u>VDWVRQPPGKGLEWIGVI<u>WGGGN</u>T
NYNSSLKSRVTISKDTSKNQVFLKLSSVTAADTAVYYCAK<u>HKGTSHAMEY</u>WGQGT
MVTVSS SEQ ID NO: 107 humanized light chain variable region sequence RKB; CDRs as defined by Chothia are underlined
QIVLTQSPATLSLSPGERATLSC<u>RASSRVIFMY</u>WYQQKPGQSPRLLIY<u>DTSNLAT</u>GVP
ARFSGGGSGTDYTLTISSLEPEDFAVYYC<u>QQWSSYPPT</u>FGGGTKVEIK

What is claimed is:

1. An anti-Siglec-7 antibody that binds to Siglec-7 and comprises:
    (a) an HCDR1 sequence GYDFSNF (SEQ ID NO:79), an HCDR2 sequence YPGDGE (SEQ ID NO:80), an HCDR3 sequence DDYLRAMDY (SEQ ID NO:81), an an LCDR1 sequence RASGNIHNYLA (SEQ ID NO:93), an LCDR2 sequence SAKRLES (SEQ ID NO:94), and an LCDR3 sequence QHFWSSPYT (SEQ ID NO:95);
    (b) an HCDR1 sequence GYDFSNF (SEQ ID NO:79), an HCDR2 sequence YPGDGE (SEQ ID NO:80), an HCDR3 sequence DDYLRAMDY (SEQ ID NO:81), an LCDR1 sequence RASQNIHNYLA (SEQ ID NO:100), an LCDR2 sequence SAKRLES (SEQ ID NO:94), and an LCDR3 sequence QHFWSSPYT (SEQ ID NO:95);
    (c) an HCDR1 sequence GYDFSNF (SEQ ID NO:79), an HCDR2 sequence YPGDGE (SEQ ID NO:80), an HCDR3 sequence DDYLRAMDV (SEQ ID NO:91), an LCDR1 sequence RASQNIHNYLA (SEQ ID NO:100), an LCDR2 sequence SAKRLES (SEQ ID NO:94), and an LCDR3 sequence QHFWSSPYT (SEQ ID NO:95);
    (d) an HCDR1 sequence GYDFSNF (SEQ ID NO:79), an HCDR2 sequence YPGDGE (SEQ ID NO:80), an HCDR3 sequence DDYLRAMDV (SEQ ID NO:91), an LCDR1 sequence RASQNIHNYLA (SEQ ID NO:100), an LCDR2 sequence SAKRLED (SEQ ID NO:103), and an LCDR3 sequence QHFWSSPYT (SEQ ID NO:95);
    (e) an HCDR1 sequence GYDFSNF (SEQ ID NO:79), an HCDR2 sequence YPGDGE (SEQ ID NO:80), an HCDR3 sequence DDYLRAMDI (SEQ ID NO:92), an LCDR1 sequence RASGNIHNYLA (SEQ ID NO:93), an LCDR2 sequence SAKRLES (SEQ ID NO:94), and an LCDR3 sequence QHFWSSPYT (SEQ ID NO:95);
    (f) an HCDR1 sequence GYDFSNF (SEQ ID NO:79), an HCDR2 sequence YPGDGE (SEQ ID NO:80), an HCDR3 sequence DDYLRAMDI (SEQ ID NO:92), an LCDR1 sequence RASGNIHNYLA (SEQ ID NO:93), an LCDR2 sequence SAKRLED (SEQ ID NO:103), and an LCDR3 sequence QHFWSSPYT (SEQ ID NO:95);
    (g) an HCDR1 sequence GYDFSNF (SEQ ID NO:79), an HCDR2 sequence YPGDGE (SEQ ID NO:80), an HCDR3 sequence DDYLRAMDI (SEQ ID NO:92), an LCDR1 sequence RASQNIHNYLA (SEQ ID NO:100), an LCDR2 sequence SAKRLES (SEQ ID NO:94), and an LCDR3 sequence QHFWSSPYT (SEQ ID NO:95);
    (h) an HCDR1 sequence GYDFSNF (SEQ ID NO:79), an HCDR2 sequence YPGDGE (SEQ ID NO:80), an HCDR3 sequence DDYLRAMDI (SEQ ID NO:9 2), an LCDR1 sequence RASQNIHNYLA (SEQ ID NO:100), an LCDR2 sequence SAKRLED (SEQ ID NO:103), and an LCDR3 sequence QHFWSSPYT (SEQ ID NO:95);
    (i) an HCDR1 sequence GYDFSNY (SEQ ID NO:89), an HCDR2 sequence YPGDGE (SEQ ID NO:80), an HCDR3 sequence DDYLRAMDI (SEQ ID NO:92), an LCDR1 sequence RASGNIHNYLA (SEQ ID NO:93), an LCDR2 sequence SAKRLES (SEQ ID NO:94), and an LCDR3 sequence QHFWSSPYT (SEQ ID NO:95);
    (j) an HCDR1 sequence GYDFSNY (SEQ ID NO:89), an HCDR2 sequence YPGDGE (SEQ ID NO:80), an HCDR3 sequence DDYLRAMDI (SEQ ID NO:92), an LCDR1 sequence RASQNIHNYLA (SEQ ID NO:100), an LCDR2 sequence SAKRLES (SEQ ID NO:94), and an LCDR3 sequence QHFWSSPYT (SEQ ID NO:95);
    (k) an HCDR1 sequence GYDFSNY (SEQ ID NO:89), an HCDR2 sequence YPGDGE (SEQ ID NO:80), an HCDR3 sequence DDYLRAMDY(SEQ ID NO:81), an LCDR1 sequence RASQNIHNYLA (SEQ ID NO:100), an LCDR2 sequence SAKRLES (SEQ ID NO:94), and an LCDR3 sequence QHFWSSPYT (SEQ ID NO:95); or
    (l) an HCDR1 sequence GYDFSNF (SEQ ID NO:79), an HCDR2 sequence YPGDGE (SEQ ID NO:80), an HCDR3 sequence DDYLRAMDV (SEQ ID NO:91), an LCDR1 sequence RASGNIHNYLA (SEQ ID NO:93), an LCDR2 sequence SAKRLES (SEQ ID NO:94), and an LCDR3 sequence QHFWSSPYT (SEQ ID NO:95).

2. The anti-Siglec-7 antibody of claim 1, wherein the antibody comprises:
    (a) a heavy chain variable region comprising HCDR1 sequence GYDFSNF (SEQ ID NO:79), HCDR2 sequence YPGDGE (SEQ ID NO:80), and HCDR3 sequence DDYLRAMDY (SEQ ID NO:81); and a light chain variable region comprising LCDR1 sequence RASGNIHNYLA (SEQ ID NO:93), LCDR2 sequence SAKRLES (SEQ ID NO:94), and LCDR3 sequence QHFWSSPYT (SEQ ID NO:95);

(b) a heavy chain variable region comprising HCDR1 sequence GYDFSNF (SEQ ID NO:79), HCDR2 sequence YPGDGE (SEQ ID NO:80), and HCDR3 sequence DDYLRAMDI (SEQ ID NO:92); and a light chain variable region comprising LCDR1 sequence RASGNIHNYLA (SEQ ID NO:93), LCDR2 sequence SAKRLES(SEQ ID NO:94), and LCDR3 sequence QHFWSSPYT (SEQ ID NO:95); or (c) a heavy chain variable region comprising HCDR1 sequence GYDFSNY(SEQ ID NO:89), HCDR2 sequence YPGDGE (SEQ ID NO:80), and HCDR3 sequence DDYLRAMDI (SEQ ID NO:92); and a light chain variable region comprising LCDR1 sequence RASGNIHNYLA (SEQ ID NO:93), LCDR2 sequence SAKRLES (SEQ ID NO:94), and LCDR3 sequence QHFWSSPYT (SEQ ID NO:95).

3. The anti-Siglec-7 antibody of claim 1, wherein the antibody comprises:

(a) a heavy chain variable region comprising HCDR1 sequence GYDFSNF (SEQ ID NO:79), HCDR2 sequence YPGDGE (SEQ ID NO:80), and HCDR3 sequence DDYLRAMDI (SEQ ID NO:92); and a light chain variable region comprising LCDR1 sequence RASQNIHNYLA (SEQ ID NO:100), LCDR2 sequence SAKRLES (SEQ ID NO:94), and LCDR3 sequence QHFWSSPYT (SEQ ID NO:95);

(b) a heavy chain variable region comprising CDR1 sequence GYDFSNY(SEQ ID NO:89), HCDR2 sequence YPGDGE (SEQ ID NO:80), and HCDR3 sequence DDYLRAMDY (SEQ ID NO:81); and a light chain variable region comprising LCDR1 sequence RASQNIHNYLA (SEQ ID NO:100), LCDR2 sequence SAKRLES (SEQ ID NO:94), and LCDR3 sequence QHFWSSPYT (SEQ ID NO:95);

(c) a heavy chain variable region comprising HCDR1 sequence GYDFSNY (SEQ ID NO:89), HCDR2 sequence YPGDGE (SEQ ID NO:80), and HCDR3 sequence DDYLRAMDI (SEQ ID NO:92); and a light c ha invariable region comprising LCDR1 sequence RASQNIHNYLA (SEQ ID NO:100), LCDR2 sequence SAKRLES (SEQ ID NO:94), and LCDR3 sequence QHFWSSPYT (SEQ ID NO:95); or (d) a heavy chain variable region comprising GYDFSNF (SEQ ID NO:79), HCDR2 sequence YPGDGE (SEQ ID NO:80), and HCDR3 sequence DDYLRAMDY (SEQ ID NO:81); and a light chain variable region comprising LCDR1 sequence RASQNIHNYLA (SEQ ID NO:100), LCDR2 sequence SAKRLES (SEQ ID NO:94), and LCDR3 sequence QHFWSSPYT (SEQ ID NO:95).

4. The anti-Siglec-7 antibody of claim 1, wherein the antibody comprises a heavy chain variable region comprising HCDR1 sequence GYDFSNY(SEQ ID NO:89), HCDR2 sequence YPGDGE (SEQ ID NO:80), and HCDR3 sequence DDYLRAMDY (SEQ ID NO:81); and a light chain variable region comprising LCDR1 sequence RASQNIHNYLA (SEQ ID NO:100), LCDR2 sequence SAKRLES (SEQ ID NO:94), and LCDR3 sequence QHFWSSPYT (SEQ ID NO:95).

5. The anti-Siglec-7 antibody of claim 1, wherein the heavy chain variable region has at least 95% identity to the amino acid sequence of any one of SEQ ID NOS:41, 42, 43, 44, 45, 46, 47, 48, 49, 50, 51, 52, 53, 54, 55, 57, 58, or 59; and the light chain variable region has at least 95% identity to the amino acid sequence of any one of SEQ ID NOS:69, 70, 71, 76, 77, or 78.

6. The anti-Siglec-7 antibody of claim 1, wherein the antibody comprises: a heavy chain variable region comprising the amino acid sequence of any one of claims SEQ ID NOS:41, 42, 43, 44, 45, 46, 47, 48, 49, 50, 51, 52, 53, 54, 55, 57, 58, or 59; and alight chain variable region comprising the amino acid sequence of any one of SEQ ID NOS:69, 70, 71, 76, 77, or 78.

7. The anti-Siglec-7 antibody of claim 1, wherein the antibody comprises: a heavy chain variable region comprising the amino acid sequence of any one of claims SEQ ID NOS:43, 45, 46, 47, 48, 49, 50, 51, 52, 53, 54, 55, 57, 58, or 59; and a light chain variable region comprising the amino acid sequence of SEQ ID NO:69 or 78.

8. The anti-Siglec-7 antibody of claim 1, wherein the antibody comprises: a heavy chain variable region comprising the amino acid sequence of any one of SEQ ID NOS:43, 45, 56, 47, 48, 49, 50, 51, 52, 53, 54, 55, 57, or 58; and a light chain variable region comprising the amino acid sequence of SEQ ID NO:69.

9. The anti-Siglec-7 antibody of claim 1, wherein the antibody comprises: a heavy chain variable region comprising the amino acid sequence of any one of SEQ ID NOS:51, 52, 54, 55, 57, 58, or 59; and a light chain variable region comprising the amino acid sequence of SEQ ID NO:78.

10. The anti-Siglec-7 antibody of claim 1, wherein the antibody comprises:

(a) a heavy chain variable region comprising the amino acid sequence of SEQ ID NO:55 and a light chain variable region comprising the amino acid sequence of SEQ ID NO:69;

(b) a heavy chain variable region comprising the amino acid sequence of SEQ ID NO:57 and a light chain variable region comprising the amino acid sequence of SEQ ID NO:69; or (c) a heavy chain variable region comprising the amino acid sequence of SEQ ID NO:59 and a light chain variable region comprising the amino acid sequence of SEQ ID NO:78.

11. The anti-Siglec-7 antibody of claim 1, wherein the heavy chain variable region comprises the amino acid sequence of SEQ ID NO:59 and the light chain variable region comprise the amino acid sequence of SEQ ID NO:78.

12. The anti-Siglec-7 antibody of claim 1, wherein the antibody is in a monovalent form, is a multivalent Fab form, or is an IgG.

13. A bispecific or multi-specific antibody that comprises the antibody of claim 1.

14. A pharmaceutical composition comprising the antibody of claim 1.

* * * * *